(12) United States Patent
Pellicciari et al.

(10) Patent No.: US 11,345,721 B2
(45) Date of Patent: *May 31, 2022

(54) TGR5 MODULATORS AND METHODS OF USE THEREOF

(71) Applicant: Intercept Pharmaceuticals, Inc., Morristown, NJ (US)

(72) Inventors: Roberto Pellicciari, Perugia (IT); Antimo Gioiello, Perugia (IT); Antonio Macchiarulo, Perugia (IT); Francoise Perron-Sierra, Paris (FR); Klaus Seedorf, Hamburg (DE)

(73) Assignee: INTERCEPT PHARMACEUTICALS, INC., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/010,505

(22) Filed: Sep. 2, 2020

(65) Prior Publication Data

US 2021/0122779 A1 Apr. 29, 2021

Related U.S. Application Data

(63) Continuation of application No. 15/742,595, filed as application No. PCT/US2016/037812 on Jun. 16, 2016, now Pat. No. 10,800,807.

(60) Provisional application No. 62/182,081, filed on Jun. 19, 2015.

(30) Foreign Application Priority Data

Jun. 24, 2015 (EP) ..................... 15305976

(51) Int. Cl.
*C07J 9/00* (2006.01)
*C07J 43/00* (2006.01)
*A61P 1/16* (2006.01)
*C07J 41/00* (2006.01)
*A61P 3/08* (2006.01)

(52) U.S. Cl.
CPC .............. *C07J 9/005* (2013.01); *A61P 1/16* (2018.01); *A61P 3/08* (2018.01); *C07J 41/00* (2013.01); *C07J 41/0061* (2013.01); *C07J 43/003* (2013.01)

(58) Field of Classification Search
CPC ..................... C07J 9/005; A61P 3/08
See application file for complete search history.

(56) References Cited

U.S. PATENT DOCUMENTS

| | | | |
|---|---|---|---|
| 8,114,862 B2 | 2/2012 | Pellicciari | |
| 8,445,472 B2 | 5/2013 | Pellicciari | |
| 8,796,249 B2 | 8/2014 | Pellicciari | |
| 8,999,964 B2 | 4/2015 | Pellicciari | |
| 9,243,027 B2 | 1/2016 | Pellicciari | |
| 9,540,414 B2 | 1/2017 | Pellicciari | |
| 9,650,409 B2 | 5/2017 | Pellicciari | |
| 10,407,462 B2 | 9/2019 | Zampella et al. | |
| 10,800,807 B2 * | 10/2020 | Pellicciari | C07J 9/005 |

FOREIGN PATENT DOCUMENTS

| | | |
|---|---|---|
| CN | 107531743 A | 1/2018 |
| EP | 1 947 108 A | 7/2008 |
| EP | 3 290 429 A1 | 3/2018 |
| WO | WO 02/084286 A1 | 10/2002 |
| WO | WO 2010/059853 A1 | 5/2010 |
| WO | WO 2016/086115 A1 | 6/2016 |
| WO | WO 2016/086169 A1 | 6/2016 |
| WO | WO 2016/086218 A1 | 6/2016 |
| WO | WO 2016/205475 A2 | 12/2016 |

OTHER PUBLICATIONS

Ballatore, C. "Carboxylic Acid (Bio)Isosteres in Drug Design", ChemMedChem, 2013, vol. 8, No. 3, p. 385-395.

Katsuma S. et al. "Bile acids promote glucagon-like peptide-1 secretion through GR5 in a murine enteroendocrine cell line STC-1", Biochemical and Biophysical Research Communications, 2005, vol. 329, p. 386-390.

Kawamata J. et al., "A G Protein-coupled Receptor Responsive to Bile Acids", The Journal of Biological Chemistry, 2003, vol. 278, p. 9435-9440.

(Continued)

*Primary Examiner* — Golam M Shameem

(57) ABSTRACT

The application relates to compounds of formula A:

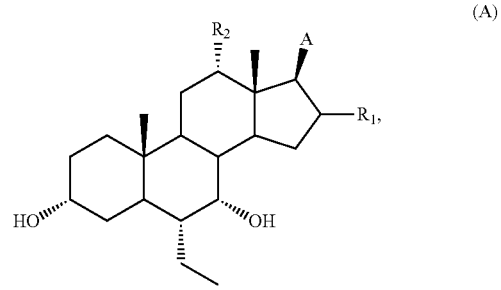

(A)

or a salt, solvate, ester, tautomer, amino acid conjugate, or metabolite thereof. The compounds of formula A are TGR5 modulators useful for the treatment of various diseases, including metabolic disease, inflammatory disease, autoimmune disease, cardiac disease, kidney disease, cancer, and gastrointestinal disease.

6 Claims, No Drawings

(56) References Cited

OTHER PUBLICATIONS

Maruyama T. et al., "Targeted disruption of G protein-coupled bile acid receptor 1 (Gpbar1/M-Bar) in mice", Journal of Endocrinology, 2006, vol. 191, p. 197-205.

Patani and LaVoie, "Bioisosterism: A Rational Approach in Drug Design", Chem. Rev. 1996, vol. 96, p. 3147-3176.

Pellicciari R. et al. "Nongenomic actions of bile acids. Synthesis and preliminary characterization of 23- and 6,23-alkyl-substituted bile acid derivatives as selective modulators for the G-protein coupled receptor TGR5", Journal of Medicinal Chemistry, vol. 50, No. 18, 2007, pp. 4265-4268.

Pellicciari R. et al. "Bile Acid Derivatives as Ligands of the Farnesoid X Receptor. Synthesis, Evaluation, and Structure-Activity Relationship of a Series of Body and Side Chain Modified Analogues of Chenodeoxycholic Acid", Journal of Medicinal Chemistry, vol. 47, 2004, pp. 4559-4569.

Pellicciari R. et al. "Discovery of 6alpha-Ethyl-23(S)-methylcholic Acid (S-EMCA, INT-777) as a Potent and Selective Agonist for the TGR5 Receptor, a Novel Target for Diabesity", Journal of Medicinal Chemistry, 2009, vol. 52, p. 7958-7961.

Liu Qingshan, "New Technology for High-throughput Screening of National Drugs", The Central University of Nationalities Press, 2008, p. 77. (English summary enclosed).

Sato Hiroyuki et al. "Novel potent and selective bile acid derivatives as TGR5 5 agonists: biological screening, structure-activity relationships, and molecular modeling studies", Journal of Medicinal Chemistry, vol. 51, No. 6, 2008, pp. 1831-1841.

Takeda S. et al. "Identification of G protein-coupled receptor genes from the human genome sequence", FEBS Letters, 2002, vol. 520, p. 97-101.

Watanabe S. et al. "Bile acids induce energy expenditure by promoting intracellular thyroid hormone activation", Nature, 2006, vol. 439, p. 484-489.

\* cited by examiner

TGR5 MODULATORS AND METHODS OF USE THEREOF

RELATED APPLICATIONS

This application is a continuation application of U.S. application Ser. No. 15/742,595, filed on Sep. 26, 2018, now U.S. Pat. No. 10,800,807, which is a national stage application, filed under 35 U.S.C. § 371, of PCT Application No. PCT/US2016/037812, filed on Jun. 16, 2016, which claims benefit of and priority to U.S. Provisional Application No. 62/182,081, filed on Jun. 19, 2015, and to European Application No. 15305976.1, filed on Jun. 24, 2015. The contents of each of these applications are hereby incorporated by reference in their entirety.

FIELD OF THE APPLICATION

The application relates to compounds that modulate TGR5 and compositions useful in methods for the treatment and/or prevention of various diseases.

BACKGROUND

TGR5 is a G-protein-coupled cell-surface receptor that is responsive to bile acids (BAs). The primary structure of TGR5 and its responsiveness to bile acids has been found to be highly conserved in human, cow, rabbit, rat, and mouse, and thus suggests that TGR5 has important physiological functions. TGR5 is widely distributed in not only lymphoid tissues but also other tissues. High levels of TGR5 mRNA have been detected in placenta, spleen, and monocytes/macrophages. Bile acids have been shown to induce internalization of the TGR5 fusion protein from the cell membrane to the cytoplasm (Kawamata et al., 2003, *J. Bio. Chem.* 278, 9435). TGR5 has been found to be identical to hGPCR19 (Takeda et al. 2002, *FEBS Lett* 520, 97).

TGR5 is associated with the intracellular accumulation of cAMP, which is widely expressed in diverse cell types. While its activation in macrophages decreases pro-inflammatory cytokine production (Kawamata et al., 2003, *J. Bio. Chem.* 278, 9435), the stimulation of TGR5 by BAs in adipocytes and myocytes enhances energy expenditure (Watanabe et al., 2006, *Nature* 439, 484). This latter effect involves the cAMP-dependent induction of type 2 iodothyronine deiodinase (D2), which, by locally converting T4 into T3, gives rise to increased thyroid hormone activity. Consistent with the role of TGR5 in energy metabolism, female TGR5 knock-out mice show a significant fat accumulation with body weight gain when challenged with a high fat diet, indicating that the lack of TGR5 decreases energy expenditure and elicits obesity (Maruyama et al., 2006, *J. Endocrinol.* 191, 197). In addition and in line with the involvement of TGR5 in energy homeostasis, bile acid activation of the membrane receptor has been reported to promote the production of glucagon-like peptide 1 (GLP-1) in murine enteroendocrine cell lines (Katsuma, 2005, *Biochem. Biophys. Res. Comm.* 329, 386). Thus, TGR5 is an attractive target for the treatment of diseases (e.g., obesity, diabetes and metabolic syndrome).

In addition to the use of TGR5 agonists for the treatment and prevention of metabolic diseases, compounds that modulate TGR5 are also useful for the treatment of other diseases, e.g., central nervous diseases as well as inflammatory diseases (WO 01/77325 and WO 02/84286). Moreover, modulators of TGR5 can be used in methods of regulating bile acid and cholesterol homeostasis, fatty acid absorption, and protein and carbohydrate digestion.

Recently, 23-alkyl-substituted and 6,23-dialkyl-substituted derivatives of chenodeoxycholic acid (CDCA), such as 6α-ethyl-23(S)-methyl-chenodeoxycholic acid, have been reported as potent and selective agonists of TGR5 (Pellicciari et al., 2007, *J. Med. Chem.* 50, 4265). TGR5 agonists have also provided for the first time a pharmacological differentiation of genomic versus nongenomic effects of BAs and allowed for informative structure-activity relationship studies. In this context, the availability of more potent and selective TGR5 modulators is necessary to further identify additional features affecting receptor activation and to characterize the physiological and pharmacological actions of this receptor in order to better understand its relationship to the prevention and treatment of diseases.

Thus, there is a need for the development of TGR5 modulators for the treatment and/or prevention of various diseases. The present application has identified compounds that modulate TGR5 as well as methods of using these compounds to treat or prevent diseases in which TGR5 is involved.

SUMMARY

The present application relates to TGR5 modulators and their use to treat and/or prevent various diseases. In one aspect, the application relates to a compound having formula A:

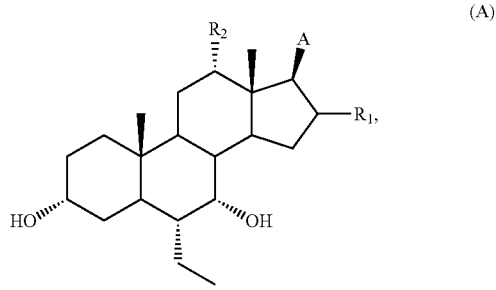

or a pharmaceutically acceptable salt, solvate, ester, tautomer, amino acid conjugate, or metabolite thereof, wherein n, $R_1$, $R_2$, and $R_3$ can be selected from the respective groups of chemical moieties later defined in the detailed description.

In another aspect, the application relates to a pharmaceutical composition comprising a compound of the application or a pharmaceutically acceptable salt, solvate, ester, tautomer, amino acid conjugate, or metabolite thereof, and at least one pharmaceutically acceptable excipient.

In yet another aspect, the application relates to a method of treating or preventing a disease or disorder in a subject, comprising administering to the subject an effective amount of a compound of the application, or a pharmaceutically acceptable salt, solvate, ester, tautomer, amino acid conjugate, or metabolite thereof.

In yet another aspect, the application relates to a compound of the application, or a pharmaceutically acceptable salt, solvate, ester, tautomer, amino acid conjugate, or metabolite thereof, for use in a method of treating or preventing a disease or disorder in a subject.

In yet another aspect, the application relates to use of a compound of the application, or a pharmaceutically acceptable salt, solvate, ester, tautomer, amino acid conjugate, or metabolite thereof, in the manufacture of a medicament for treating or preventing a disease or disorder in a subject.

In one aspect, TGR5 is involved in the disease or disorder. In one aspect, TGR5 plays a role in the activation/upregulation of the cellular pathway which results in the disease or disorder. In another aspect, TGR5 plays a role in the de-activation/downregulation of the cellular pathway which results in the disease or disorder. In a further embodiment, the disease or disorder is selected from a metabolic disease, an inflammatory disease, an autoimmune disease, a cardiac disease, a kidney disease, a gastrointestinal disease, a pulmonary disease, and a cancer.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the present application. In the case of conflict, the present specification, including definitions, will control. In addition, the materials, methods, and examples are illustrative only and are not intended to be limiting.

Other features and advantages of the application will be apparent from the following detailed description and claims.

DETAILED DESCRIPTION

Definitions

For convenience, certain terms used in the specification, examples and claims are collected here.

As used herein, "BA" means bile acid and bile acid derivatives. Bile acids are steroid carboxylic acids derived from cholesterol. The primary bile acids are cholic and chenodeoxycholic acids. In the body, these acids are conjugated with glycine or taurine before they are secreted into the bile.

"Alkyl" refers to saturated aliphatic groups, including straight chain alkyl groups (e.g., methyl, ethyl, propyl, butyl, pentyl, hexyl, heptyl, octyl, nonyl, decyl), branched chain alkyl groups (e.g., isopropyl, tert-butyl, isobutyl). In certain embodiments, a straight chain or branched chain alkyl has six or fewer carbon atoms in its backbone, referred to as "lower alkyl" (e.g., $C_1$-$C_6$ for straight chain meaning 1, 2, 3, 4, 5, or 6 carbon atoms, $C_3$-$C_6$ for branched chain meaning 3, 4, 5, or 6 carbon atoms). In some examples, a straight chain or branched chain alkyl has four or fewer carbon atoms in its backbone. In further examples, a straight chain or branched chain alkyl has three or fewer carbon atoms in its backbone.

The term "substituted alkyl" refers to an alkyl moiety having a substituent replace one or more hydrogen atoms on at least one carbon of the hydrocarbon backbone. Such substituents can include, for example, halogen, hydroxyl, alkoxyl, alkylcarbonyl, alkoxycarbonyl, carboxylate, aminocarbonyl, alkylaminocarbonyl, dialkylaminocarbonyl, cyano, amino, nitro, and cyano.

The term "alkoxy" or "alkoxyl" includes alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups.

The term "ester" refers to moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "unstable functionality" refers to a substitution pattern that contains a labile linkage, e.g., a functionality or bond that is susceptible to hydrolysis or cleavage under physiological conditions (e.g., aqueous solutions in the neutral pH range). Examples of unstable functionalities include acetals and ketals.

Additionally, the compounds of the present application or salts thereof, can exist in either hydrated or unhydrated (the anhydrous) form, or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

It will be noted that the structure of some of the compounds of the application include asymmetric carbon atoms. It is to be understood accordingly that the isomers arising from such asymmetry (e.g., all enantiomers and diastereomers) are included within the scope of the application, unless indicated otherwise. Such isomers can be obtained in substantially pure form by classical separation techniques and by stereochemically controlled synthesis. Enantiomers (R- and S-configurations) are named according to the system developed by R. S. Cahn, C. Ingold, and V. Prelog.

Further, the structures and other compounds discussed in this application include all atropic isomers thereof. Atropic isomers are a type of stereoisomer in which the atoms of two isomers are arranged differently in space. Atropic isomers owe their existence to a restricted rotation caused by hindrance of rotation of large groups about a central bond. Such atropic isomers typically exist as a mixture. However, as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form.

"Stable compound" and "stable structure" are meant to indicate a compound that is sufficiently robust to survive isolation to a useful degree of purity from a reaction mixture, and formulation into an efficacious therapeutic agent.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

As defined herein, the term "derivative", e.g., in the term "bile acid derivatives", refers to compounds that have a common core 4-membered ring structure, and are substituted with various groups as described herein.

As defined herein, the term "metabolite", e.g., in the term "bile acid metabolites", refers to glucuronidated and sulphated derivatives of the compounds described herein, wherein one or more glucuronic acid or sulphate moieties are linked to the bile acid compounds described herein. Glucuronic acid moieties may be linked to the bile acid compounds through glycosidic bonds with the hydroxyl groups of the bile acid compounds (e.g., 3-hydroxyl, 7-hydroxyl, 12-hydroxyl, and/or 15-hydroxyl). Sulphated derivatives of the bile acid compounds may be formed through sulfation of the hydroxyl groups (e.g., 3-hydroxyl, 7-hydroxyl, 12-hydroxyl, and/or 15-hydroxyl). Examples of bile acid metabolites include, but are not limited to, 3-O-glucuronide, 7-O-glucuronide, 12-O-glucuronide, 15-O-glucuronide, 3-O-7-O-glucuronide, 3-O-12-O-glucuronide, 3-O-15-O-glucuronide, 7-O-12-0-glucuronide, 7-O-15-O-glucuronide, 12-O-15-O-glucuronide, 3-O-7-O-12-O-glucuronide, 3-O-7-O-15-O-glucuronide, and 7-O-12-O-15-O-glucuronide, of the bile acid compounds described herein, and 3-sulphate, 7-sulphate, 12-sulphate, 15-sulphate, 3,7-bisulphate, 3,12-bisulphate, 3,15-bisulphate, 7,12-bisulphate, 7,15-bisulphate, 3,7,12-trisulphate, 3,7,15-trisulphate, 7,12,15-trisulphate, of the bile acid compounds described herein.

The term "bioisostere" refers to a compound resulting from the exchange of an atom or of a group of atoms with another, broadly similar, atom or group of atoms. The bioisosteric replacement may be physicochemically or topologically based. Examples of carboxylic acid bioisosteres include acyl sulfonimides, tetrazoles, sulfonates, and phosphonates. See, e.g., Patani and LaVoie, *Chem. Rev.* 96, 3147-3176 (1996).

As used herein, "pharmaceutically acceptable salts" refer to derivatives of the compounds of the application wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present application can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., USA, page 1445 (1990).

As used herein, the term "amino acid conjugates" refers to conjugates of the compounds of the application with any suitable amino acid. Taurine ($NH(CH_2)_2SO_3H$), glycine ($NHCH_2CO_2H$), and sarcosine ($N(CH_3)CH_2CO_2H$) are examples of amino acid conjugates. Suitable amino acid conjugates of the compounds have the added advantage of enhanced integrity in bile or intestinal fluids. Suitable amino acids are not limited to taurine, glycine, and sarcosine. The application encompasses amino acid conjugates of the compounds of the application.

Compounds of the application also include prodrugs or physiologically equivalent derivatives. A "prodrug" or "physiologically equivalent derivative" includes a precursor form of the drug which is metabolically converted in vivo to produce the active drug. The application further contemplates the use of prodrugs which are converted in vivo to the TGR5 modulating compounds used in the methods of the application (see, e.g., R. B. Silverman, 1992, *The Organic Chemistry of Drug Design and Drug Action*, Academic Press, Chap. 8). Such prodrugs can be used to alter the biodistribution (e.g., to allow compounds which would not typically cross the blood-brain barrier to cross the blood-brain barrier) or the pharmacokinetics of the TGR5 modulating compound. For example, an anionic group, e.g., a carboxylate, sulfate or sulfonate, can be esterified, e.g., with an alkyl group (e.g., a methyl group) or a phenyl group, to yield an ester. When the ester is administered to a subject, the ester is cleaved, enzymatically or non-enzymatically, reductively or hydrolytically, to reveal the anionic group. Such an ester can be cyclic, e.g., a cyclic sulfate or sulfone, or two or more anionic moieties may be esterified through a linking group. An anionic group can be esterified with moieties (e.g., acyloxymethyl esters) which are cleaved to reveal an intermediate TGR5 modulating compound which subsequently decomposes to yield the active TGR5 modulating compound. In one embodiment, the prodrug is a reduced form of a carboxylate, sulfate or sulfonate, e.g., an alcohol or thiol, which is oxidized in vivo to the TGR5 modulating compound. Furthermore, an anionic moiety can be esterified to a group which is actively transported in vivo, or which is selectively taken up by target organs.

The term "compounds of the application" refers to compounds having the formulae described herein.

The term "TGR5 modulator" means any compound that interacts with the TGR5 receptor. The intereaction is not limited to a compound acting as an antagonist, agonist, partial agonist, or inverse agonist of the TGR5 receptor. In one aspect, the compounds of the present application act as an antagonist of the TGR5 receptor. In another aspect, the compounds of the present application act as an agonist of the TGR5 receptor. In another aspect, the compounds of the present application act as a partial agonist of the TGR5 receptor. In another aspect, the compounds of the present application act as an inverse agonist of the TGR5 receptor.

The profile of a ligand, traditionally, endogenous or synthetic, is characterized by its intrinsic efficacy 'e' originally described by Furchgott in 1966. It is used to express the degree to which the different ligands produce varying biological responses while occupying the same number of receptors. Generally, the term "agonist" means a compound that enhances the activity of another molecule or receptor site. An agonist, by classical definition, whether an orthosteric, allosteric, inverse or a co-agonist has a property to bind to the receptor, alter its receptor state and result in a biological action. Consequently, agonism is defined as a property of an agonist or a ligand to produce a biological action. In contrast, an "antagonist" is essentially an agonist with high affinity to the same receptor macromolecule, but with very less or negligible intrinsic efficacy, and thus sterically prevents the biological actions of an agonist. As a property, antagonism may be functional or physiological, where an agonist has a direct competition for the receptor site in former and opposing effects via a different receptor-messenger system in the later. More specifically, a TGR5 agonist is a receptor ligand or compound that binds to TGR5 and increases the concentration of cyclic adenosine monophosphate (cAMP) by at least 20% in cells expressing the receptor. Conversely, a TGR5 antagonist would be a compound that antagonizes or blocks the activity of an agonist, thereby effecting a reduction in the concentration of cAMP.

The present application relates to compounds having TGR5 receptor modulating activity and their use to treat and/or prevent various diseases including metabolic disease, inflammatory disease, autoimmune disease, cardiac disease, kidney disease, cancer, and gastrolintestinal disease. Further, the present application relates to compounds of the formulae described herein.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A "composition" or "pharmaceutically acceptable composition" is a formulation containing a compound of the application or salt, solvate, ester, tautomer, amino acid conjugate, or metabolite thereof. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the application or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, ocular, ophthalmic, pulmonary, rectal, parenteral, transdermal, subcutaneous, intravenous, intramuscular, intraperitoneal, intranasal, and the like. Dosage forms for the topical or transdermal administration of a compound of this application include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

The term "treating", as used herein, means relieving, lessening, reducing, eliminating, modulating, or ameliorating, i.e., causing regression of the disease state or condition.

The term "preventing", as used herein means, to completely or almost completely stop a disease state or condition, from occurring in a patient or subject, especially when the patient or subject is predisposed to such or at risk of contracting a disease state or condition. Preventing can also include inhibiting, i.e., arresting the development, of a disease state or condition, and relieving or ameliorating, i.e., causing regression of the disease state or condition, for example when the disease state or condition may already be present.

The term "reducing the risk of", as used herein, means to lower the likelihood or probability of a central nervous system disease, inflammatory disease and/or metabolic disease from occurring in a patient, especially when the patient or subject is predisposed to such occurrence.

"Combination therapy" (or "co-therapy") includes the administration of a compound of the application and at least a second agent as part of a specific treatment regimen intended to provide the beneficial effect from the co-action of these therapeutic agents (i.e., the compound of the application and at least a second agent). The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present application. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A "therapeutically effective amount" of a compound of the application, or a combination of compounds is an amount (quantity or concentration) of compound or compounds. In one embodiment, when a therapeutically effective amount of a compound is administered to a subject in need of treatment symptoms arising from the disease are ameliorated immediately or after administration of the compound one or more times. The amount of the compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

The term "prophylactically effective amount" means an amount (quantity or concentration) of a compound of the present application, or a combination of compounds, that is administered to prevent or reduce the risk of a disease—in other words, an amount needed to provide a preventative or prophylactic effect. The amount of the present compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

The term "flash dose" refers to compound formulations that are rapidly dispersing dosage forms.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Typically, the subject is human.

Compounds and Compositions

In one aspect, the application relates to a compound of formula A:

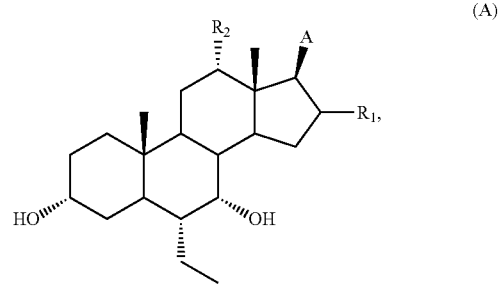

(A)

or a pharmaceutically acceptable salt, solvate, ester, tautomer, amino acid conjugate, or metabolite thereof, wherein:
A is

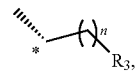

oxadiazolonyl, or isoxazolonyl, wherein the carbon atom marked with "*" is bonded to the carbon atom to which A is bonded;
n is 0, 1, or 2;
$R_1$ is H or OH;
$R_2$ is H or OH;
$R_3$ is $CR_{11}R_{12}C(O)OH$, $C(O)NHR_{31}$, tetrazolyl, oxadiazolyl, oxadiazolonyl, or thiazolidine-dionyl optionally substituted with $NHS(O)_2$—$(C_1-C_3)$ alkyl;

$R_{11}$ and $R_{12}$ are each independently H, F, OH, CH$_2$OH, or CH$_2$F, provided that $R_{11}$ and $R_{12}$ are not both H;
$R_{31}$ is OH, (CH$_2$)$_p$OH, or (CH$_2$)$_p$OSO$_3$H; and
p is 1 or 2.
(1) For example, n is 0.
(2) For example, n is 1 or 2. For example, n is 1. For example, n is 2.
(3) For example, $R_1$ and $R_2$ are each H.
(4) For example, $R_1$ is H, and $R_2$ is OH.
(5) For example, $R_2$ is H, and $R_1$ is OH.
(6) For example, $R_2$ is H, and $R_1$ is α-OH.
(7) For example, $R_2$ is H, and $R_1$ is β-OH.
(8) For example, $R_1$ and $R_2$ are each OH.
(9) For example, $R_1$ is α-OH, and $R_2$ is OH.
(10) For example, $R_1$ is β-OH, and $R_2$ is OH.
(11) For example, $R_3$ is CR$_{11}$R$_{12}$C(O)OH.
(I1) For example, $R_{11}$ is H, and $R_{12}$ is F, OH, CH$_2$OH, or CH$_2$F.
(I2) For example, $R_{11}$ is H, and $R_{12}$ is α-F, α-OH, α-CH$_2$OH, or α-CH$_2$F.
(I3) For example, $R_{11}$ is H, and $R_{12}$ is β-F, β-OH, β-CH$_2$OH, or β-CH$_2$F.
(I4) For example, $R_{11}$ is F, and $R_{12}$ is F, CH$_2$OH, or CH$_2$F.
(I5) For example, $R_{11}$ is F, and $R_{12}$ is F.
(I6) For example, $R_{11}$ is F, and $R_{12}$ is CH$_2$OH or CH$_2$F.
(I7) For example, $R_{11}$ is F, and $R_{12}$ is α-CH$_2$OH or α-CH$_2$F.
(I8) For example, $R_{11}$ is F, and $R_{12}$ is β-CH$_2$OH or β-CH$_2$F.
(I9) For example, $R_{11}$ is OH, and $R_{12}$ is CH$_2$OH or CH$_2$F.
(I10) For example, $R_{11}$ is OH, and $R_{12}$ is α-CH$_2$OH or α-CH$_2$F.
(I11) For example, $R_{11}$ is OH, and $R_{12}$ is β-CH$_2$OH or β-CH$_2$F.
(I12) For example, $R_{11}$ is CH$_2$OH, and $R_{12}$ is CH$_2$OH or CH$_2$F.
(I13) For example, $R_{11}$ is CH$_2$OH, and $R_{12}$ is CH$_2$OH.
(I14) For example, $R_{11}$ is CH$_2$OH, and $R_{12}$ is CH$_2$F.
(I15) For example, $R_{11}$ is CH$_2$OH, and $R_{12}$ is α-CH$_2$F.
(I16) For example, $R_{11}$ is CH$_2$OH, and $R_{12}$ is β-CH$_2$F.
(I17) For example, $R_{11}$ is CH$_2$F, and $R_{12}$ is CH$_2$F.
(12) For example, $R_3$ is tetrazolyl, oxadiazolyl, oxadiazolonyl, or thiazolidine-dionyl optionally substituted with NHS(O)$_2$—(C$_1$-C$_3$) alkyl. For example, $R_3$ is tetrazolyl, 1,3,4-oxadiazolyl, 1,2,4-oxadiazolonyl, or thiazolidine-2,4-dionyl substituted with NHS(O)$_2$CH$_3$.
(13) For example, $R_3$ is C(O)NHR$_{31}$.
(III1) For example, $R_{31}$ is OH.
(III2) For example, $R_{31}$ is (CH$_2$)$_p$OH.
(III3) For example, $R_{31}$ is (CH$_2$)$_2$OH
(III4) For example, $R_{31}$ is (CH$_2$)$_p$OSO$_3$H.
(III5) For example, $R_{31}$ is (CH$_2$)$_2$SO$_3$H.
(III6) For example, p is 1.
(III7) For example, p is 2.
(14) For example, A is

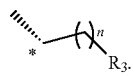

(15) For example, A is oxadiazolonyl or isoxazolonyl. For example, A is 1,2,4-oxadiazolonyl or isoxazolonyl.
For example, each of the substituents defined for one of A, n, p, $R_1$, $R_2$, $R_3$, $R_{11}$, $R_{12}$, and $R_{31}$, can be combined with any of the substituents defined for the others of A, n, p, $R_1$, $R_2$, $R_3$, $R_{11}$, $R_{12}$, and $R_{31}$.

(16) For example, n is 0, $R_3$ is CR$_{11}$R$_{12}$C(O)OH, and $R_{11}$ and $R_{12}$ are each as defined in any of (I1)-(I17).
(17) For example, n is 1, $R_3$ is CR$_{11}$R$_{12}$C(O)OH, and $R_{11}$ and $R_{12}$ are each as defined in any of (I1)-(I17).
(18) For example, n is 1 or 2, and $R_3$ is a tetrazolyl, oxadiazolyl, oxadiazolonyl, or thiazolidine-dionyl optionally substituted with NHS(O)$_2$—(C$_1$-C$_3$) alkyl.
(19) For example, n is 0, and $R_3$ is oxadiazolonyl.
(20) For example, n is 1, $R_3$ is C(O)NHR$_{31}$, and $R_{31}$ is as defined in any of (III1)-(III5).

For example, the compound of formula A is a compound of formula I:

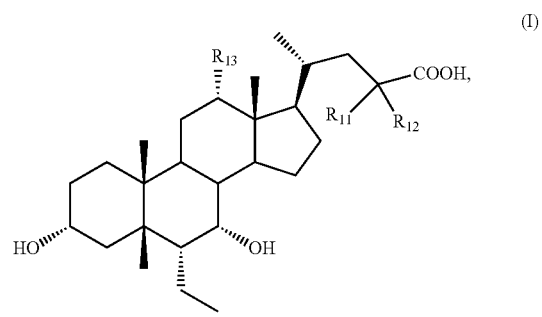

or a pharmaceutically acceptable salt, solvate, ester, tautomer, amino acid conjugate, or metabolite thereof, wherein:
$R_{11}$ and $R_{12}$ are each independently H, F, OH, CH$_2$OH, or CH$_2$F, provided that $R_{11}$ and $R_{12}$ are not both H; and
$R_{13}$ is H or OH.
(I1) For example, $R_{11}$ is H, and $R_{12}$ is F, OH, CH$_2$OH, or CH$_2$F.
(I2) For example, $R_{11}$ is H, and $R_{12}$ is α-F, α-OH, α-CH$_2$OH, or α-CH$_2$F.
(I3) For example, $R_{11}$ is H, and $R_{12}$ is β-F, β-OH, β-CH$_2$OH, or β-CH$_2$F.
(I4) For example, $R_{11}$ is F, and $R_{12}$ is F, CH$_2$OH, or CH$_2$F.
(I5) For example, $R_{11}$ is F, and $R_{12}$ is F.
(I6) For example, $R_{11}$ is F, and $R_{12}$ is CH$_2$OH or CH$_2$F.
(I7) For example, $R_{11}$ is F, and $R_{12}$ is α-CH$_2$OH or α-CH$_2$F.
(I8) For example, $R_{11}$ is F, and $R_{12}$ is β-CH$_2$OH or β-CH$_2$F.
(I9) For example, $R_{11}$ is OH, and $R_{12}$ is CH$_2$OH or CH$_2$F.
(I10) For example, $R_{11}$ is OH, and $R_{12}$ is α-CH$_2$OH or α-CH$_2$F.
(I11) For example, $R_{11}$ is OH, and $R_{12}$ is β-CH$_2$OH or β-CH$_2$F.
(I12) For example, $R_{11}$ is CH$_2$OH, and $R_{12}$ is CH$_2$OH or CH$_2$F.
(I13) For example, $R_{11}$ is CH$_2$OH, and $R_{12}$ is CH$_2$OH.
(I14) For example, $R_{11}$ is CH$_2$OH, and $R_{12}$ is CH$_2$F.
(I15) For example, $R_{11}$ is CH$_2$OH, and $R_{12}$ is α-CH$_2$F.
(I16) For example, $R_{11}$ is CH$_2$OH, and $R_{12}$ is β-CH$_2$F.
(I17) For example, $R_{11}$ is CH$_2$F, and $R_{12}$ is CH$_2$F.
(I18) For example, $R_{13}$ is H.
(I19) For example, $R_{13}$ is OH.
For example, each of the substituents defined for one of $R_{11}$, $R_{12}$, and $R_{13}$, can be combined with any of the substituents defined for the other two of $R_{11}$, $R_{12}$, and $R_{13}$.

(I20) For example, $R_{13}$ is H, and $R_{11}$ and $R_{12}$ are each as defined in any of (I1)-(I17).

(I21) For example, $R_{13}$ is OH, and $R_{11}$ and $R_{12}$ are each as defined in any of (I1)-(I17).

For example, the compound of formula A is a compound of formula II:

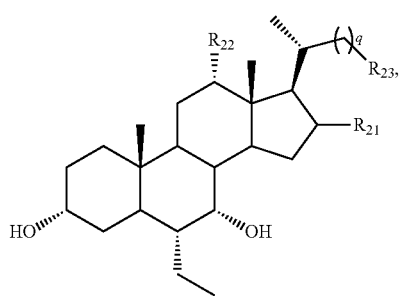

(II)

or a pharmaceutically acceptable salt, solvate, ester, tautomer, amino acid conjugate, or metabolite thereof, wherein:

q is 0, 1, or 2;

$R_{21}$ and $R_{22}$ are each independently H or OH; and $R_{23}$ is tetrazolyl, oxadiazolyl, oxadiazolonyl, or thiazolidine-dionyl optionally substituted with $NHS(O)_2$—$(C_1-C_3)$ alkyl.

(II1) For example, q is 0.

(II2) For example, q is 1.

(II3) For example, q is 2.

(II4) For example, $R_{21}$ and $R_{22}$ are each H.

(II5) For example, $R_{21}$ is H, and $R_{22}$ is OH.

(II6) For example, $R_{22}$ is H, and $R_{21}$ is OH.

(II7) For example, $R_{22}$ is H, and $R_{21}$ is α-OH.

(II8) For example, $R_{22}$ is H, and $R_{21}$ is β-OH.

(II9) For example, $R_{21}$ and $R_{22}$ are each OH.

(II10) For example, $R_{22}$ is OH, and $R_{21}$ is α-OH.

(II11) For example, $R_{22}$ is OH, and $R_{21}$ is β-OH.

(II12) For example, $R_{23}$ is tetrazolyl, oxadiazolyl, oxadiazolonyl, or thiazolidine-dionyl optionally substituted with $NHS(O)_2$—$(C_1-C_3)$ alkyl. For example, $R_{23}$ is tetrazolyl, 1,3,4-oxadiazolyl, 1,2,4-oxadiazolonyl, or thiazolidine-2,4-dionyl substituted with $NHS(O)_2CH_3$.

For example, each of the substituents defined for one of q, $R_{21}$, $R_{22}$, and $R_{23}$, can be combined with any of the substituents defined for the other three of q, $R_{21}$, $R_{22}$, and $R_{23}$.

(II13) q is 0, and $R_{21}$ and $R_{22}$ are each as defined in any of (II4)-(II11), and $R_{23}$ is as defined in (II12).

(II14) For example, q is 0, $R_{21}$ is H, $R_{22}$ is H, and $R_{23}$ is oxadiazolonyl.

(II15) For example, q is 0, $R_{21}$ is H, $R_{22}$ is OH, and $R_{23}$ is oxadiazolonyl.

(II16) For example, q is 1, and $R_{21}$ and $R_{22}$ are each as defined in any of (II4)-(II11), and $R_{23}$ is as defined in (II12).

(II17) For example, q is 1, $R_{21}$ is H, $R_{22}$ is H, and $R_{23}$ is tetrazolyl, oxadiazolyl, oxadiazolonyl, or thiazolidine-dionyl optionally substituted with $NHS(O)_2$—$(C_1-C_3)$ alkyl.

(II18) For example, q is 1, $R_{21}$ is H, $R_{22}$ is OH, and $R_{23}$ is tetrazolyl, oxadiazolyl, oxadiazolonyl, or thiazolidine-dionyl optionally substituted with $NHS(O)_2$—$(C_1-C_3)$ alkyl.

(II19) For example, q is 2, and $R_{21}$ and $R_{22}$ are each as defined in any of (II4)-(II11), and $R_{23}$ is as defined in (II12).

(II20) For example, q is 2, $R_{21}$ is H, $R_{22}$ is H, and $R_{23}$ is tetrazolyl, oxadiazolyl, oxadiazolonyl, or thiazolidine-dionyl optionally substituted with $NHS(O)_2$—$(C_1-C_3)$ alkyl.

(II21) For example, q is 2, $R_{21}$ is OH, $R_{22}$ is H, and $R_{23}$ is tetrazolyl, oxadiazolyl, oxadiazolonyl, or thiazolidine-dionyl optionally substituted with $NHS(O)_2$—$(C_1-C_3)$ alkyl.

(II22) For example, q is 2, $R_{21}$ is H, $R_{22}$ is OH, and $R_{23}$ is tetrazolyl, oxadiazolyl, oxadiazolonyl, or thiazolidine-dionyl optionally substituted with $NHS(O)_2$—$(C_1-C_3)$ alkyl.

(II23) For example, q is 2, $R_{21}$ is OH, $R_{22}$ is OH, and $R_{23}$ is tetrazolyl, oxadiazolyl, oxadiazolonyl, or thiazolidine-dionyl optionally substituted with $NHS(O)_2$—$(C_1-C_3)$ alkyl.

For example, the compound of formula A is a compound of formula III:

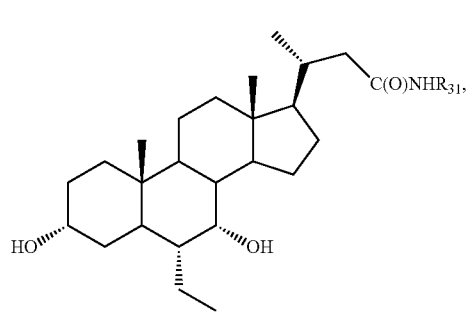

(III)

or a pharmaceutically acceptable salt, solvate, ester, tautomer, amino acid conjugate, or metabolite thereof, wherein:

$R_{31}$ is OH, $(CH_2)_pOH$, or $(CH_2)_pOSO_3H$; and p is 1 or 2.

(III1) For example, p is 1.

(III2) For example, p is 2.

(III3) For example, $R_{31}$ is OH.

(III4) For example, $R_{31}$ is $(CH_2)_pOH$.

(III5) For example, $R_{31}$ is $(CH_2)_2OH$.

(III6) For example, $R_{31}$ is $(CH_2)_pOSO_3H$.

(III7) For example, $R_{31}$ is $(CH_2)_2OSO_3H$.

For example, each of the substituents defined for one of p and $R_{31}$ can be combined with any of the substituents defined for the other of p and $R_{31}$.

(III17) For example, p is 1, and $R_{31}$ is as defined in (III3)-(III7).

(III18) For example, p is 2, and $R_{31}$ is as defined in (III3)-(III7).

Representative compounds of the application are listed in Table 1.
TABLE 1
| Cmpd No. | Chemical Structure |
|---|---|
| 1 | 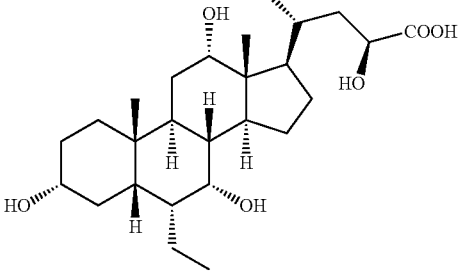 |
| 2 | 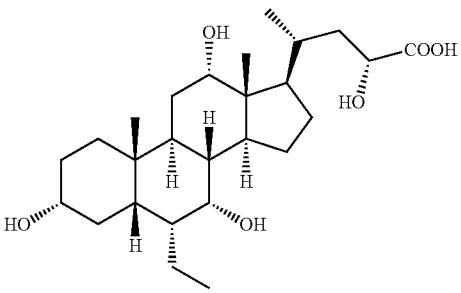 |
| 3 | 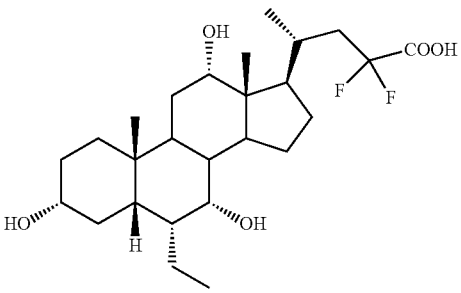 [SMILES: CC[C@H]1[C@@H](O)C2C3CC[C@H]([C@H](C)CC(F)(F)C(=O)O)[C@@]3(C)[C@@H](O)CC2[C@@]2(C)CC[C@@H](O)C[C@@H]12] |
| 4 | 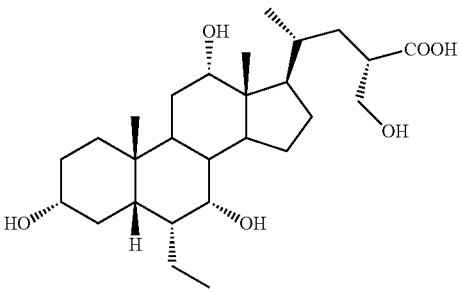 [SMILES: CC[C@H]1[C@@H](O)C2C3CC[C@H]([C@H](C)C[C@@H](CO)C(=O)O)[C@@]3(C)[C@@H](O)CC2[C@@]2(C)CC[C@@H](O)C[C@@H]12] |
| 5 | 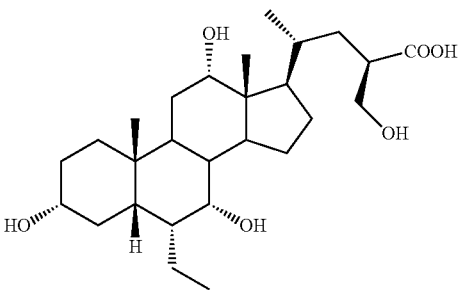 [SMILES: CC[C@H]1[C@@H](O)C2C3CC[C@H]([C@H](C)C[C@H](CO)C(=O)O)[C@@]3(C)[C@@H](O)CC2[C@@]2(C)CC[C@@H](O)C[C@@H]12] |

TABLE 1-continued

| Cmpd No. | Chemical Structure |
|---|---|
| 6 | 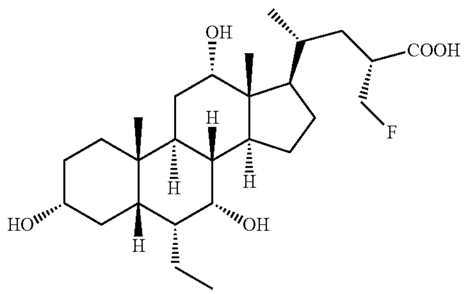 |
| 7 | 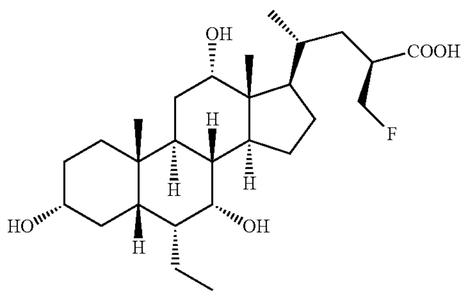 |
| 8 | 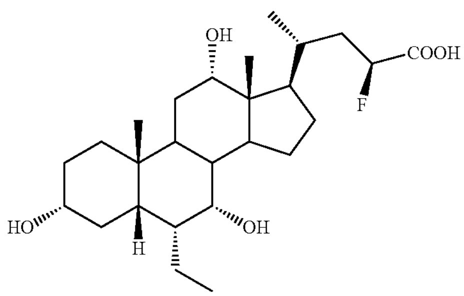 [SMILES: CC[C@H]1[C@@H](O)C2C3CC[C@H]([C@H](C)C[C@H](F)C(=O)O)[C@@]3(C)[C@@H](O)CC2[C@@]2(C)CC[C@@H](O)C[C@@H]12] |
| 9 | 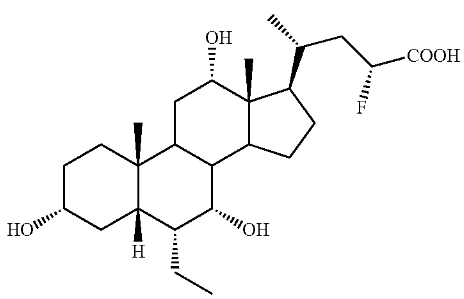 [SMILES: CC[C@H]1[C@@H](O)C2C3CC[C@H]([C@H](C)C[C@@H](F)C(=O)O)[C@@]3(C)[C@@H](O)CC2[C@@]2(C)CC[C@@H](O)C[C@@H]12] |
| 10 | 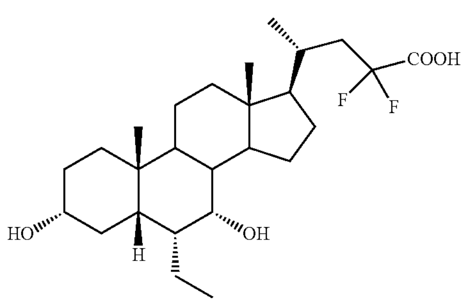 [SMILES: CC[C@H]1[C@@H](O)C2C3CC[C@H]([C@H](C)CC(F)(F)C(=O)O)[C@@]3(C)CCC2[C@@]2(C)CC[C@@H](O)C[C@@H]12] |

TABLE 1-continued

| Cmpd No. | Chemical Structure |
|----------|-------------------|
| 11 | 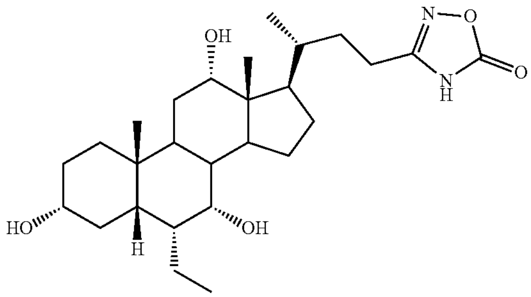 [SMILES: CC[C@H]1[C@@H](O)C2C3CC[C@H]([C@H](C)CCc4noc(=O)[nH]4)[C@@]3(C)[C@@H](O)CC2[C@@]2(C)CC[C@@H](O)C[C@@H]12] |
| 12 | 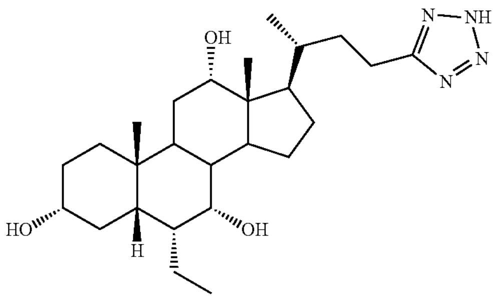 [SMILES: CC[C@H]1[C@@H](O)C2C3CC[C@H]([C@H](C)CCc4nn[nH]n4)[C@@]3(C)[C@@H](O)CC2[C@@]2(C)CC[C@@H](O)C[C@@H]12] |
| 13 | 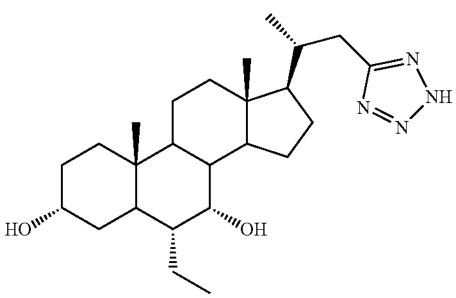 [SMILES: CC[C@@H]1C2C[C@H](O)CC[C@]2(C)C2CC[C@@]3(C)C(CC[C@@H]3[C@H](C)Cc3nn[nH]n3)C2[C@@H]1O] |
| 14 | 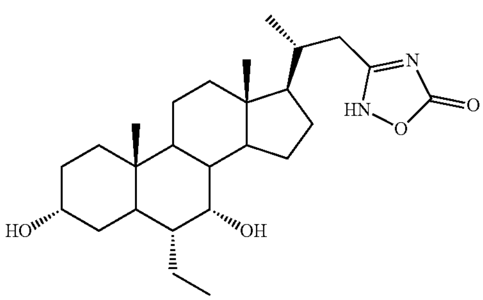 [SMILES: CC[C@@H]1C2C[C@H](O)CC[C@]2(C)C2CC[C@@]3(C)C(CC[C@@H]3[C@H](C)Cc3nc(=O)o[nH]3)C2[C@@H]1O] |
| 15 | 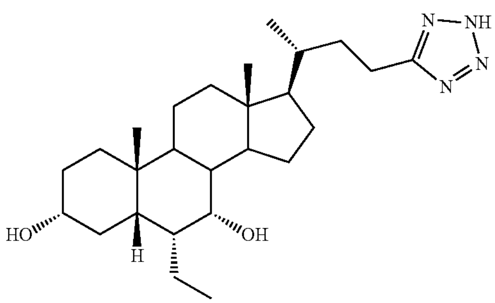 [SMILES: CC[C@H]1[C@@H](O)C2C3CC[C@H]([C@H](C)CCc4nn[nH]n4)[C@@]3(C)CCC2[C@@]2(C)CC[C@@H](O)C[C@@H]12] |

TABLE 1-continued

| Cmpd No. | Chemical Structure |
|---|---|
| 16 | 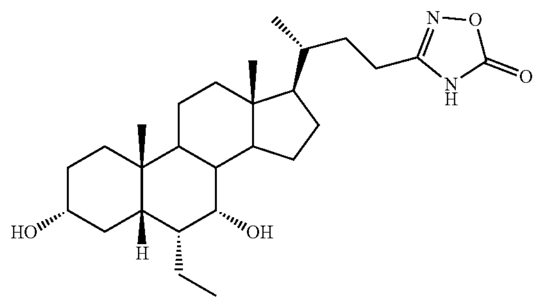 [SMILES: CC[C@H]1[C@@H](O)C2C3CC[C@H]([C@H](C)CCc4noc(=O)[nH]4)[C@@]3(C)CCC2[C@@]2(C)CC[C@@H](O)C[C@@H]12] |
| 17 | 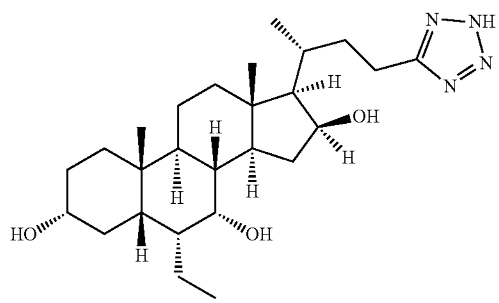 |
| 18 | 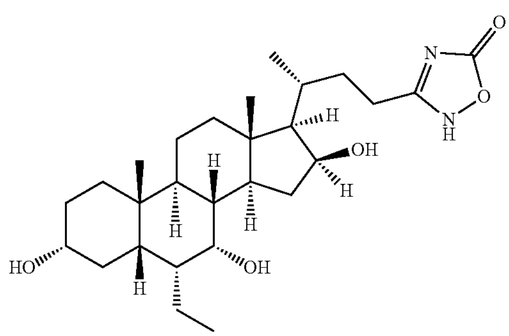 |
| 19 | 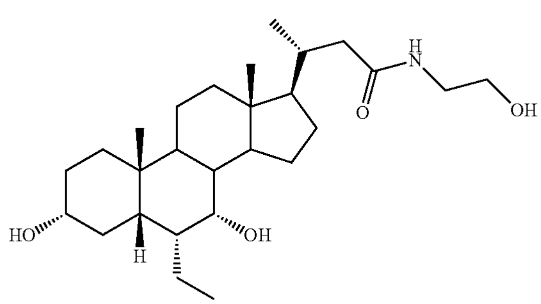 [SMILES: CC[C@H]1[C@@H](O)C2C3CC[C@H]([C@H](C)CC(=O)NCCO)[C@@]3(C)CCC2[C@@]2(C)CC[C@@H](O)C[C@@H]12] |
| 20 | 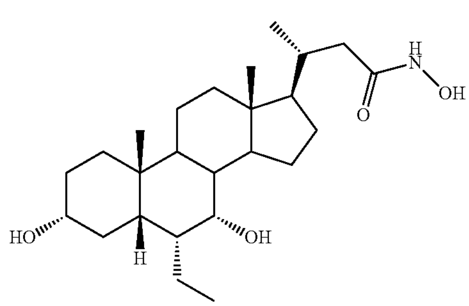 [SMILES: CC[C@H]1[C@@H](O)C2C3CC[C@H]([C@H](C)CC(=O)NO)[C@@]3(C)CCC2[C@@]2(C)CC[C@@H](O)C[C@@H]12] |

TABLE 1-continued
| Cmpd No. | Chemical Structure |
|---|---|
| 21 | 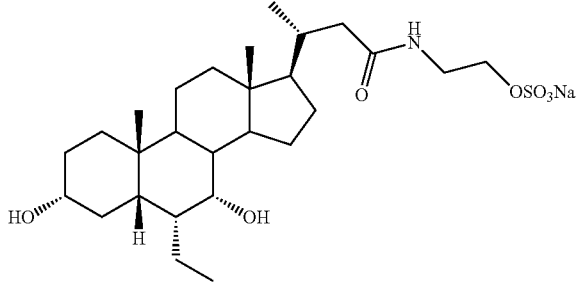 |
| 22 | 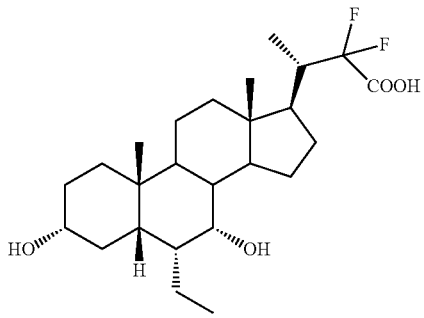 [SMILES: CC[C@H]1[C@@H](O)C2C3CC[C@H]([C@H](C)C(F)(F)C(=O)O)[C@@]3(C)CCC2[C@@]2(C)CC[C@@H](O)C[C@@H]12] |
| 23 | 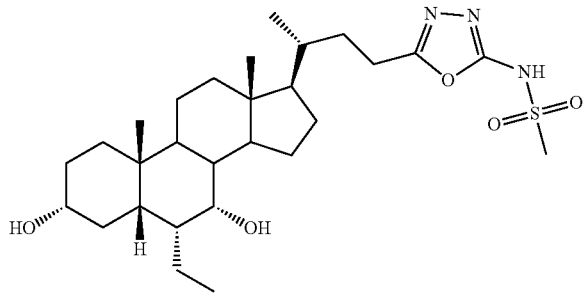 [SMILES: CC[C@H]1[C@@H](O)C2C3CC[C@H]([C@H](C)CCc4nnc(NS(C)(=O)=O)o4)[C@@]3(C)CCC2[C@@]2(C)CC[C@@H](O)C[C@@H]12] |
| 24 | 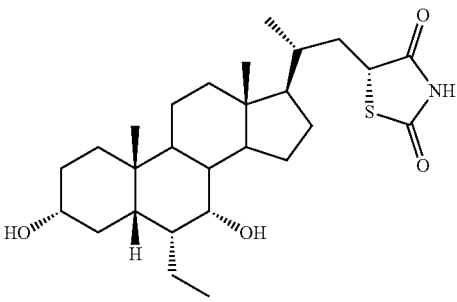 [SMILES: CC[C@H]1[C@@H](O)C2C3CC[C@H]([C@H](C)C[C@H]4SC(=O)NC4=O)[C@@]3(C)CCC2[C@@]2(C)CC[C@@H](O)C[C@@H]12] |
| 25 | 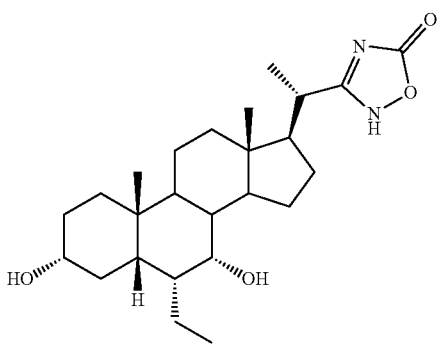 [SMILES: CC[C@H]1[C@@H](O)C2C3CC[C@H]([C@H](C)c4nc(=O)o[nH]4)[C@@]3(C)CCC2[C@@]2(C)CC[C@@H](O)C[C@@H]12] |

TABLE 1-continued

| Cmpd No. | Chemical Structure |
| --- | --- |
| 26 | 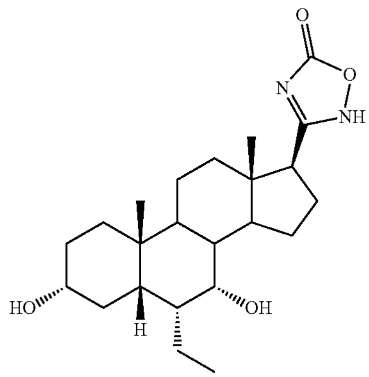 [SMILES: CC[C@H]1[C@@H](O)C2C3CC[C@H](c4nc(=O)o[nH]4)[C@@]3(C)CCC2[C@@]2(C)CC[C@@H](O)C[C@@H]12] |
| 27 | 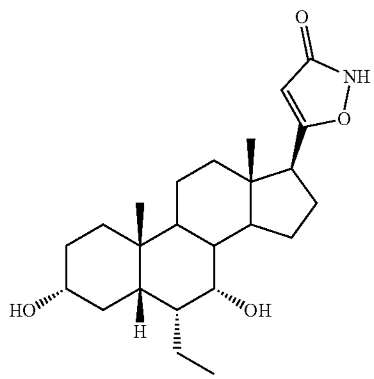 [SMILES: CC[C@H]1[C@@H](O)C2C3CC[C@H](c4cc(=O)[nH]o4)[C@@]3(C)CCC2[C@@]2(C)CC[C@@H](O)C[C@@H]12] |

In one aspect, the application includes a compound of the application, wherein the compound is a pharmaceutically acceptable salt.

One aspect of the application includes a composition comprising a compound of the application or a pharmaceutically acceptable salt, solvate, ester, tautomer, amino acid conjugate, or metabolite thereof, and at least one pharmaceutically acceptable excipient.

Synthesis of the Compounds of the Application

The present application provides methods for the synthesis of the compounds of each of the formulae described herein. The present application also provides detailed methods for the synthesis of various disclosed compounds of the present application according to the following schemes as shown in the examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the application remains operable. Moreover, two or more steps or actions can be conducted simultaneously.

The synthetic processes of the application can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5th edition, John Wiley & Sons: New York, 2001; and Greene, T. W., Wuts, P. G. M., *Protective Groups in Organic Synthesis,* 3rd edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application.

Compounds of the present application can be conveniently prepared by a variety of methods familiar to those skilled in the art. The compounds each of the formulae described herein may be prepared according to the following procedures from commercially available starting materials or starting materials which can be prepared using literature procedures. These procedures show the preparation of representative compounds of this application.

All the abbreviations used in this application are found in *Protective Groups in Organic Synthesis* by John Wiley & Sons, Inc, or the MERCK INDEX by MERCK & Co., Inc, or other chemistry books or chemicals catalogs by chemicals vendor such as Aldrich, or according to usage know in the art.

Use and Methods

The application includes the use of a compound or a pharmaceutically acceptable salt, solvate, ester, tautomer, amino acid conjugate, or metabolite, in the manufacture of a medicament for a treating or preventing disease in a subject. The application also includes a method of treating or preventing disease in a subject by administering to the subject a compound of the application or a pharmaceutically acceptable salt, solvate, ester, tautomer, amino acid conjugate, or metabolite.

One aspect of the application includes the use or method, wherein the disease is a disease in which TGR5 is involved, i.e., a "TGR5-mediated disease". In one embodiment, the TGR5-mediated disease is selected from metabolic disease, inflammatory disease, autoimmune disease, cardiac disease, kidney disease, cancer, and gastrointestinal disease in which TGR5 is involved.

In one aspect, the metabolic disease is selected from obesity, diabetes (and complications arising from diabetes, such as diabetic nephropathy, diabetic neuropathy, diabetic retinopathy, etc.), diabesity, metabolic syndrome, insulin resistance, including pre-diabetic insulin resistance, hypertension, and dyslipidemia. In one aspect, the metabolic disease is obesity. In another aspect, the metabolic disease is diabetes. In one aspect, diabetes is selected from pre-diabetes and type II diabetes. In one aspect, the metabolic disease is metabolic syndrome. In one aspect, the metabolic disease is insulin resistance. In one aspect, the metabolic disease is dyslipidemia. In one aspect, the metabolic disease is diabesity. The term "diabesity" refers to a condition wherein the subject has both diabetes and excessive weight.

In one aspect, the inflammatory disease is selected from allergy, osteoarthritis (OA), chronic obstructive pulmonary disease (COPD), appendicitis, bronchial asthma, pancreatitis, allergic rash, and psoriasis.

In one aspect, the autoimmune disease is selected from rheumatoid arthritis, multiple sclerosis, and type I diabetes. In one aspect, the autoimmune disease is erythematosus.

In one aspect, the cardiac disease is selected from congestive heart failure, myocardial infarction, atherosclerosis, angina pectoris, arteriosclerosis and cerebrovascular disease (hemorrhage, stroke, cerebrovascular infarction).

In one aspect, the kidney disease is selected from diabetic nephropathy, chronic renal failure, glomerular nephritis, hypertensive nephrosclerosis, chronic glomerulonephritis, chronic transplant glomerulopathy, chronic interstitial nephritis, and polysystic kidney disease.

In one aspect, the gastrointestinal disease is selected from inflammatory bowel disease (Crohn's disease, ulcerative colitis), short bowel syndrome (post-radiation colitis), microscopic colitis, irritable bowel syndrome (malabsorption), and bacterial overgrowth.

In one aspect, the cancer is selected from colorectal cancer, liver cancer, hepatocellular carcinoma, cholangio carcinoma, renal cancer, gastric cancer, pancreatic cancer, prostate cancer, and insulanoma.

In one aspect, the application includes a use or method, wherein the compound of the application is a TGR5 agonist.

In one aspect, the application includes a use or method, wherein the compound or composition is administered to the subject orally, ocularly, ophthalmically, parentally, intravenously, or topically. In one aspect, the subject is human.

The application includes a use or method comprising administering to a subject a therapeutically effective amount of the compound of the application. The application also includes a use or method comprising administering to a subject a prophylatically effective amount of the compound of the application.

The compounds and compositions of the present application can be administered by various routes, e.g., oral, subcutaneous, intramuscular, intravenous, or intraperitoneal. The preferred routes of administration are oral, subcutaneous, and intravenous at daily doses of about 0.01-5000 mg, preferably 5-500 mg, of the compound of the application for a 70 kg adult human per day. The appropriate dose may be administered in a single daily dose or as divided doses presented at appropriate intervals, for example as two, three, four, or more subdoses per day.

For preparing pharmaceutical compositions containing a compound of the application, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., a compound of the application. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of the compound of the application. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound with encapsulating material as a carrier providing a capsule in which the compound of the application (with or without other carriers) is surrounded by the carrier, such that the carrier is in association with the compound. In a similar manner, cachets can also be included. Tablets, powders, cachets, and capsules can be used as solid dosage forms suitable for oral administration.

Liquid pharmaceutical compositions include, for example, solutions suitable for oral, ocular, ophthalmic, or parenteral administration, suspensions, and emulsions suitable for oral administration. Sterile water solutions of the active component or sterile solutions of the active component in solvent comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., a compound of the application) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 and 8.

The pharmaceutical compositions containing compounds of the application can be administered for prophylactic and/or therapeutic treatments. In therapeutic applications, compositions are administered in an amount sufficient to cure, reverse, or at least partially slow or arrest the symptoms of the disease and its complications. An amount adequate to cure, reverse, or at least partially slow or arrest the symptom of the disease and its complications is defined as a "therapeutically effective dose". In prophylatic applications, compositions are administered in an amount sufficient to prevent the symptoms of the disease and its complications. An amount adequate to prevent the symptom of the disease and its complications is defined as a "prophylactically effective dose".

Amounts effective for therapeutic use will depend on the severity of the disease or condition and the weight and general state of the patient, but generally range from about 0.1 mg to about 2,000 mg of the compound per day for a 70 kg patient, with dosages of from about 5 mg to about 500 mg of the compound per day for a 70 kg patient being more commonly used.

In prophylactic applications, pharmaceutical compositions containing compounds of the application are administered to a patient susceptible to or otherwise at risk of developing disease, in an amount sufficient to delay or prevent the onset of the disease symptoms. In this use, the precise amounts of the compound again depend on the patient's state of health and weight, but generally range from about 0.1 mg to about 2,000 mg for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of a compound of the application sufficient to effectively treat or prevent disease in the patient.

The application also provides kits for preventing or treating disease according to the use and method of the present application. In one aspect, the application includes kit for treating or preventing disease in a subject, wherein the kit comprises a compound of the application or a salt, solvate, ester, tautomer, amino acid conjugate, or metabolite thereof. The kits typically include a pharmaceutical composition that contains an effective amount of a compound of the application, as well as informational material containing instructions of how to dispense the pharmaceutical composition, including description of the type of patients who may be treated, the schedule (e.g., dose and frequency) and route of administration, and the like.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The application having now been described by way of written description, those of skill in the art will recognize that the application can be practiced in a variety of embodiments and that the foregoing description and examples below are for purposes of illustration and not limitation of the claims that follow.

EXAMPLES

Example 1: Synthesis of Compound 1

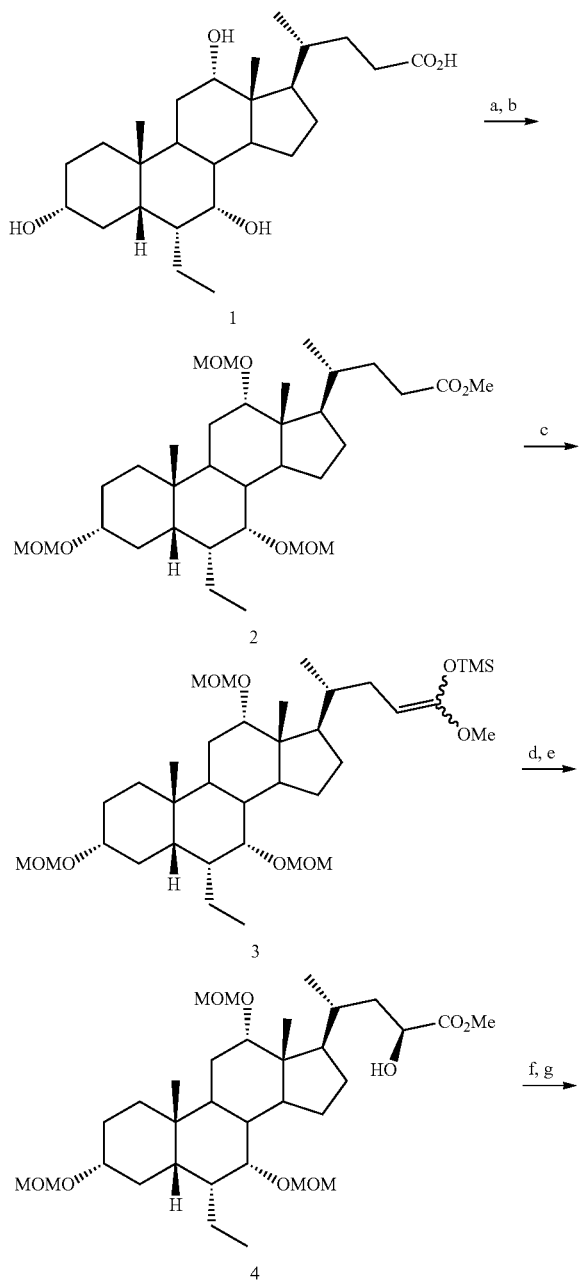

-continued

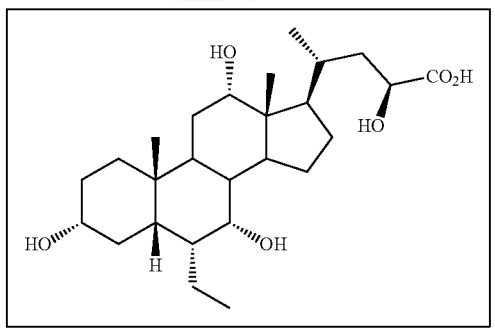

Reagents and conditions: a) pTSA, MeOH, us; b) MOMCl, DIPEA, DMAP, $CH_2Cl_2$, reflux; c) LDA, TMSCl, THF, -78° C.; d) Pb(OAc)$_4$, $CH_2Cl_2$; e) $K_2CO_3$, MeOH; f) HCl, MeOH, 45° C.; g) NaOH, MeOH, 45° C.

Methyl 3α,7α,12α-trimethoxymethoxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluenesulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with saturated $NaHCO_3$ (200 mL), $H_2O$ (200 mL) and brine (200 mL). The organic layer was dried over $Na_2SO_4$ anhydrous and concentrated under reduced pressure. The residue was then dissolved in $CH_2Cl_2$ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with $H_2O$ (100 mL), HCl 3 N (100 mL), $H_2O$ (100 mL), saturated $NaHCO_3$ (100 mL) and brine (100 mL).

The organic layer was dried over $Na_2SO_4$ anhydrous and concentrated under reduced pressure to afford 26.61 g (45.65 mmol) of 2 as a pale yellow oil (quantitative yield).

(E+Z)-3α,7α,12α-Trimethoxymethoxy-6α-ethyl-24,24-trimethylsilyloxy-methoxy-5β-chol-23-ene (3)

To a stirred solution of diisopropylamine (11.7 mL, 82.5 mmol) in distilled THF (40 mL) under $N_2$ atmosphere and cooled at −40° C., nBuLi 2.5 M in hexane (32.0 mL, 79.3 mmol) was added dropwise. After 15', the solution was cooled up to −78° C. and chlorotrimethylsilane (12.7 mL, 84.5 mmol) was added dropwise. After additional 15', a solution of 3 (6.0 g, 10.30 mmol) in distilled THF (20 mL) was added portionwise in about 20' maintaining the internal temperature not over −70° C. Once the addition was completed, the reaction mixture was stirred at −78° C. for 1 hr and then warmed at room temperature. Volatiles were removed under reduced pressure, and the residue was suspended in petroleum ether (80 mL) and filtered under vacuum. The liquor was concentrated under reduced pressure, to give 10.12 g of oil residue that was used for the next step without further purification.

Methyl 3α,7α,12α-trimethoxymethoxy-6α-ethyl-23(S)-hydroxy-5β-cholan-24-oate (4)

To a suspension of freshly crystallized and acetic acid free lead(IV)tetraacetate (6.85 g, 15.46 mmol) in distilled $CH_2Cl_2$ (50 mL) under $N_2$ atmosphere, a solution of 3 (10.12 g) in $CH_2Cl_2$ (30 mL) was added dropwise. After 30' the reaction mixture was filtered under vacuum through a celite pad. The filtrate was concentrated under reduced pressure and the residue was filtered through a silica gel pad (h: 6 cm, φ: 2 cm) collecting the crude reaction mixture with petroleum ether/AcOEt (8:2, v/v). After solvent evaporation, the residue (6.50 g) was dissolved in MeOH (50 mL) and treated with potassium carbonate (2.13 g, 15.5 mmol) at room temperature for 15'. The mixture was then diluted with $CH_2Cl_2$ (50 mL) and filtered under vacuum. The filtrate was further diluted with $CH_2Cl_2$ (70 mL) and washed with brine (70 mL). The aqueous phase was extracted with $CH_2Cl_2$ (3×40 mL), and the collected organic layers were dried over $Na_2SO_4$ anhydrous and concentrated under reduced pressure. The residue was purified by medium pressure liquid chromatography and collecting the desired compound with an isocratic elution constituted by petroleum ether/AcOEt (65:35, v/v). in 19% yield.

$^1$H-NMR (CDCl$_3$, 200 MHz) δ 0.65 (3H, s, 18-CH$_3$), 0.81-0.88 (6H, m, 19-CH$_3$+CH$_2$CH$_3$), 0.99 (3H, d, J=6.4 Hz, 21-CH$_3$), 3.32-3.36 (1H, m, 3-CH), 3.33 (6H, m, 2×OCH$_2$OCH$_3$), 3.39 (3H, s, OCH$_2$OCH$_3$), 3.46 (1H, s, 7-CH), 3.74 (3H, s, CO$_2$CH$_3$), 3.76 (1H, s, 12-CH), 4.18 (1H, t, J=6.6 Hz, 23-CH), 4.51-4.72 (6H, m, 3×OCH$_2$OCH$_3$). $^{13}$C-NMR (CDCl$_3$, 50.3 MHz) δ 11.7, 12.4, 18.7, 22.8, 23.0, 23.8, 24.9, 27.3, 27.6, 27.9, 30.3, 33.5, 35.5 (×2), 40.7, 41.2, 41.8, 42.2, 45.8, 46.3, 46.7, 52.2, 54.9, 55.7, 55.9, 69.9, 77.4, 79.9, 80.0, 94.3, 95.8, 98.4, 176.0.

3α,7α,12α,23(S)-tetrahydroxy-6α-ethyl-5β-cholan-24-oic acid (Compound 1)

To a solution of 4 (0.10 g, 0.17 mmol) in MeOH (7 mL), HCl 3 N (0.60 mL, 1.80 mmol) was added, and the mixture was stirred at 45° C. for 18 hrs. Sodium hydroxide (0.10 g, 2.50 mmol) was added and the mixture was stirred at 45° C. for additional 5 hrs. MeOH was removed under reduced pressure, the residue was diluted with $H_2O$ up to 10 mL and washed with Et$_2$O (2×5 mL). The aqueous phase was acidified with HCl 3 N, extracted with CH$_3$C$_{13}$/MeOH (85:15, v/v) (5×10 mL) and concentrated under reduced pressure. The resulting residue was purified by RP-18 medium pressure liquid chromatography by using $H_2O$/MeOH (9:1→1:1, v/v) as eluent to obtain the desired compound Compound 1 in 78% yield.

rf: 0.11 (TLC: Silica Gel 60 RP-8 F$_{254}$S; eluent: $H_2O$/MeCN 60:40). $^1$H-NMR (D$_2$O, 400 MHz) δ 0.58 (3H, s, 18-CH$_3$), 0.72-0.75 (6H, m, 19-CH$_3$+CH$_2$CH$_3$), 0.90 (3H, d, J=6.0 Hz, 21-CH$_3$), 3.25-3.34 (1H, m, 3-CH), 3.62 (1H, s, 7-CH), 3.89 (1H, t, J=8.0 Hz, 23-CH), 3.93 (1H, s, 12-CH). $^{13}$C-NMR (D$_2$O, 100.6 MHz) δ 11.0, 11.9, 17.8, 21.8, 22.4, 22.8, 26.7, 27.4, 27.7, 29.1, 32.4, 33.3, 34.7, 39.7, 41.0, 41.1, 41.6, 44.8, 46.2, 47.3, 48.8, 70.4, 71.9 (×2), 73.1, 182.0.

Example 2: Synthesis of Compound 2

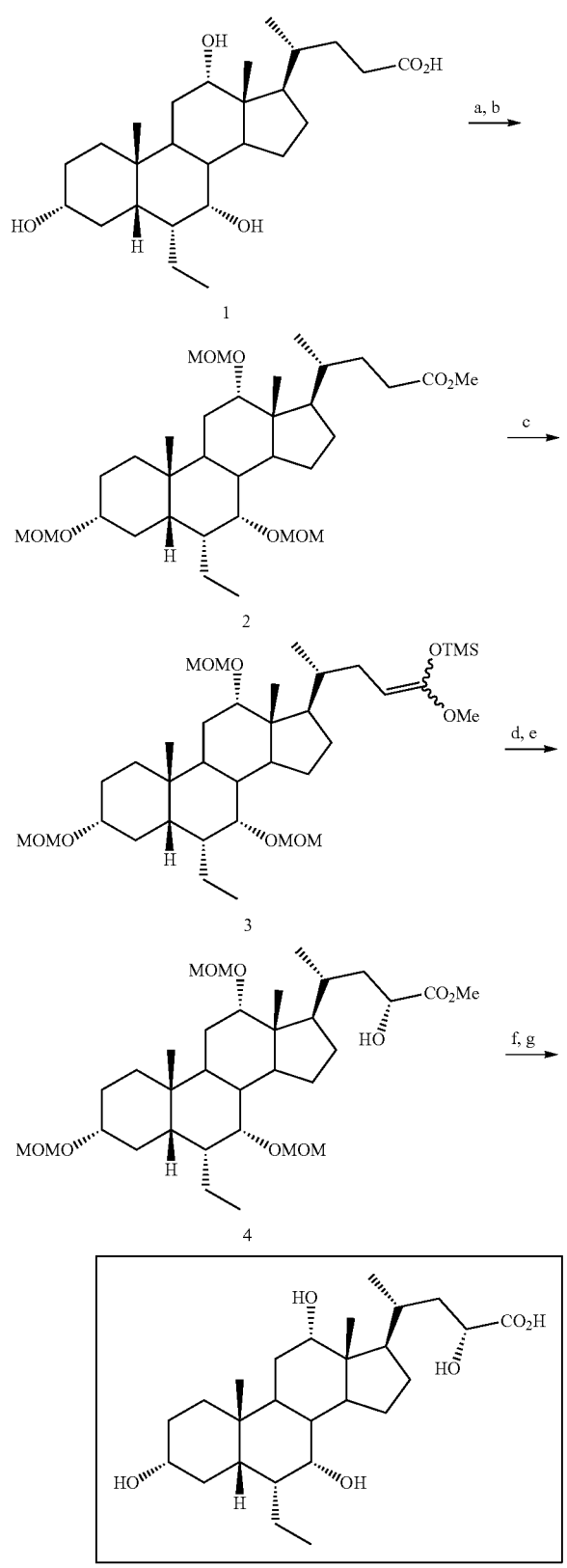

Reagents and conditions: a) pTSA, MeOH, us; b) MOMCl, DIPEA, DMAP, CH$_2$Cl$_2$, reflux; c) LDA, TMSCl, THF, -78° C.; d) Pb(OAc)$_4$, CH$_2$Cl$_2$; e) K$_2$CO$_3$, MeOH; f) HCl, MeOH, 45° C.; g) NaOH, MeOH, 45° C.

Methyl 3α,7α,12α-trimethoxymethyloxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluensulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with a saturated solution of NaHCO$_3$ (200 mL), H$_2$O (200 mL) and brine (200 mL). The organic layer was dried over Na$_2$SO$_4$ anhydrous and concentrated under reduced pressure. The residue was then dissolved in CH$_2$Cl$_2$ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with H$_2$O (100 mL), HCl 3 N (100 mL), H$_2$O (100 mL), saturated NaHCO$_3$ (100 mL) and brine (100 mL). The organic layer was dried over Na$_2$SO$_4$ anhydrous and concentrated under reduced pressure to afford 26.61 g (45.65 mmol) of 2 as a pale yellow oil (quantitative yield).

(E+Z)-3α,7α,12α-Trimethoxymethyloxy-6α-ethyl-24,24-trimetylsilyloxy-methoxy-5β-chol-23-ene (3)

To a stirred solution of diisopropylamine (11.7 mL, 82.5 mmol) in distilled THF (40 mL) under N$_2$ atmosphere and cooled at −40° C., nBuLi 2.5 M in hexane (32.0 mL, 79.3 mmol) was added dropwise. After 15', the solution was cooled up to −78° C. and chlorotrimethylsilane (12.7 mL, 84.5 mmol) was added dropwise. After additional 15', a solution of 3 (6.0 g, 10.30 mmol) in distilled THF (20 mL) was added portionwise in about 20' maintaining the internal temperature not over −70° C. Once the addition was completed, the reaction mixture was stirred at −78° C. for 1 hr and then warmed at room temperature. Volatiles were removed under reduced pressure, and the residue was suspended in petroleum ether (80 mL) and filtered under vacuum. The liquor was concentrated under reduced pressure, to give 10.12 g of oil residue that was used for the next step without further purification.

Methyl 3α,7α,12α-trimethoxymethyloxy-6α-ethyl-23(R)-hydroxy-5β-cholan-24-oate (4)

To a suspension of freshly crystallized and acetic acid free lead(IV)tetraacetate (6.85 g, 15.46 mmol) in distilled CH$_2$Cl$_2$ (50 mL) under N$_2$ atmosphere, a solution of 3 (10.12 g) in CH$_2$Cl$_2$ (30 mL) was added dropwise. After 30' the reaction mixture was filtered under vacuum through a celite pad. The filtrate was concentrated under reduced pressure and the residue was filtered through a silica gel pad (h: 6 cm, φ: 2 cm) collecting the crude reaction mixture with petroleum ether/AcOEt (8:2, v/v). After solvent evaporation, the residue (6.50 g) was dissolved in MeOH (50 mL) and treated with potassium carbonate (2.13 g, 15.5 mmol) at room temperature for 15'. The mixture was then diluted with CH$_2$Cl$_2$ (50 mL) and filtered under vacuum. The filtrate was further diluted with CH$_2$Cl$_2$ (70 mL) and washed with brine (70 mL). The aqueous phase was extracted with CH$_2$Cl$_2$ (3×40 mL), and the collected organic layers were dried over Na$_2$SO$_4$ anhydrous and concentrated under reduced pressure. The residue was purified by medium pressure liquid chromatography and collecting the desired compound with an isocratic elution constituted by petroleum ether/AcOEt (65:35, v/v), to obtain 4 in 20% yield.

$^1$H NMR (CDCl$_3$, 200 MHz) δ 0.69 (3H, s, 18-CH$_3$), 0.83-0.90 (6H, m, 19-CH$_3$+CH$_2$CH$_3$), 1.01 (3H, d, J=6.3 Hz, 21-CH$_3$), 3.24-3.35 (1H, m, 3-CH), 3.34 (6H, m, 2×OCH$_2$OCH$_3$), 3.42 (3H, s, OCH$_2$OCH$_3$), 3.48 (1H, s, 7-CH), 3.76 (3H, s, CO$_2$CH$_3$), 3.81 (1H, s, 12-CH), 4.20 (1H, dd, J$_1$=1.9 Hz, J$_{2=6.0}$ Hz 23-CH), 4.56-4.74 (6H, m, 3×OCH$_2$OCH$_3$). $^{13}$C-NMR $^1$H NMR (CDCl$_3$, 50.3 MHz) δ 11.8, 12.5, 17.2, 28.8, 23.0, 23.8, 24.9, 27.4, 27.6, 27.8, 30.3, 32.4, 35.5 (×2), 40.7, 41.0, 41.9, 42.3, 45.8, 46.4, 46.5, 52.4, 54.9, 55.7, 55.9, 68.0, 77.4, 80.0, 81.0, 94.3, 95.9, 98.4, 176.5.

3α,7α,12α,23(R)-tetrahydroxy-6α-ethyl-5β-cholan-24-oic acid (Compound 2)

To a solution of 4a or 4b (0.10 g, 0.17 mmol) in MeOH (7 mL), HCl 3 N (0.60 mL, 1.80 mmol) was added, and the mixture was stirred at 45° C. for 18 hrs. Sodium hydroxide (0.10 g, 2.50 mmol) was added and the mixture was stirred at 45° C. for additional 5 hrs. MeOH was removed under reduced pressure, the residue was diluted with H$_2$O up to 10 mL and washed with Et$_2$O (2×5 mL). The aqueous phase was acidified with HCl 3 N, extracted with CH$_3$C$_{13}$/MeOH (85:15, v/v) (5×10 mL) and concentrated under reduced pressure. The resulting residue was purified by RP-18 medium pressure liquid chromatography by using H$_2$O/MeOH (9:1→1:1, v/v) as eluent to obtain the desired compound Compound 2 in 71% yield.

rf: 0.10 (TLC: Silica Gel 60 RP-8 F$_{254}$S; eluent: H$_2$O/MeCN 60:40). $^1$H-NMR (D$_2$O, 400 MHz) δ 0.66 (3H, s, 18-CH$_3$), 0.78-0.86 (6H, m, 19-CH$_3$+CH$_2$CH$_3$), 0.96 (3H, pss, 21-CH$_3$), 1.96-2.00 (1H, m, 22-CH$_2$), 3.30-3.37 (1H, m, 3-CH), 3.66 (1H, s, 7-CH), 3.95 (1H, m, 23-CH), 4.01 (1H, s, 12-CH). $^{13}$C-NMR (D$_2$O, 100.6 MHz) δ 11.2, 12.2, 16.1, 21.9, 22.6, 22.8, 26.8, 27.3, 27.9, 29.1, 32.4, 34.8, 35.2, 39.9, 40.8, 41.3, 41.7, 45.0, 46.3 (×2), 47.3, 69.9, 70.4, 71.8, 73.0, 182.7.

Example 3: Synthesis of Compound 3

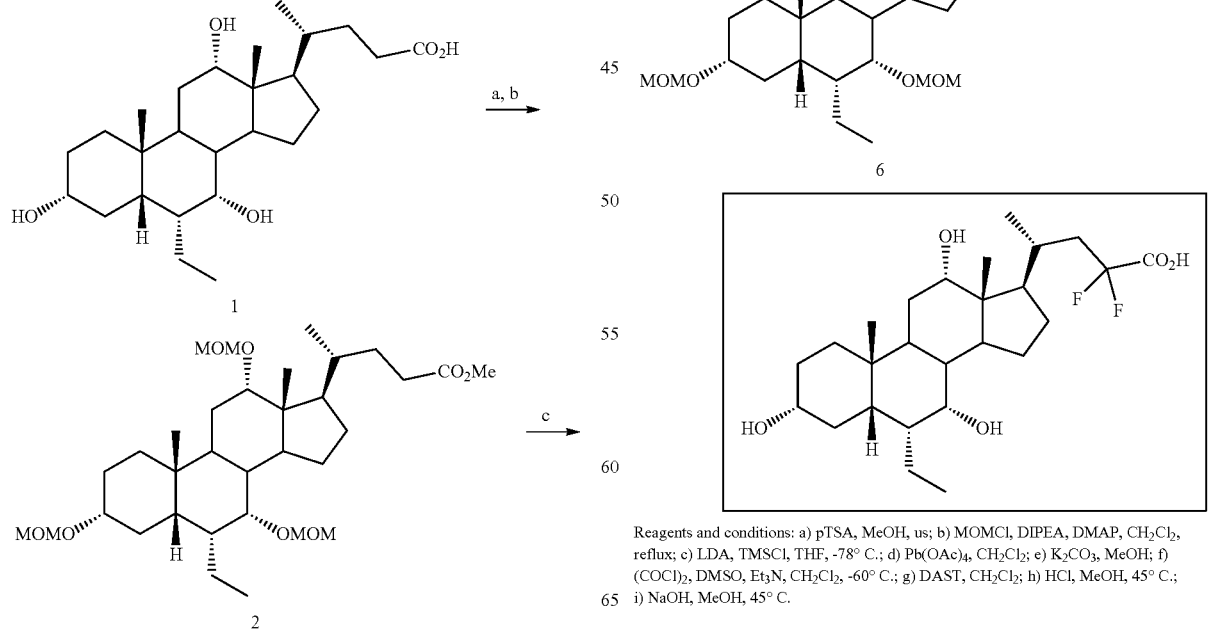

Reagents and conditions: a) pTSA, MeOH, us; b) MOMCl, DIPEA, DMAP, CH$_2$Cl$_2$, reflux; c) LDA, TMSCl, THF, -78° C.; d) Pb(OAc)$_4$, CH$_2$Cl$_2$; e) K$_2$CO$_3$, MeOH; f) (COCl)$_2$, DMSO, Et$_3$N, CH$_2$Cl$_2$, -60° C.; g) DAST, CH$_2$Cl$_2$; h) HCl, MeOH, 45° C.; i) NaOH, MeOH, 45° C.

Methyl 3α,7α,12α-trimethoxymethyloxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluensulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with a saturated solution of $NaHCO_3$ (200 mL), $H_2O$ (200 mL) and brine (200 mL). The organic layer was dried over $Na_2SO_4$ anhydrous and concentrated under reduced pressure. The residue was then dissolved in $CH_2Cl_2$ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with $H_2O$ (100 mL), HCl 3 N (100 mL), $H_2O$ (100 mL), saturated $NaHCO_3$ (100 mL) and brine (100 mL). The organic layer was dried over $Na_2SO_4$ anhydrous and concentrated under reduced pressure to afford 26.61 g (45.65 mmol) of 2 as a pale yellow oil (quantitative yield).

(E+Z)-3α,7α,12α-Trimethoxymethyloxy-6α-ethyl-24,24-trimetylsilyloxy-methoxy-5β-chol-23-ene (3)

To a stirred solution of diisopropylamine (11.7 mL, 82.5 mmol) in distilled THF (40 mL) under $N_2$ atmosphere and cooled at −40° C., nBuLi 2.5 M in hexane (32.0 mL, 79.3 mmol) was added dropwise. After 15', the solution was cooled up to −78° C. and chlorotrimethylsilane (12.7 mL, 84.5 mmol) was added dropwise. After additional 15', a solution of 3 (6.0 g, 10.30 mmol) in distilled THF (20 mL) was added portionwise in about 20' maintaining the internal temperature not over −70° C. Once the addition was completed, the reaction mixture was stirred at −78° C. for 1 hr and then warmed at room temperature. Volatiles were removed under reduced pressure, and the residue was suspended in petroleum ether (80 mL) and filtered under vacuum. The liquor was concentrated under reduced pressure, to give 10.12 g of oil residue that was used for the next step without further purification.

Methyl 23(R+S)-hydroxy-6α-ethyl-3α,7α,12α-trimethoxymethyloxy-5β-cholan-24-oate (4)

To a suspension of freshly crystallized and acetic acid free lead(IV)tetraacetate (6.85 g, 15.46 mmol) in distilled $CH_2Cl_2$ (50 mL) under $N_2$ atmosphere, a solution of 3 (10.12 g) in $CH_2Cl_2$ (30 mL) was added dropwise. After 30' the reaction mixture was filtered under vacuum through a celite pad. The filtrate was concentrated under reduced pressure and the residue was filtered through a silica gel pad (h: 6 cm, φ: 2 cm) collecting the crude reaction mixture with petroleum ether/AcOEt (8:2, v/v). After solvent evaporation, the residue (6.50 g) was dissolved in MeOH (50 mL) and treated with potassium carbonate (2.13 g, 15.5 mmol) at room temperature for 15'. The mixture was then diluted with $CH_2Cl_2$ (50 mL) and filtered under vacuum. The filtrate was further diluted with $CH_2Cl_2$ (70 mL) and washed with brine (70 mL). The aqueous phase was extracted with $CH_2Cl_2$ (3×40 mL), and the collected organic layers were dried over $Na_2SO_4$ anhydrous and concentrated under reduced pressure. The residue was purified by silica gel flash chromatography by using petroleum ether/AcOEt (9:1→7:3, v/v) as eluent to afford 2.53 g (4.26 mmol, 41%) of 4 as mixture of two epimers.

Methyl 23-oxo-6α-ethyl-3α,7α,12α-trimethoxymethyloxy-5β-cholan-24-oate (5)

To a solution of oxalyl chloride (4.0 mL, 46.7 mmol) in distilled $CH_2Cl_2$ (70 mL) under $N_2$ atmosphere and cooled ad −60° C., DMSO (6.60 mL, 93.4 mmol) diluted in $CH_2Cl_2$ (10 mL) was added dropwise. After 15', a solution of 4 (11.2 g, 18.7 mmol) in $CH_2Cl_2$ (70 mL) was added dropwise, and the resulting mixture was stirred at −60° C. for 1 hr. Triethylamine (26.2 mL, 186.8 mmol) was added dropwise and the mixture was slowly warmed at room temperature. The reaction mixture was treated with KOH 1 M (100 mL) for 5' and water and organic phases were separated. The aqueous phase was then extracted with $CH_2Cl_2$ (2×50 mL). The collected organic layers were dried over $Na_2SO_4$ anhydrous and concentrated under reduced pressure. The residue was purified by silica gel flash chromatography yielding pure intermediate 5 (6.82 g, 11.4 mmol, 61%) using a solution of petroleum ether/AcOEt (85:15, v/v).

Methyl 3α,7α,12α-trimethoxymethyloxy-6α-ethyl-23,23-gemdifluoro-5β-cholan-24-oate (6)

To a solution of 5 (6.82 g, 11.4 mmol) in distilled $CH_2Cl_2$ (100 mL) under $N_2$ atmosphere, diethylaminosulfurtrifluoride (15.1 mL, 114.4 mmol) was added, and the reaction was stirred at room temperature for 8 hrs. The mixture was cautiously poured in a saturated solution of $NaHCO_3$ (250 mL) placed in a water-ice bath and under magnetic stirring. Once the $CO_2$ release was completed, the two phases were separated and the organic layer was washed with $H_2O$ (100 mL), brine (100 mL), dried over $Na_2SO_4$ anhydrous and concentrated under reduced pressure. The residue was purified by silica gel flash chromatography eluting with a solution of petroleum ether/AcOEt (9:1, v/v) to collect the desired compound 6 (5.17 g, 8.4 mmol, 73%).

3α,7α,12α-Trihydroxy-6α-ethyl-23,23-gemdifluoro-5β-cholan-24-oic acid (Compound 3)

To a solution of 6 (5.17 g, 8.4 mmol) in MeOH (50 mL), HCl 3 N (25.1 mL, 75.4 mmol) was added and the mixture was stirred at 45° C. for 18 hrs. Sodium hydroxide (5.0 g, 125.6 mmol) was added and the mixture reacted at 45° C. for additional 5 hrs. MeOH was then removed under reduced pressure and the residue was diluted with $H_2O$ up to 70 mL and washed with $Et_2O$ (2×30 mL). The aqueous phase was acidified with HCl 3 N and the resulting whitish suspension was filtered through a RP-18 silica gel pad (h: 4 cm, φ: 2 cm) under vacuum, washing with $H_2O$ (250 mL) and collecting the crude compound with $H_2O$/MeCN (1:1, v/v). Once the solvent was removed under reduced pressure, the residue was purified by RP-18 medium pressure liquid chromatography by using $H_2O$/MeCN as eluent (8:2→6:4, v/v) to afford 3.59 g of pure Compound 3 (91%).

rf: 0.65 (TLC: Silica Gel 60 RP-8 $F_{254}S$; eluent: $H_2O$/MeCN 50:50). $^1$H-NMR (DMSO-d6, 400 MHz) δ 0.61 (3H, s, 18-$CH_3$), 0.80-0.86 (6H, m, 19-$CH_3$+$CH_2CH_3$), 0.93 (3H, d, J=6.3 Hz, 21-$CH_3$), 3.30-3.36 (1H, m, 3-CH), 3.48 (1H, s, 7-CH), 3.78 (1H, s, 12-CH), 3.78 (1H, s, OH), 3.97 (1H, s, OH), 4.17-4.21 (1H, bs, OH). $^{13}$C-NMR (DMSO-d6, 100.6 MHz) δ 11.7, 12.1, 18.4, 22.18, 22.6, 22.9, 26.5, 27.4, 28.6, 30.2, 30.6, 30.8, 33.4, 34.8, 35.5, 41.2, 41.6, 45.4, 45.9, 46.4, 68.3, 70.6, 70.8, 117.2 (t, $J_{C-F}$=248.7 Hz), 165.5 (t, $J_{C-F}$=31.9 Hz). $^{19}$F-NMR (DMSO-d6, 376.5 MHz) δ −102.2 (2F, m). MS-TIC (−) m/z: 471.3.

Example 4: Synthesis of Compound 4

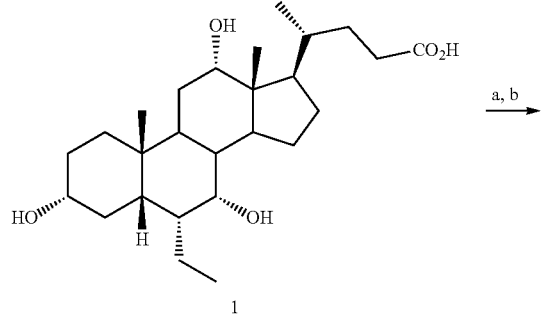

1

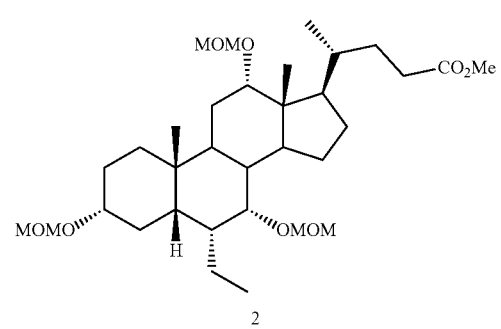

2

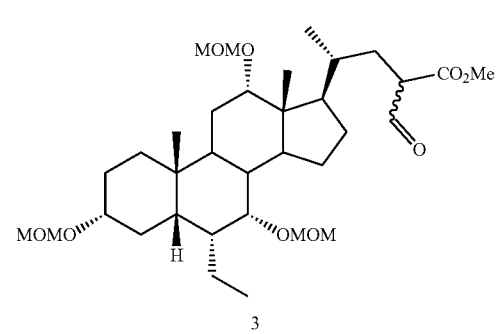

3

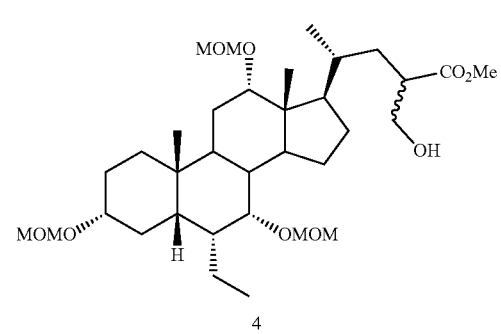

4

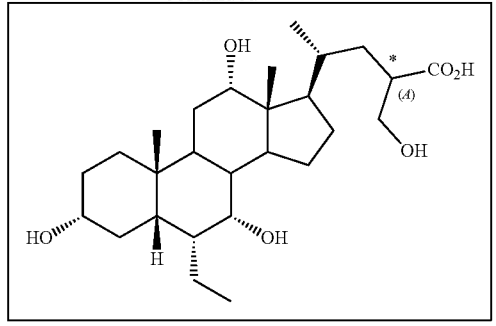

Reagents and conditions: a) pTSA, MeOH, us; b) MOMCl, DIPEA, DMAP, CH$_2$Cl$_2$, reflux; c) LDA, HCO$_2$Et, THF, −78° C.; d) NaBH$_4$, THF, H$_2$O, 0° C.; e) HCl, MeOH, 45° C.; f) NaOH, MeOH, 45° C.

Methyl 3α,7α,12α-trimethoxymethyloxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluensulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with a saturated solution of NaHCO$_3$ (200 mL), H$_2$O (200 mL) and brine (200 mL). The organic layer was dried over Na$_2$SO$_4$ anhydrous and concentrated under reduced pressure. The residue was then dissolved in CH$_2$Cl$_2$ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with H$_2$O (100 mL), HCl 3 N (100 mL), H$_2$O (100 mL), saturated NaHCO$_3$ (100 mL) and brine (100 mL). The organic layer was dried over Na$_2$SO$_4$ anhydrous and concentrated under reduced pressure to afford 26.61 g (45.65 mmol) of 2 as a pale yellow oil (quantitative yield).

Methyl 3α,7α,12α-trimethoxymethyloxy-6α-ethyl-23(A+B)-hydroxymethyl-5β-cholan-24-oate (4)

To a solution of diisopropylamine (0.87 g, 8.59 mmol) in dry THF (25 mL) at −78° C., nBuLi 2.5 M in hexane (3.1 mL, 7.73 mmol) was added dropwise. After 15', a solution of compound 2 (0.50 g, 0.86 mmol) in dry THF (10 mL) was added dropwise and the mixture was reacted at −78° C. for 15'. Ethylformate (1.27 g, 17.18 mmol) was then added and reacted for 1 hr prior the reaction was allowed to warm to room temperature. The reaction mixture was poured into H$_2$O (50 mL) and extracted with EtOAc (3×50 mL). The combined organic layers were washed with brine (100 mL), dried over Na$_2$SO$_4$ anhydrous and evaporated under reduced pressure. The intermediate 3 thus obtained was dissolved in MeOH (20 mL) and treated at 0° C. with NaBH$_4$ for 30'. The reaction was quenched with H$_2$O (50 mL) and extracted with CH$_2$Cl$_2$ (3×50 mL). The combined organic layers were washed with H$_2$O (100 mL), brine (100 mL), dried over Na$_2$SO$_4$ and evaporated under reduced pressure. The crude was purified by silica gel flash chromatography (eluting with isopropanol in CHCl$_3$ from 2 to 7%, v/v) obtaining 0.29 g of compound 4 as epimeric mixture (0.48 mmol, 56%).

3α,7α,12α-Trihydroxy-6α-ethyl-23(A)-hydroxymethyl-5β-cholan-24-oic acid (Compound 4)

To a solution of compound 4 (0.29 g, 0.48 mmol) in MeOH (15 mL) HCl 3 N (5 mL) was added and the resulting mixture was stirred at 50° C. for 48 hrs. The mixture was allowed to cool at room temperature and treated with NaOH (5% in MeOH) up to pH 14 at 45° C. for 24 hrs. The solvent was evaporated under reduced pressure, the crude was suspended in H$_2$O (30 mL) and extracted with Et$_2$O (2×10 mL). The aqueous phase was acidified with HCl 3 N and the precipitate was collected by filtration. The crude compound was purified by medium pressure liquid chromatography using a solution of H$_2$O/MeOH (MeOH from 10 to 40%). The epimer Compound 4 was obtained in 29% yield (0.065 g, 0.14 mmol).

rf: 0.39 (TLC: Silica Gel 60 RP-8 F$_{254}$S; eluent: H$_2$O/MeOH 20:80). $^1$H-NMR (CD$_3$OD, 400 MHz) δ: 0.71 (3H, s, 18-CH$_3$), 0.89-0.92 (6H, m, 19-CH$_3$+CH$_2$CH$_3$), 1.06 (3H, d, J=5.7 Hz, 21-CH$_3$), 2.55-2.62 (1H, bs, 23-CH), 3.29-3.34 (1H, m, 3-CH), 3.55-3.64 (1H, s, 7-CH), 3.64-3.67 (2H, bs, CH$_2$OH), 3.97 (1H, s, 12-CH). $^{13}$C-NMR (CD$_3$OD, 100.6 MHz) δ: 12.6, 13.8, 18.6, 24.0 (×2), 24.8, 28.8, 29.4, 30.2, 31.6, 34.9, 36.3, 36.8, 37.6, 37.8, 42.3, 43.7 (×2), 47.4, 48.2, 66.6, 71.7, 73.7, 74.6, 176.3.

Example 5: Synthesis of Compound 5

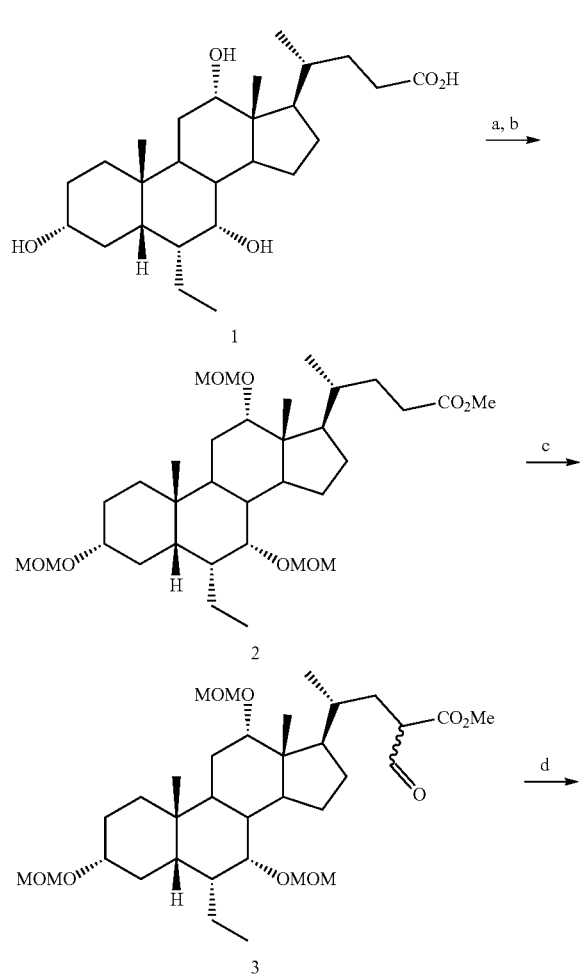

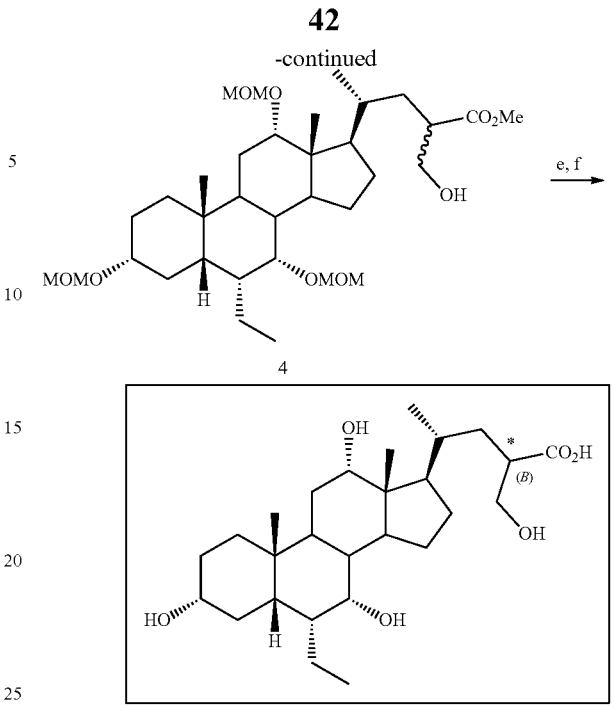

Reagents and conditions: a) pTSA, MeOH, us; b) MOMCl, DIPEA, DMAP, CH$_2$Cl$_2$, reflux; c) LDA, HCO$_2$Et, THF, -78° C.; d) NaBH$_4$, THF, H$_2$O, 0° C.; e) HCl, MeOH, 45° C.; f) NaOH, MeOH, 45° C.

Methyl 3α,7α,12α-trimethoxymethyloxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluensulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with a saturated solution of NaHCO$_3$ (200 mL), H$_2$O (200 mL) and brine (200 mL). The organic layer was dried over Na$_2$SO$_4$ anhydrous and concentrated under reduced pressure. The residue was then dissolved in CH$_2$Cl$_2$ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with H$_2$O (100 mL), HCl 3 N (100 mL), H$_2$O (100 mL), saturated NaHCO$_3$ (100 mL) and brine (100 mL). The organic layer was dried over Na$_2$SO$_4$ anhydrous and concentrated under reduced pressure to afford 26.61 g (45.65 mmol) of 2 as a pale yellow oil (quantitative yield).

Methyl 3α,7α,12α-trimethoxymethyloxy-6α-ethyl-23(A+B)-hydroxymethyl-5β-cholan-24-oate (4)

To a solution of diisopropylamine (0.87 g, 8.59 mmol) in dry THF (25 mL) at −78° C., nBuLi 2.5 M in hexane (3.1 mL, 7.73 mmol) was added dropwise. After 15', a solution of compound 2 (0.50 g, 0.86 mmol) in dry THF (10 mL) was added dropwise and the mixture was reacted at −78° C. for 15'. Ethylformate (1.27 g, 17.18 mmol) was then added and reacted for 1 hr prior the reaction was allowed to warm to room temperature. The reaction mixture was poured into H₂O (50 mL) and extracted with EtOAc (3×50 mL). The combined organic layers were washed with brine (100 mL), dried over Na₂SO₄ anhydrous and evaporated under reduced pressure. The intermediate 3 thus obtained was dissolved in MeOH (20 mL) and treated at 0° C. with NaBH₄ for 30'. The reaction was quenched with H₂O (50 mL) and extracted with CH₂Cl₂ (3×50 mL). The combined organic layers were washed with H₂O (100 mL), brine (100 mL), dried over Na₂SO₄ and evaporated under reduced pressure. The crude was purified by silica gel flash chromatography (eluting with isopropanol in CHCl₃ from 2 to 7%, v/v) obtaining 0.29 g of compound 4 as epimeric mixture (0.48 mmol, 56%).

3α,7α,12α-Trihydroxy-6α-ethyl-23(B)-hydroxymethyl-5β-cholan-24-oic acid (Compound 5)

To a solution of compound 4 (0.29 g, 0.48 mmol) in MeOH (15 mL) HCl 3 N (5 mL) was added and the resulting mixture was stirred at 50° C. for 48 hrs. The mixture was allowed to cool at room temperature and treated with NaOH (5% in MeOH) up to pH 14 at 45° C. for 24 hrs. The solvent was evaporated under reduced pressure, the crude was suspended in H₂O (30 mL) and extracted with Et₂O (2×10 mL). The aqueous phase was acidified with HCl 3 N and the precipitate was collected by filtration. The crude compound was purified by medium pressure liquid chromatography using a solution of H₂O/MeOH (MeOH from 10 to 40%). The epimer Compound 5 was obtained in 40% yield (0.09 g, 0.19 mmol).

rf: 0.36 (TLC: Silica Gel 60 RP-8 F₂₅₄S; eluent: H₂O/MeCN 20:80). ¹H-NMR (CD₃OD, 400 MHz) δ: 0.72 (3H, s, 18-CH₃), 0.89-0.92 (6H, m, 19-CH₃+CH₂CH₃), 1.065 (3H, d, J=6.0 Hz, 21-CH₃), 2.39-2.46 (1H, bs, 23-CH), 3.28-3.33 (1H, m, 3-CH), 3.61 (2H, m, CH₂OH), 3.66 (1H, s, 7-CH), 3.98 (1H, s, 12-CH). ¹³C-NMR (CD₃OD, 100.6 MHz) δ: 12.0, 13.0, 18.0, 23.5 (×2), 24.2, 28.2, 29.0, 29.6, 30.7, 31.1, 34.4, 35.8, 36.3, 36.7, 37.0, 41.8, 43.1 (×2), 47.0, 47.7, 64.4, 71.2, 73.2, 74.1, 184.5.

Example 6: Synthesis of Compound 6

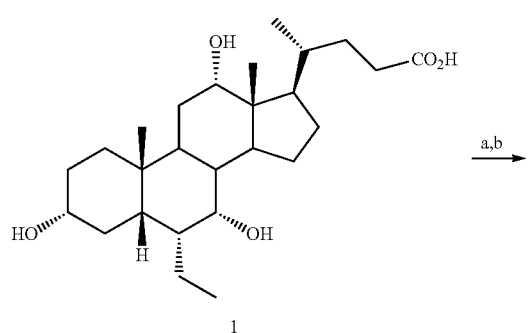

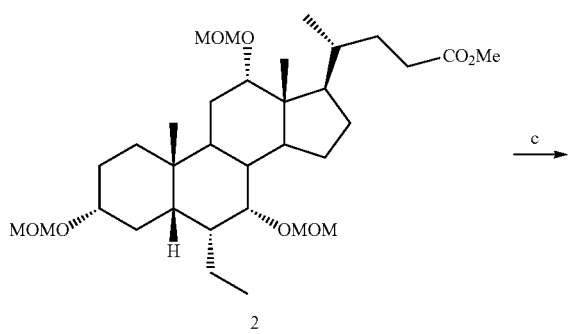

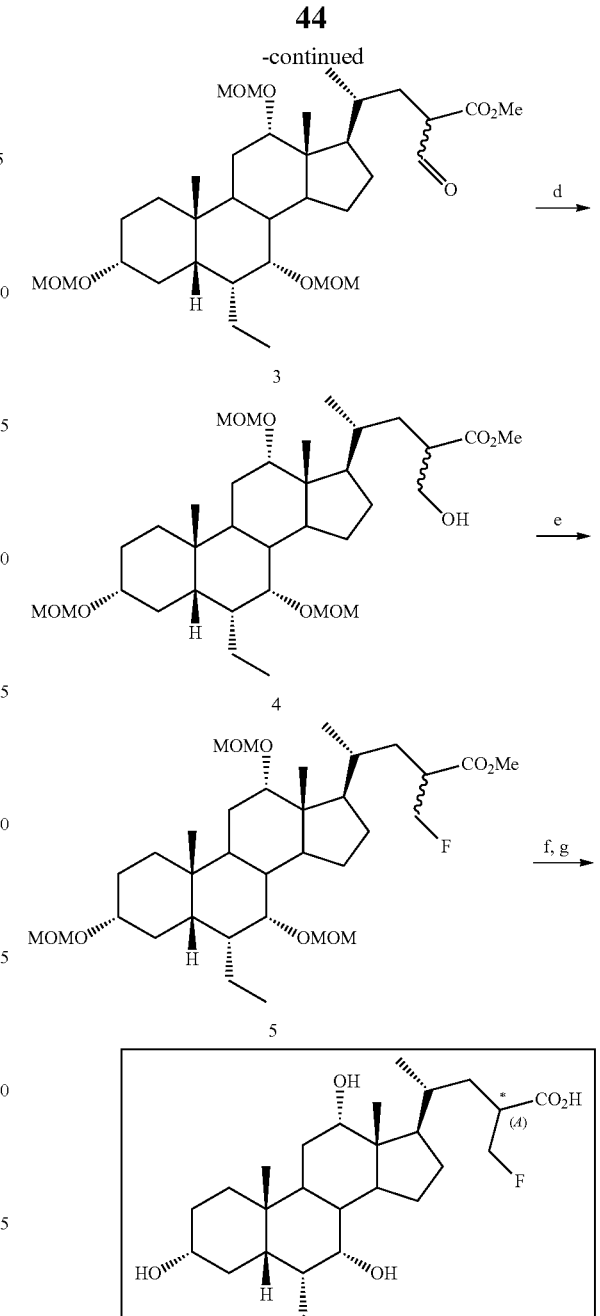

Reagents and conditions: a) pTSA, MeOH, us; b) MOMCl, DIPEA, DMAP, CH₂Cl₂, reflux; c) LDA, HCO₂Et, THF, -78° C.; d) NaBH₄, THF, H₂O, 0° C.; e) DAST, CH₂Cl₂; f) HCl, MeOH, 45° C.; g) NaOH, MeOH, 45° C.

Methyl 3α,7α,12α-trimethoxymethyloxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluensulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with a saturated solution of NaHCO₃ (200 mL), H₂O (200 mL) and brine (200 mL). The organic layer was dried over Na₂SO₄ anhydrous and concentrated under reduced pressure. The residue was then dissolved in CH$_2$Cl$_2$ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with H$_2$O (100 mL), HCl 3 N (100 mL), H$_2$O (100 mL), saturated NaHCO$_3$ (100 mL) and brine (100 mL). The organic layer was dried over Na$_2$SO$_4$ anhydrous and concentrated under reduced pressure to afford 26.61 g (45.65 mmol) of 2 as a pale yellow oil (quantitative yield).

Methyl 3α,7α,12α-trimethoxymethyloxy-6α-ethyl-23(A+B)-hydroxymethyl-5β-cholan-24-oate (4)

To a solution of diisopropylamine (0.87 g, 8.59 mmol) in dry THF (25 mL) at −78° C., nBuLi 2.5 M in hexane (3.1 mL, 7.73 mmol) was added dropwise. After 15', a solution of compound 2 (0.50 g, 0.86 mmol) in dry THF (10 mL) was added dropwise and the mixture was reacted at −78° C. for 15'. Ethylformate (1.27 g, 17.18 mmol) was then added and reacted for 1 hr prior the reaction was allowed to warm to room temperature. The reaction mixture was poured into H$_2$O (50 mL) and extracted with EtOAc (3×50 mL). The combined organic layers were washed with brine (100 mL), dried over Na$_2$SO$_4$ anhydrous and evaporated under reduced pressure. The intermediate 3 thus obtained was dissolved in MeOH (20 mL) and treated at 0° C. with NaBH$_4$ for 30'. The reaction was quenched with H$_2$O (50 mL) and extracted with CH$_2$Cl$_2$ (3×50 mL). The combined organic layers were washed with H$_2$O (100 mL), brine (100 mL), dried over Na$_2$SO$_4$ and evaporated under reduced pressure. The crude was purified by silica gel flash chromatography (eluting with isopropanol in CHCl$_3$ from 2 to 7%, v/v) obtaining 0.29 g of compound 4 as epimeric mixture (0.48 mmol, 56%).

3α,7α,12α-Trihydroxy-6α-ethyl-23(A)-fluoromethyl-fluoromethyl-5β-cholan-24-oic acid (Compound 6)

To a solution of compound 4 (0.09 g, 0.16 mmol) in dry CH$_2$Cl$_2$ (3 mL) a solution of DAST (0.04 g, 0.23 mmol) in dry CH$_2$Cl$_2$ (2 mL) was added. The mixture was reacted 2 hrs at −78° C. and subsequently poured into a saturated solution of NaHCO$_3$ (10 mL) and extracted with CH$_2$Cl$_2$ (2×15 mL). The combined organic layers were washed with H$_2$O (10 mL), brine (10 mL), dried over Na$_2$SO$_4$ anhydrous and evaporated under reduced pressure. The intermediate 5 was then dissolved in MeOH (10 mL) and treated with HCl 37% (0.3 mL) at room temperature for 12 hrs. The solvent was evaporated under reduced pressure. The residue was suspended in H$_2$O (10 mL) and extracted with CH$_2$Cl$_2$ (2×10 mL). The combined organic layers were washed with H$_2$O (10 mL), brine (10 mL), dried over Na$_2$SO$_4$ anhydrous and evaporated under reduced pressure. The crude was dissolved in 2 mL of NaOH (3% in THF) and reacted at room temperature for 4 hrs. The solvent was evaporated under reduced pressure, suspended in H$_2$O (10 mL) and extracted with CH$_2$Cl$_2$ (2×10 mL). The combined organic layers were washed with H$_2$O (10 mL), brine (10 mL), dried over Na$_2$SO$_4$ anhydrous and evaporated under reduced pressure. The crude was purified by silica gel flash chromatography eluting with a solution of MeOH/CHCl$_3$ (98:2→9:1, v/v+ 0.1% AcOH) obtaining 12 mg of pure Compound 6 (0.026 mmol, 16%).

rf: 0.29 (TLC: Silica Gel 60 RP-8 F254S; eluent: H$_2$O/MeOH 20:80). $^1$H-NMR (CD$_3$OD, 400 MHz) δ 0.73 (3H, s, 18-CH$_3$), 0.91-0.97 (6H, m, 19-CH$_3$+CH$_2$CH$_3$), 1.05 (1H, d, J=6.0, 21-CH$_3$), 2.10-2.19 (2H, m, 22-CH$_2$), 2.51-2.54 (1H, m, 23-CH), 3.41-3.45 (1H m, 3-CH), 3.53-3.57 (2H, m, CH$_2$F), 3.66 (1H, s, 7-CH), 3.97 (1H, s, 7-CH). $^{13}$C-NMR (CD$_3$OD, 100.6 MHz) δ 12.0, 13.0, 18.1, 23.4, 24.0, 28.2, 29.1, 29.7, 30.7 (×2), 31.0, 34.4, 36.0, 36.3, 36.7, 37.3, 41.7, 43.1 (×2), 46.9, 47.6, 58.9, 71.1, 73.2, 74.0, 78.4 (J$_{C-F}$=392.3 Hz), 181.5.

Example 7: Synthesis of Compound 7

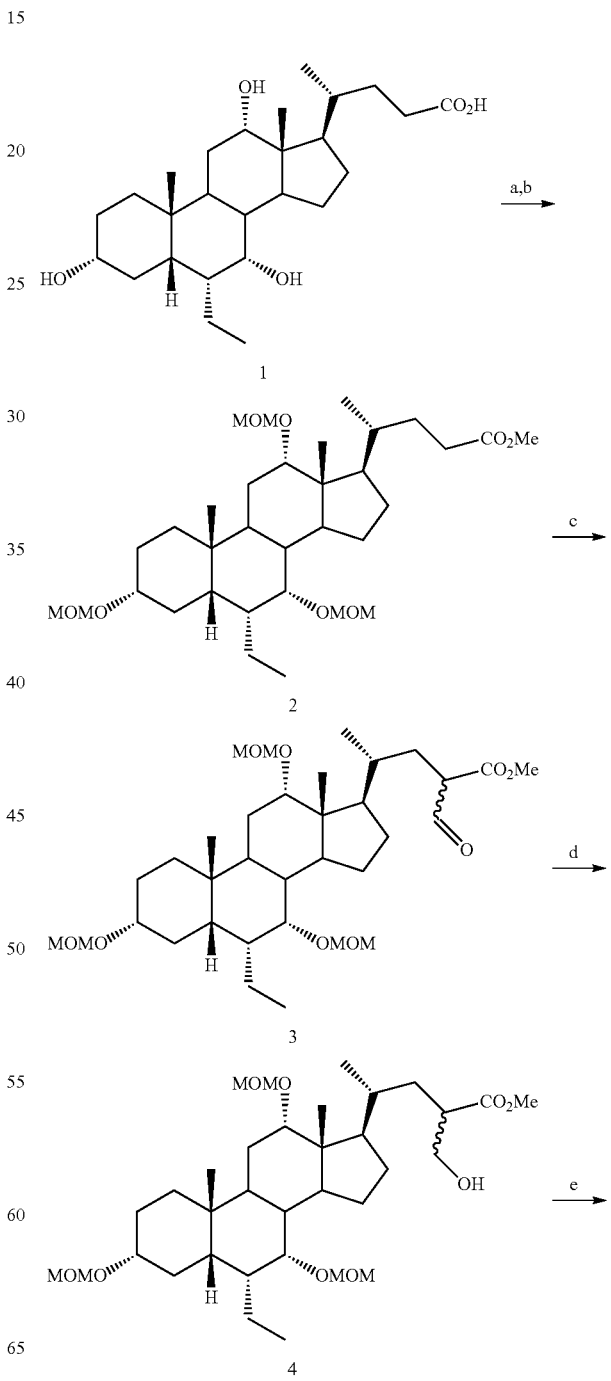

-continued

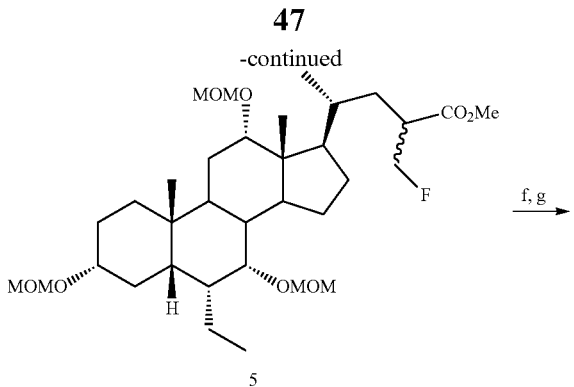

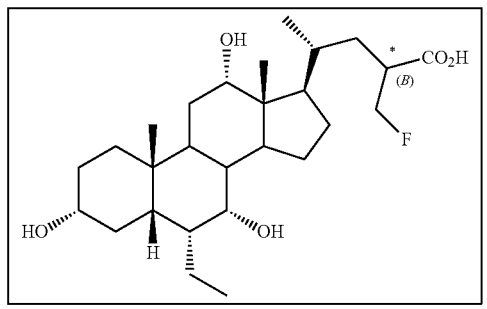

Reagents and conditions: a) pTSA, MeOH, us; b) MOMCl, DIPEA, DMAP, CH$_2$Cl$_2$, reflux; c) LDA, HCO$_2$Et, THF, -78° C.; d) NaBH$_4$, THF, H$_2$O, 0° C.; e) DAST, CH$_2$Cl$_2$; f) HCl, MeOH, 45° C.; g) NaOH, MeOH, 45° C.

Methyl 3α,7α,12α-trimethoxymethyloxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluensulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with a saturated solution of NaHCO$_3$ (200 mL), H$_2$O (200 mL) and brine (200 mL). The organic layer was dried over Na$_2$SO$_4$ anhydrous and concentrated under reduced pressure. The residue was then dissolved in CH$_2$Cl$_2$ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with H$_2$O (100 mL), HCl 3 N (100 mL), H$_2$O (100 mL), saturated NaHCO$_3$ (100 mL) and brine (100 mL). The organic layer was dried over Na$_2$SO$_4$ anhydrous and concentrated under reduced pressure to afford 26.61 g (45.65 mmol) of 2 as a pale yellow oil (quantitative yield).

Methyl 3α,7α,12α-trimethoxymethyloxy-6α-ethyl-23(A+B)-hydroxymethyl-5β-cholan-24-oate (4)

To a solution of diisopropylamine (0.87 g, 8.59 mmol) in dry THF (25 mL) at -78° C., nBuLi 2.5 M in hexane (3.1 mL, 7.73 mmol) was added dropwise. After 15', a solution of compound 2 (0.50 g, 0.86 mmol) in dry THF (10 mL) was added dropwise and the mixture was reacted at -78° C. for 15'. Ethylformate (1.27 g, 17.18 mmol) was then added and reacted for 1 hr prior the reaction was allowed to warm to room temperature. The reaction mixture was poured into H$_2$O (50 mL) and extracted with EtOAc (3×50 mL). The combined organic layers were washed with brine (100 mL), dried over Na$_2$SO$_4$ anhydrous and evaporated under reduced pressure. The intermediate 3 thus obtained was dissolved in MeOH (20 mL) and treated at 0° C. with NaBH$_4$ for 30'. The reaction was quenched with H$_2$O (50 mL) and extracted with CH$_2$Cl$_2$ (3×50 mL). The combined organic layers were washed with H$_2$O (100 mL), brine (100 mL), dried over Na$_2$SO$_4$ and evaporated under reduced pressure. The crude was purified by silica gel flash chromatography (eluting with isopropanol in CHCl$_3$ from 2 to 7%, v/v) obtaining 0.29 g of compound 4 as epimeric mixture (0.48 mmol, 56%).

3α,7α,12α-Trihydroxy-6α-ethyl-23(A)-fluoromethyl-fluoromethyl-5β-cholan-24-oic acid (Compound 7)

To a solution of compound 4 (0.09 g, 0.16 mmol) in dry CH$_2$Cl$_2$ (3 mL) a solution of DAST (0.04 g, 0.23 mmol) in dry CH$_2$Cl$_2$ (2 mL) was added. The mixture was reacted 2 hrs at -78° C. and subsequently poured into a saturated solution of NaHCO$_3$ (10 mL) and extracted with CH$_2$Cl$_2$ (2×15 mL). The combined organic layers were washed with H$_2$O (10 mL), brine (10 mL), dried over Na$_2$SO$_4$ anhydrous and evaporated under reduced pressure. The intermediate 5 was then dissolved in MeOH (10 mL) and treated with HCl 37% (0.3 mL) at room temperature for 12 hrs. The solvent was evaporated under reduced pressure. The residue was suspended in H$_2$O (10 mL) and extracted with CH$_2$Cl$_2$ (2×10 mL). The combined organic layers were washed with H$_2$O (10 mL), brine (10 mL), dried over Na$_2$SO$_4$ anhydrous and evaporated under reduced pressure. The crude was dissolved in 2 mL of NaOH (3% in THF) and reacted at room temperature for 4 hrs. The solvent was evaporated under reduced pressure, suspended in H$_2$O (10 mL) and extracted with CH$_2$Cl$_2$ (2×10 mL). The combined organic layers were washed with H$_2$O (10 mL), brine (10 mL), dried over Na$_2$SO$_4$ anhydrous and evaporated under reduced pressure. The crude was purified by silica gel flash chromatography eluting with a solution of MeOH/CHCl$_3$ (98:2→9:1, v/v+0.1% AcOH) obtaining 16 mg of pure Compound 7 (0.034 mmol, 21%).

rf: 0.27 (TLC: Silica Gel 60 RP-8 F254S; eluent: H$_2$O/MeOH 20:80). $^1$H-NMR (CD$_3$OD, 400 MHz) δ 0.72 (3H, s, 18-CH$_3$), 0.90-0.96 (6H, m, 19-CH$_3$+CH$_2$CH$_3$), 1.06 (1H, d, J=6.3 Hz, 21-CH$_3$), 2.17-2.22 (1H, m, 22-CH$_2$), 2.54-2.58 (1H, m, 23-CH), 3.28-3.33 (1H m, 3-CH), 3.38-3.58 (2H, m, CH$_2$F), 3.66 (1H, s, 7-CH), 3.97 (1H, s, 7-CH). $^{13}$C-NMR (CD$_3$OD, 100.6 MHz) δ 12.0, 13.0, 18.1, 23.5, 24.2, 28.2, 29.1, 29.7, 30.8, 31.0, 34.4, 36.0, 36.3, 36.7, 37.3, 41.7, 43.1, 46.9, 47.4, 47.6, 58.9, 71.1, 73.2, 74.0, 75.3 (J$_{C-F}$=452.7 Hz), 181.5.

Example 8: Synthesis of Compound 8

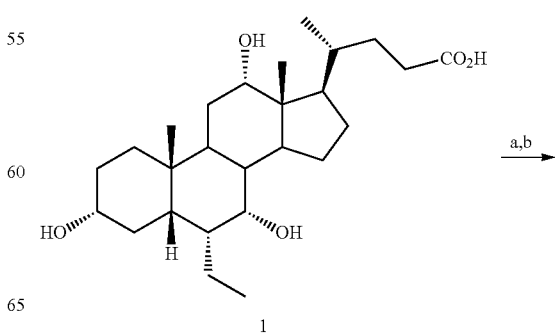

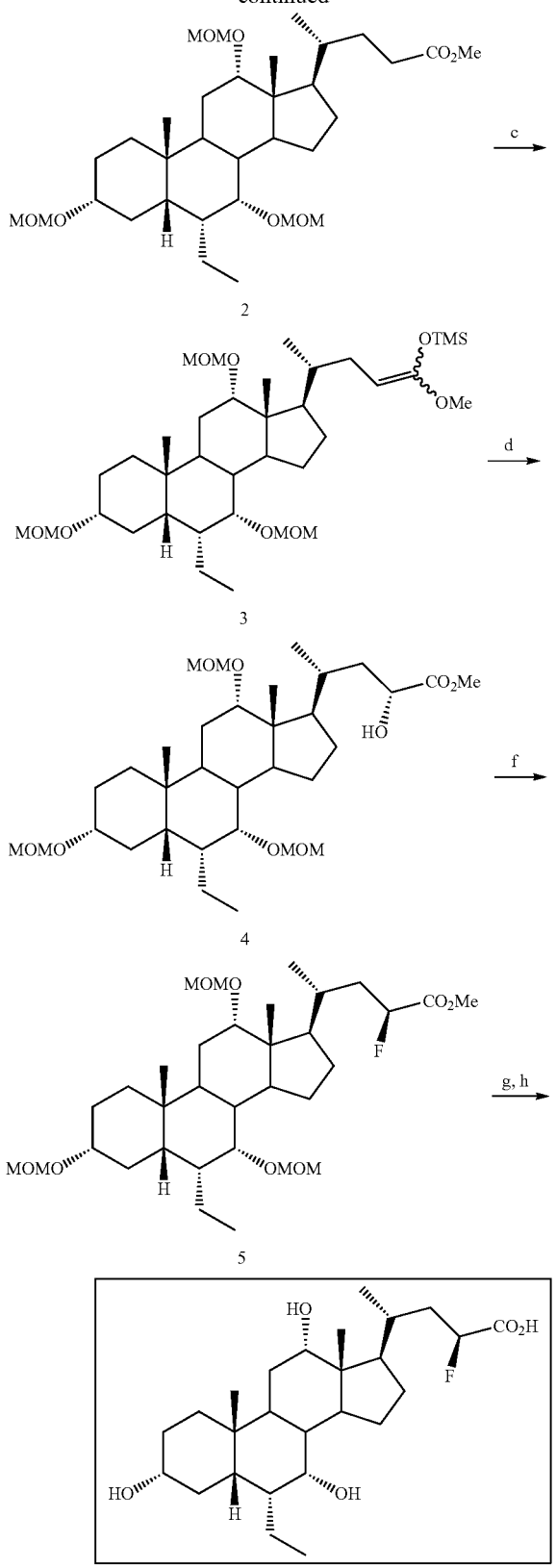

Reagents and conditions: a) pTSA, MeOH, us; b) MOMCl, DIPEA, DMAP, CH$_2$Cl$_2$, reflux; c) LDA, TMSCl, THF, -78° C.; d) Pb(OAc)$_4$, CH$_2$Cl$_2$; e) K$_2$CO$_3$, MeOH; f) DAST, CH$_2$Cl$_2$; g) HCl, MeOH, 45° C.; h) NaOH, MeOH, 45° C.

Methyl 3α,7α,12α-trimethoxymethyloxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluensulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with a saturated solution of NaHCO$_3$ (200 mL), H$_2$O (200 mL) and brine (200 mL). The organic layer was dried over Na$_2$SO$_4$ anhydrous and concentrated under reduced pressure. The residue was then dissolved in CH$_2$Cl$_2$ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with H$_2$O (100 mL), HCl 3 N (100 mL), H$_2$O (100 mL), saturated NaHCO$_3$ (100 mL) and brine (100 mL). The organic layer was dried over Na$_2$SO$_4$ anhydrous and concentrated under reduced pressure to afford 26.61 g (45.65 mmol) of 2 as a pale yellow oil (quantitative yield).

(E+Z)-3α,7α,12α-Trimethoxymethyloxy-6α-ethyl-24,24-trimetylsilyloxy-methoxy-5β-chol-23-ene (3)

To a stirred solution of diisopropylamine (11.7 mL, 82.5 mmol) in distilled THF (40 mL) under N$_2$ atmosphere and cooled at -40° C., nBuLi 2.5 M in hexane (32.0 mL, 79.3 mmol) was added dropwise. After 15', the solution was cooled up to -78° C. and chlorotrimethylsilane (12.7 mL, 84.5 mmol) was added dropwise. After additional 15', a solution of 3 (6.0 g, 10.30 mmol) in distilled THF (20 mL) was added portionwise in about 20' maintaining the internal temperature not over -70° C. Once the addition was completed, the reaction mixture was stirred at -78° C. for 1 hr and then warmed at room temperature. Volatiles were removed under reduced pressure, and the residue was suspended in petroleum ether (80 mL) and filtered under vacuum. The liquor was concentrated under reduced pressure, to give 10.12 g of oil residue that was used for the next step without further purification.

Methyl 3α,7α,12α-trimethoxymethyloxy-6α-ethyl-23(R)-hydroxy-5β-cholan-24-oate (4)

To a suspension of freshly crystallized and acetic acid free lead(IV)tetraacetate (6.85 g, 15.46 mmol) in distilled CH$_2$Cl$_2$ (50 mL) under N$_2$ atmosphere, a solution of 3 (10.12 g) in CH$_2$Cl$_2$ (30 mL) was added dropwise. After 30' the reaction mixture was filtered under vacuum through a celite pad. The filtrate was concentrated under reduced pressure and the residue was filtered through a silica gel pad (h: 6 cm, φ: 2 cm) collecting the crude reaction mixture with petroleum ether/AcOEt (8:2, v/v). After solvent evaporation, the residue (6.50 g) was dissolved in MeOH (50 mL) and treated with potassium carbonate (2.13 g, 15.5 mmol) at room temperature for 15'. The mixture was then diluted with CH$_2$Cl$_2$ (50 mL) and filtered under vacuum. The filtrate was further diluted with CH$_2$Cl$_2$ (70 mL) and washed with brine (70 mL). The aqueous phase was extracted with CH$_2$Cl$_2$ (3×40 mL), and the collected organic layers were dried over Na$_2$SO$_4$ anhydrous and concentrated under reduced pressure. The residue was purified by medium pressure liquid chromatography and collecting the desired compound with an isocratic elution constituted by petroleum ether/AcOEt (65:35, v/v) to obtain 4 in 20% yield.

Methyl 3α,7α,12α-trimethoxymethyloxy-6α-ethyl-23(S)-fluoro-5β-cholan-24-oate (5)

To a solution of 4 (0.92 g, 1.53 mmol) in distilled CH$_2$Cl$_2$ (40 mL) under N$_2$ atmosphere, diethylaminosulfurtrifluoride (1.0 mL, 7.7 mmol) was added and the reaction was stirred at room temperature for 10'. The mixture was cautiously poured in a saturated solution of NaHCO$_3$ (30 mL) and placed in a water-ice bath under magnetic stirring. Once the CO$_2$ release was completed, the two phases were separated and the organic layer was washed with H$_2$O (20 mL), brine (20 mL), dried over Na$_2$SO$_4$ anhydrous and concentrated under reduced pressure. The residue was purified by silica gel flash chromatography by using petroleum ether/AcOEt (85:15, v/v) to give the desired compound 5 in nearly quantitative yield.

$^1$H-NMR (CDCl$_3$, 400 MHz) δ 0.70 (3H, s, 18-CH$_3$), 0.87-0.92 (6H, m, 19-CH$_3$+CH$_2$CH$_3$), 1.07 (3H, d, J=5.7 Hz, 21-CH$_3$), 3.30-3.37 (1H, m, 3-CH), 3.35 (3H, s, OCH$_2$OCH$_3$), 3.36 (3H, s, OCH$_2$OCH$_3$), 3.43 (3H, s, OCH$_2$OCH$_3$), 3.49 (1H, s, 7-CH), 3.79 (3H, s, CO$_2$CH$_3$), 3.81 (1H, s, 12-CH), 4.59-4.74 (6H, m, 3×OCH$_2$OCH$_3$), 5.01 (1H, dd, J$_1$=10.1 Hz, J$_{2=52.0}$ Hz, 23-CHF).

3α,7α,12α-Trihydroxy-6α-ethyl-23(S)-fluoro-5β-cholan-24-oate (Compound 8)

To a solution of 5 (0.92 g, 1.53 mmol) in MeOH (20 mL), HCl 3 N (4.6 ml, 13.8 mmol) was added, and the mixture was stirred at 45° C. for 18 hrs. Sodium hydroxide (0.90 g, 22.95 mmol) was added, and the mixture was stirred at 45° C. for additional 5 hrs. MeOH was removed under reduced pressure and the residue was diluted with H$_2$O up to 30 mL and washed with Et$_2$O (2×15 mL). The aqueous phase was acidified with HCl 3 N, extracted with CH$_3$C$_{13}$/MeOH (85:15, v/v) (5×30 mL) and concentrated under reduced pressure. The residue was purified by RP-18 medium pressure liquid chromatography by using H$_2$O/MeOH as eluent (6:4→3:7) to obtain the desired compound Compound 8 in 87% yield.

rf: 0.44 (TLC: Silica Gel 60 RP-8 F$_{254}$S; eluent: H$_2$O/MeCN 50:50). $^1$H-NMR (CD$_3$OD, 400 MHz) δ: 0.74 (3H, s, 18-CH$_3$), 0.89-0.92 (6H, m, 19-CH$_3$+CH$_2$CH$_3$), 1.13 (3H, d, J=6.3 Hz, 21-CH$_3$), 2.17-2.23 (1H, m, 22-CH$_2$), 3.34-3.34 (1H, m, 3-CH), 3.67 (1H, s, 7-CH), 3.97 (1H, s, 12-CH), 4.99 (1H, psd, J$_{(H-F)}$=48 Hz, 23-CHF). $^{13}$C-NMR (CD$_3$OD, 100.6 MHz) δ 12.9, 13.8, 19.7, 24.3 (×2), 25.0, 29.1, 29.7, 31.9, 35.3, 36.2, 37.2 (×2), 37.6, 41.2 (d, J$_{C-F}$=19.8 Hz) 42.6, 44.0 (×2), 47.8, 48.5, 72.0, 74.1, 74.9, 91.7 (d, J$_{C-F}$=180.4 Hz), 176.7 (d, J$_{C-F}$=22.0 Hz). $^{19}$F-NMR (DMSO-d6, 376.5 MHz) δ − 184.7 (1F, m).

Example 9: Synthesis of Compound 9

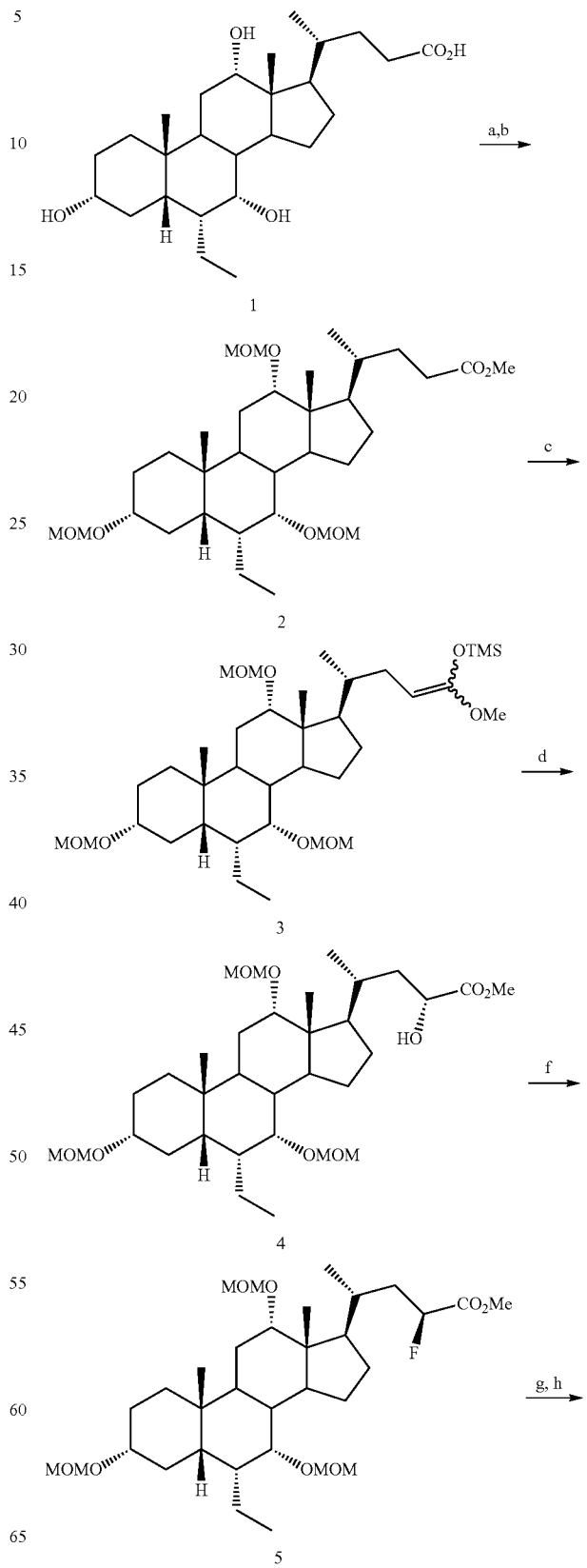

-continued

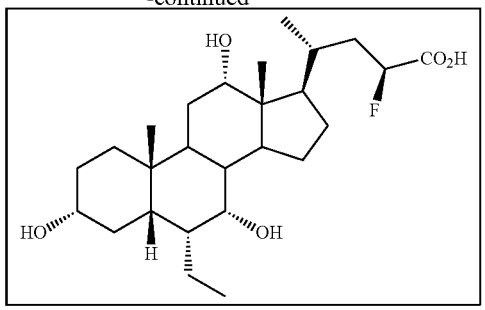

Reagents and conditions: a) pTSA, MeOH, us; b) MOMCl, DIPEA, DMAP, CH$_2$Cl$_2$, reflux; c) LDA, TMSCl, THF, -78° C.; d) Pb(OAc)$_4$, CH$_2$Cl$_2$; e) K$_2$CO$_3$, MeOH; f) DAST, CH$_2$Cl$_2$; g) HCl, MeOH, 45° C.; h) NaOH, MeOH, 45° C.

Methyl 3α,7α,12α-trimethoxymethyloxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluensulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with a saturated solution of NaHCO$_3$ (200 mL), H$_2$O (200 mL) and brine (200 mL). The organic layer was dried over Na$_2$SO$_4$ anhydrous and concentrated under reduced pressure. The residue was then dissolved in CH$_2$Cl$_2$ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with H$_2$O (100 mL), HCl 3 N (100 mL), H$_2$O (100 mL), saturated NaHCO$_3$ (100 mL) and brine (100 mL). The organic layer was dried over Na$_2$SO$_4$ anhydrous and concentrated under reduced pressure to afford 26.61 g (45.65 mmol) of 2 as a pale yellow oil (quantitative yield).

(E+Z)-3α,7α,12α-Trimethoxymethyloxy-6α-ethyl-24,24-trimetylsilyloxy-methoxy-5β-chol-23-ene (3)

To a stirred solution of diisopropylamine (11.7 mL, 82.5 mmol) in distilled THF (40 mL) under N$_2$ atmosphere and cooled at -40° C., nBuLi 2.5 M in hexane (32.0 mL, 79.3 mmol) was added dropwise. After 15', the solution was cooled up to -78° C. and chlorotrimethylsilane (12.7 mL, 84.5 mmol) was added dropwise. After additional 15', a solution of 3 (6.0 g, 10.30 mmol) in distilled THF (20 mL) was added portionwise in about 20' maintaining the internal temperature not over -70° C. Once the addition was completed, the reaction mixture was stirred at -78° C. for 1 hr and then warmed at room temperature. Volatiles were removed under reduced pressure, and the residue was suspended in petroleum ether (80 mL) and filtered under vacuum. The liquor was concentrated under reduced pressure, to give 10.12 g of oil residue that was used for the next step without further purification.

Methyl 3α,7α,12α-trimethoxymethyloxy-6α-ethyl-23(S)-hydroxy-5β-cholan-24-oate (4)

To a suspension of freshly crystallized and acetic acid free lead(IV)tetraacetate (6.85 g, 15.46 mmol) in distilled CH$_2$Cl$_2$ (50 mL) under N$_2$ atmosphere, a solution of 3 (10.12 g) in CH$_2$Cl$_2$ (30 mL) was added dropwise. After 30' the reaction mixture was filtered under vacuum through a celite pad. The filtrate was concentrated under reduced pressure and the residue was filtered through a silica gel pad (h: 6 cm, φ: 2 cm) collecting the crude reaction mixture with petroleum ether/AcOEt (8:2, v/v). After solvent evaporation, the residue (6.50 g) was dissolved in MeOH (50 mL) and treated with potassium carbonate (2.13 g, 15.5 mmol) at room temperature for 15'. The mixture was then diluted with CH$_2$Cl$_2$ (50 mL) and filtered under vacuum. The filtrate was further diluted with CH$_2$Cl$_2$ (70 mL) and washed with brine (70 mL). The aqueous phase was extracted with CH$_2$Cl$_2$ (3×40 mL), and the collected organic layers were dried over Na$_2$SO$_4$ anhydrous and concentrated under reduced pressure. The residue was purified by medium pressure liquid chromatography and collecting the desired compound with an isocratic elution constituted by petroleum ether/AcOEt (65:35, v/v) in 19% yield.

$^1$H-NMR (CDCl$_3$, 200 MHz) δ 0.65 (3H, s, 18-CH$_3$), 0.81-0.88 (6H, m, 19-CH$_3$+CH$_2$CH$_3$), 0.99 (3H, d, J=6.4 Hz, 21-CH$_3$), 3.32-3.36 (1H, m, 3-CH), 3.33 (6H, m, 2×OCH$_2$OCH$_3$), 3.39 (3H, s, OCH$_2$OCH$_3$), 3.46 (1H, s, 7-CH), 3.74 (3H, s, CO$_2$CH$_3$), 3.76 (1H, s, 12-CH), 4.18 (1H, t, J=6.6 Hz, 23-CH), 4.51-4.72 (6H, m, 3×OCH$_2$OCH$_3$). $^{13}$C-NMR (CDCl$_3$, 50.3 MHz) δ 11.7, 12.4, 18.7, 22.8, 23.0, 23.8, 24.9, 27.3, 27.6, 27.9, 30.3, 33.5, 35.5 (×2), 40.7, 41.2, 41.8, 42.2, 45.8, 46.3, 46.7, 52.2, 54.9, 55.7, 55.9, 69.9, 77.4, 79.9, 80.0, 94.3, 95.8, 98.4, 176.0.

Methyl 3α,7α,12α-trimethoxymethyloxy-6α-ethyl-23(R)-fluoro-5β-cholan-24-oate (5)

To a solution of 4 (0.92 g, 1.53 mmol) in distilled CH$_2$Cl$_2$ (40 mL) under N$_2$ atmosphere, diethylaminosulfurtrifluoride (1.0 mL, 7.7 mmol) was added and the reaction was stirred at room temperature for 10'. The mixture was cautiously poured in a saturated solution of NaHCO$_3$ (30 mL) and placed in a water-ice bath under magnetic stirring. Once the CO$_2$ release was completed, the two phases were separated and the organic layer was washed with H$_2$O (20 mL), brine (20 mL), dried over Na$_2$SO$_4$ anhydrous and concentrated under reduced pressure. The residue was purified by silica gel flash chromatography by using petroleum ether/AcOEt (85:15, v/v) to give the desired compound 5 in nearly quantitative yield.

$^1$H-NMR (CDCl$_3$, 400 MHz) δ 0.69 (3H, s, 18-CH$_3$), 0.87-0.91 (6H, m, 19-CH$_3$+CH$_2$CH$_3$), 1.05 (3H, d, J=5.7 Hz, 21-CH$_3$), 3.30-3.37 (1H, m, 3-CH), 3.35 (3H, s, OCH$_2$OCH$_3$), 3.37 (3H, s, OCH$_2$OCH$_3$), 3.43 (3H, s, OCH$_2$OCH$_3$), 3.49 (1H, s, 7-CH), 3.76 (1H, s, 12-CH), 3.79 (3H, s, CO$_2$CH$_3$), 4.59-4.75 (6H, m, 3×OCH$_2$OCH$_3$), 4.97 (1H, dt, J$_1$=4.9 Hz, J$_{2=48.0}$ Hz, 23-CHF).

3α,7α,12α-Trihydroxy-6α-ethyl-23(R)-fluoro-5β-cholan-24-oate (Compound 9)

To a solution of 5 (0.92 g, 1.53 mmol) in MeOH (20 mL), HCl 3 N (4.6 ml, 13.8 mmol) was added, and the mixture was stirred at 45° C. for 18 hrs. Sodium hydroxide (0.90 g, 22.95 mmol) was added, and the mixture was stirred at 45° C. for additional 5 hrs. MeOH was removed under reduced pressure and the residue was diluted with H$_2$O up to 30 mL and washed with Et$_2$O (2×15 mL). The aqueous phase was acidified with HCl 3 N, extracted with CH$_3$C$_{13}$/MeOH (85:15, v/v) (5×30 mL) and concentrated under reduced pressure. The residue was purified by RP-18 medium pressure liquid chromatography by using H₂O/MeOH as eluent (6:4→3:7) to obtain the desired compound Compound 9 in 82% yield.

rf: 0.42 (TLC: Silica Gel 60 RP-8 $F_{254}$S; eluent: H₂O/MeCN 50:50). ¹H-NMR (CD₃OD, 400 MHz) δ: 0.74 (3H, s, 18-CH₃), 0.89-0.91 (6H, m, 19-CH₃+CH₂CH₃), 1.11 (3H, d, J=5.0 Hz, 21-CH₃), 2.17-2.21 (1H, m, 22-CH₂), 3.31-3.35 (1H, m, 3-CH), 3.66 (1H, s, 7-CH), 3.98 (1H, s, 12-CH), 5.01 (1H, dd, $J_{1(H-F)}$=10.0 Hz, $J_{2(H-F)}$=51.3 Hz, 23-CHF). ¹³C-NMR (CD₃OD, 100.6 MHz) δ: 12.94, 13.87, 18.40, 24.40 (×2), 25.04, 29.17, 29.69, 30.63, 31.95, 34.63, 35.29, 37.20 (×2), 37.58, 40.90 (d, $J_{C-F}$=20.5 Hz), 42.62, 44.02, 44.10, 47.85, 48.55, 72.00, 74.07, 74.86, 89.01 (d, $J_{C-F}$=180.4 Hz), 175.43 (d, $J_{C-F}$=24.1 Hz). ¹⁹F-NMR (DMSO-d6, 376.5 MHz) δ − 184.0 (1F, bs).

Example 10: Synthesis of Compound 10

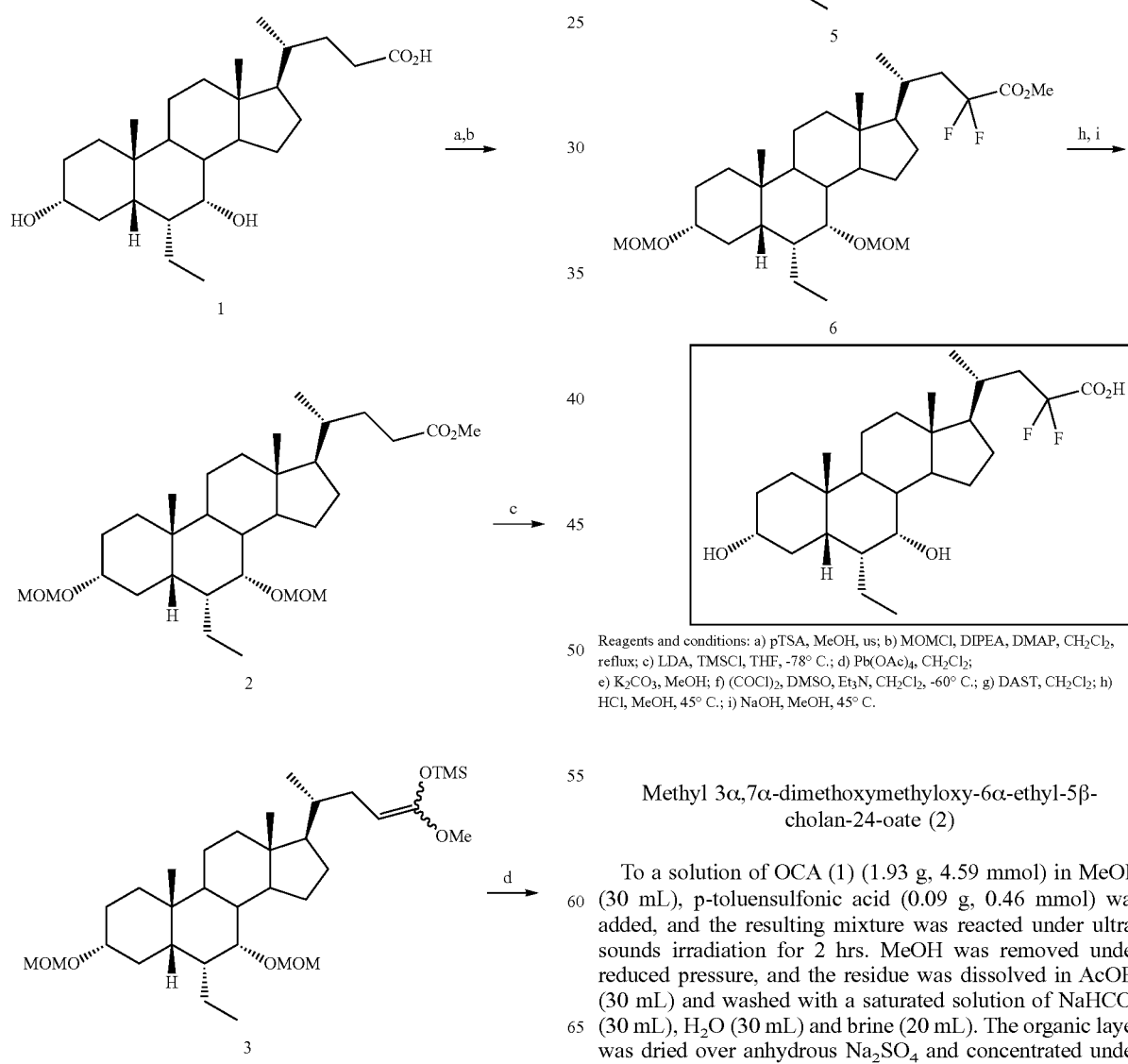

Reagents and conditions: a) pTSA, MeOH, us; b) MOMCl, DIPEA, DMAP, CH₂Cl₂, reflux; c) LDA, TMSCl, THF, -78° C.; d) Pb(OAc)₄, CH₂Cl₂;
e) K₂CO₃, MeOH; f) (COCl)₂, DMSO, Et₃N, CH₂Cl₂, -60° C.; g) DAST, CH₂Cl₂; h) HCl, MeOH, 45° C.; i) NaOH, MeOH, 45° C.

Methyl 3α,7α-dimethoxymethyloxy-6α-ethyl-5β-cholan-24-oate (2)

To a solution of OCA (1) (1.93 g, 4.59 mmol) in MeOH (30 mL), p-toluensulfonic acid (0.09 g, 0.46 mmol) was added, and the resulting mixture was reacted under ultra-sounds irradiation for 2 hrs. MeOH was removed under reduced pressure, and the residue was dissolved in AcOEt (30 mL) and washed with a saturated solution of NaHCO₃ (30 mL), H₂O (30 mL) and brine (20 mL). The organic layer was dried over anhydrous Na₂SO₄ and concentrated under reduced pressure. The residue was then dissolved in CH₂Cl₂

(60 mL), and treated with diisopropylethylamine (7.1 mL, 41.4 mmol), 4-(N,N-dimethylamino)-pyridine (0.05 g, 0.46 mmol) and methoxymethylchloride (2.1 mL, 27.6 mmol). The mixture was then refluxed for 36 hrs. The reaction was cooled at room temperature and washed with $H_2O$ (30 mL), HCl 3 N (30 mL), $H_2O$ (30 mL), saturated $NaHCO_3$ (300 mL) and brine (30 mL). The organic layer was dried over anhydrous $Na_2SO_4$ and concentrated under reduced pressure, to afford 2.38 g (4.55 mmol) of 2 as pale yellow oil (quantitative yield).

Methyl 3α,7α-dimethoxymethyloxy-6α-ethyl-23(R+S)-hydroxy-5β-cholan-24-oate (4)

To a stirred solution of diisopropylamine (7.6 mL, 82.5 mmol) in distilled THF (30 mL) under $N_2$ atmosphere and cooled at −40° C., nBuLi 2.5 M in hexane (20.6 mL, 51.6 mmol) was added dropwise. After 15', the solution was cooled to −78° C. and chlorotrimethylsilane (8.5 mL, 67.0 mmol) was added dropwise. After additional 15', a solution of 2 (3.50 g, 6.70 mmol) in distilled THF (20 mL) was added portionwise in about 20', maintaining the internal temperature at −70° C. Once the addition was finished, the reaction mixture was stirred at −78° C. for 1 hr and then warmed at room temperature. Volatiles were removed under reduced pressure. The residue was suspended in petroleum ether (80 mL) and filtered under vacuum. The liquor was concentrated under reduced pressure and dissolved in distilled $CH_2Cl_2$ (30 mL). The resulting solution was added dropwise to a suspension of freshly crystallized and acetic acid free lead(IV) tetraacetate (4.45 g, 10.50 mmol) in distilled $CH_2Cl_2$ (50 mL) under $N_2$ atmosphere. After 30' the reaction mixture was filtered under vacuum through a celite pad. The filtrate was concentrated under reduced pressure, and the residue was filtered through a silica gel pad (h: 4 cm, φ: 2 cm), collecting the crude with petroleum ether/AcOEt (8:2, v/v). After solvent evaporation, the residue was dissolved in MeOH (30 mL) and treated with potassium carbonate (1.38 g, 10.05 mmol). The resulting suspension was vigorously stirred at room temperature for 15'. The mixture was then diluted with $CH_2Cl_2$ (40 mL) and filtered under vacuum. The filtrate was diluted with additional $CH_2Cl_2$ (70 mL) and washed with brine (70 mL). The aqueous phase was extracted with $CH_2Cl_2$ (3×40 mL), and all the collected organic layers were dried over anhydrous $Na_2SO_4$ and concentrated under reduced pressure. The residue was purified by silica gel flash chromatography by using petroleum ether/AcOEt (8:2→1:1, v/v) to afford 1.73 g (3.21 mmol, 48%) of 4 (as epimeric mixture).

Methyl 3α,7α-dimethoxymethyloxy-6α-ethyl-23-oxo-5β-cholan-24-oate (5)

To a solution of oxalyl chloride (40.2 mL, 2.10 mmol) in distilled $CH_2Cl_2$ (12 mL) under $N_2$ atmosphere and cooled ad −60° C., DMSO (0.30 mL, 4.18 mmol) diluted in $CH_2Cl_2$ (2 mL) was added dropwise. After 15' a solution of 4 (0.45 g, 0.84 mmol) in $CH_2Cl_2$ (12 mL) was added dropwise, and the resulting mixture was stirred at −60° C. for 1 hr. Triethylamine (1.2 mL, 8.40 mmol) was added dropwise, and the mixture was slowly warmed at room temperature. The reaction mixture was treated with KOH 1 M (20 mL) for 5', the two phases were separated and the aqueous one was extracted with $CH_2Cl_2$ (2×20 mL). The collected organic layers were dried over anhydrous $Na_2SO_4$ and concentrated under reduced pressure. The residue was purified by silica gel flash chromatography using petroleum ether/AcOEt (9:1→8:2, v/v) as eluent to give 5 (0.43 g, 0.80 mmol, 96%).

Methyl 3α,7α-dimethoxymethyloxy-6α-ethyl-23,23-gemdifluoro-5β-cholan-24-oate (6)

To a solution of 5 (0.43 g, 0.80 mmol) in distilled $CH_2Cl_2$ (20 mL) under $N_2$ atmosphere, diethylaminosulfurtrifluoride (1.06 mL, 8.02 mmol) was added, and the reaction was stirred at room temperature for 12 hrs. The mixture was cautiously poured in saturated $NaHCO_3$ (50 mL) and stirred in a water-ice bath until $CO_2$ release completation. The two phases were separated and the organic layer was washed with $H_2O$ (20 mL), brine (20 mL), dried over anhydrous $Na_2SO_4$ and concentrated under reduced pressure. The residue was purified by silica gel flash chromatography by using a solution of petroleum ether/AcOEt (95:5→8:2, v/v) to yield 0.31 g (0.56 mmol, 71%) of pure 6.

3α,7α-Dihydroxy-6α-ethyl-23,23-gemdifluoro-5β-cholan-24-oic acid (Compound 10)

To a solution of 6 (0.31 g, 0.56 mmol) in MeOH (15 mL), HCl 3 N (1.7 mL, 5.04 mmol) was added, and the mixture was stirred at 45° C. for 12 hrs. Sodium hydroxide (0.33 g, 8.40 mmol) was added, and the mixture was stirred at 45° C. for additional 4 hrs. MeOH was removed under reduced pressure, and the residue was diluted with $H_2O$ up to 15 mL and washed with $Et_2O$ (2×10 mL). The aqueous phase was acidified by adding HCl 3 N, and the resulting whitish suspension was filtered through a RP-18 silica gel pad (h: 3 cm, φ: 1 cm) under vacuum, washing with $H_2O$ (50 mL) and collecting the crude material using a solution of $H_2O$/MeCN 40:60 (v/v). Once the solvent was removed under reduced pressure, the residue was purified by RP-18 medium pressure liquid chromatography with $H_2O$/MeCN (8:2→4:6, v/v). 0.22 g (0.48 mmol, 86%) of the pure difluoro derivative Compound 10 was obtained.

rf: 0.31 (TLC: Silica Gel 60 RP-8 $F_{254}S$; eluent: $H_2O$/MeCN 60:40). $^1$H-NMR (DMSO-$d_6$, 400 MHz) δ: 0.62 (3H, s, 18-$CH_3$), 0.82-0.91 (6H, m, 19-$CH_3$+$CH_2CH_3$), 1.01 (3H, d, J=6.1 Hz, 21-$CH_3$), 2.09-2.13 (1H, m, 22-$CH_2$), 3.17-3.21 (1H, m, 3-CH), 3.49 (1H, s, 7-CH), 4.07 (1H, bs, OH). $^{13}$C-NMR ($CD_3OD$, 100.6 MHz) δ 11.4, 11.6, 19.6, 20.3, 22.1, 22.9, 23.0, 28.0, 30.4, 30.9, 32.6, 33.5, 35.1, 35.5, 41.2, 42.0, 45.3, 48.5, 50.2, 55.6, 68.3, 70.5, 117.3 ($J_{C-F}$=248.7 Hz), 165.6 ($J_{C-F}$=31.6 Hz). $^{19}$F-NMR (DMSO-d6, 376.5 MHz) δ − 100.9 (2F, m). MS-TIC (−) m/z: 455.4.

Example 11: Synthesis of Compound 11

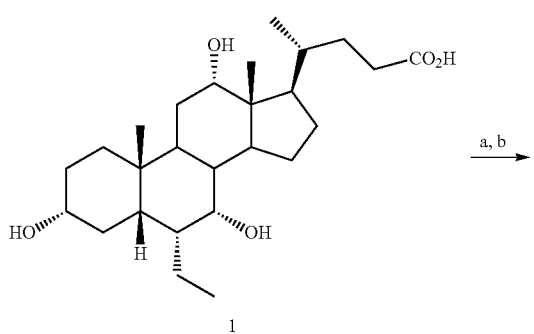

1

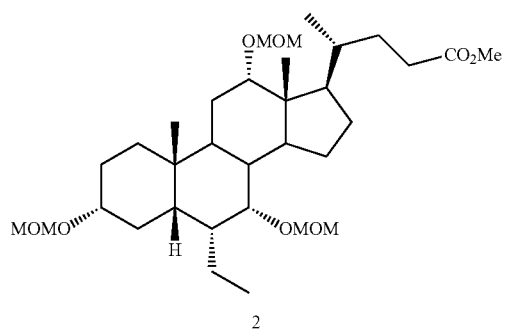

2

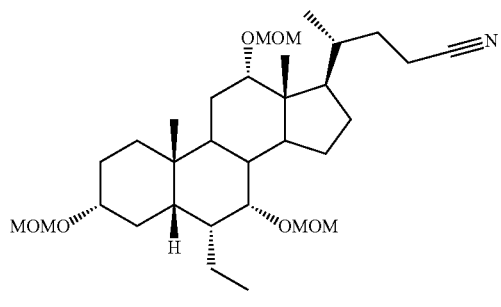

3

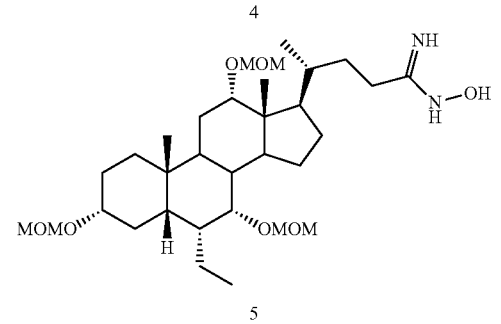

4

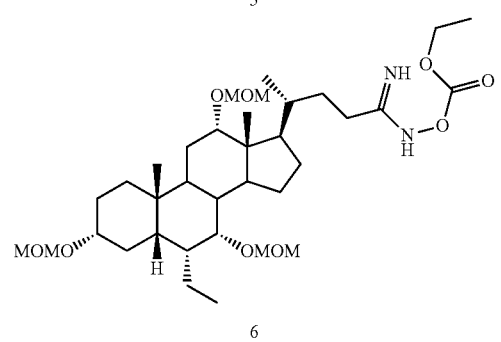

5

6

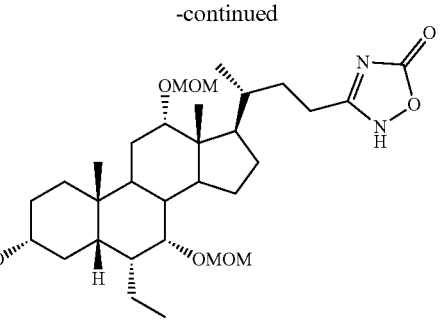

7

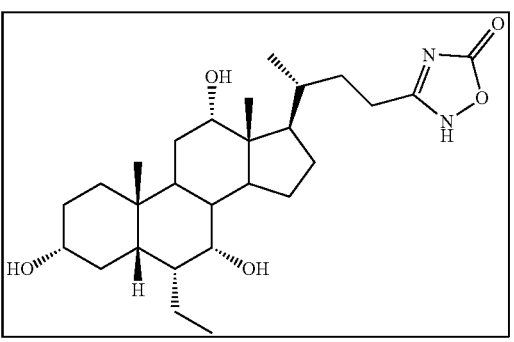

Reagents and conditions: a) pTSA, MeOH, us; b) MOMCl, DIPEA, DMAP, CH₂Cl₂, reflux; c) NaOH, MeOH; d) EtCO₂Cl, Et₃N, THF, aq. NH₃; e) CNCl, DMF; f) NH₂OH·HCl, Na₂CO₃, EtOH, reflux; g) EtCO₂Cl, Pyr, CH₂Cl₂; h) Pyr, PhMe, reflux; i) HCl, AcMe, 50° C.

Methyl 3α,7α,12α-trimethoxymethyloxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluensulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with a saturated solution of NaHCO₃ (200 mL), H₂O (200 mL) and brine (200 mL). The organic layer was dried over Na₂SO₄ anhydrous and concentrated under reduced pressure. The residue was then dissolved in CH₂Cl₂ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with H₂O (100 mL), HCl 3 N (100 mL), H₂O (100 mL), saturated NaHCO₃ (100 mL) and brine (100 mL). The organic layer was dried over Na₂SO₄ anhydrous and concentrated under reduced pressure to afford 26.61 g (45.65 mmol) of 2 as a pale yellow oil (quantitative yield).

3α,7α,12α-trimethoxymethyloxy-6α-ethyl-5β-cholan-24-amide (3)

2 (1.55 g, 3.44 mmol) was treated with NaOH 5% in MeOH (30 mL) at reflux under magnetic stirring for 2 hrs. MeOH was removed and the residue was dissolved in AcOEt (50 mL) and washed with H₂O (50 mL) and brine (50 mL). The organic layer was dried over Na₂SO₄ anhydrous and concentrated under reduced pressure. The oil residue was dissolved in THF (30 mL) and treated with ethyl chloroformiate (0.45 mL, 4.82 mmol) and triethylamine (0.72 mL, 5.16 mmol). The mixture was vigorously stirred for 1 hr. The reaction was diluted with AcOEt (50 mL), washed with H$_2$O (30 mL), aqueous HCl 1 N (30 mL), brine (30 mL), dried over Na$_2$SO$_4$ anhydrous and concentrated under reduced pressure, to obtain the desired amide intermediate 3 in quantitative yield. The crude was used for the next step without further purification.

3α,7α,12α-trimethoxymethyloxy-6α-ethyl-23-cyano-24-nor-5β-cholane (4)

To a solution of 3 (1.95 g, 3.44 mmol) in DMF (20 mL), cyanuric chloride (0.42 g, 6.88 mmol) was added and the reaction was stirred at room temperature for 18 hrs. The mixture was poured into AcOEt (100 mL) and washed with H$_2$O (5×50 mL), brine (30 mL), dried over Na$_2$SO$_4$ anhydrous and concentrated under reduced pressure. The residue was purified by silica gel flash chromatography with petroleum ether/AcOEt (9:1→7:3, v/v) to get 1.15 g (2.10, mmol, 61%) of the cyano derivative 4.

3α,7α,12α-trimethoxymethyloxy-6α-ethyl-5β-24-N-hydroxy-cholanamidine (5)

To a solution of 4 (0.60 g, 1.11 mmol) in EtOH (30 mL), hydroxylamine chlorohydrate (0.77 g, 11.16 mmol) and sodium carbonate decahydrate (3.20 g, 11.16 mmol) were added and the mixture was refluxed for 36 hrs. Volatiles were removed under reduced pressure and the resulting residue was dissolved in EtOAc (30 mL), washed with H$_2$O (3×30 mL), brine (30 mL), dried over anhydrous Na$_2$SO$_4$, filtered and concentrated under reduced pressure. The crude was purified by silica gel flash chromatography by using CHCl$_3$/MeOH (98:2→95:5, v/v) thereby obtaining 0.42 g (0.72 mmol, 65%) of pure 5.

3α,7α,12α-trimethoxymethyloxy-6α-ethyl-5β-24-N [(ethoxycarbonyl)oxy]imido cholanamide (6)

To a solution of 5 (0.42 g, 0.72 mmol) in distilled CH$_2$Cl$_2$ (30 mL), cooled at 0° C. and under N$_2$ atmosphere, ethyl chloroformate (0.07 mL, 0.94 mol) and pyridine (0.09 mL, 1.08 mmol) were added dropwise and the reaction mixture was stirred at room temperature for 1 hr. The reaction was quenched with H$_2$O (15 mL), the two phases were separated and the organic layer was washed with H$_2$O (3×15 mL), brine (15 mL), dried over anhydrous Na$_2$SO$_4$, filtered and concentrated under reduced pressure to afford 6 as crude material (0.44 g), which was used for the next step without further purification.

3α,7α,12α-trimethoxymethyloxy-6α-ethyl-24-nor-5β-23([1,2,4]-oxadiazole-3-one-5yl)-cholane (7)

A solution of 6 (0.44 g) in toluene (20 mL) and pyridine (5 mL) was refluxed for 48 hrs. The mixture was then diluted with AcOEt (50 mL), washed with H$_2$O (3×50 mL), brine (30 mL), dried over anhydrous Na$_2$SO$_4$, filtered and concentrated under reduced pressure, to obtain 0.43 g of 7 which was used as such for the next step.

3α,7α,12α-trihydroxy-6α-ethyl-24-nor-5β-23([1,2,4]-oxadiazole-3-one-5yl)-cholane (Compound 11)

To a solution of crude 8 (0.43 g) in acetone (15 mL), HCl 3 N (5 mL) was added, and the mixture was stirred at 50° C. for 6 hrs. The organic solvent was removed under reduced pressure, the residue was dissolved in CHCl$_3$ (30 mL) and washed with H$_2$O (3×20 mL), brine (20 mL), dried over anhydrous Na$_2$SO$_4$, filtered and concentrated under reduced pressure. The residue was purified by silica gel flash chromatography, by using CHCl$_3$/MeOH/AcOH (98:2:0.1→93:7:0.1, v/v/v), to give 0.14 g (0.29 mmol, 41% from intermediate 6) of pure Compound 11.

rf: 0.37 (TLC: Silica Gel 60 RP-8 F$_{254}$S; eluent: H$_2$O/MeCN 50:50). $^1$H-NMR (CDCl$_3$, 400 MHz) δ: 0.70 (3H, s, 18-CH$_3$), 0.89-0.92 (6H, m, 19-CH$_3$+CH$_2$CH$_3$), 1.03 (3H, d, J=5.4 Hz, 21-CH$_3$), 2.18-2.59 (2H, m, 23-CH$_2$), 3.42-3.45 (1H, m, 3-CH), 3.71 (1H, s, 7-CH), 3.99 (1H, s, 12-CH). $^{13}$C-NMR (CDCl$_3$, 100.6 MHz) δ: 11.6, 12.4, 17.2, 21.8, 22.1, 22.7, 23.2, 26.7, 27.5, 28.2, 30.0, 31.8, 33.4, 35.1, 35.4 (×2), 39.9, 41.3, 41.8, 45.0, 46.2, 46.4, 71.0, 72.2, 73.3, 160.4, 160.9.

Example 12: Synthesis of Compound 12

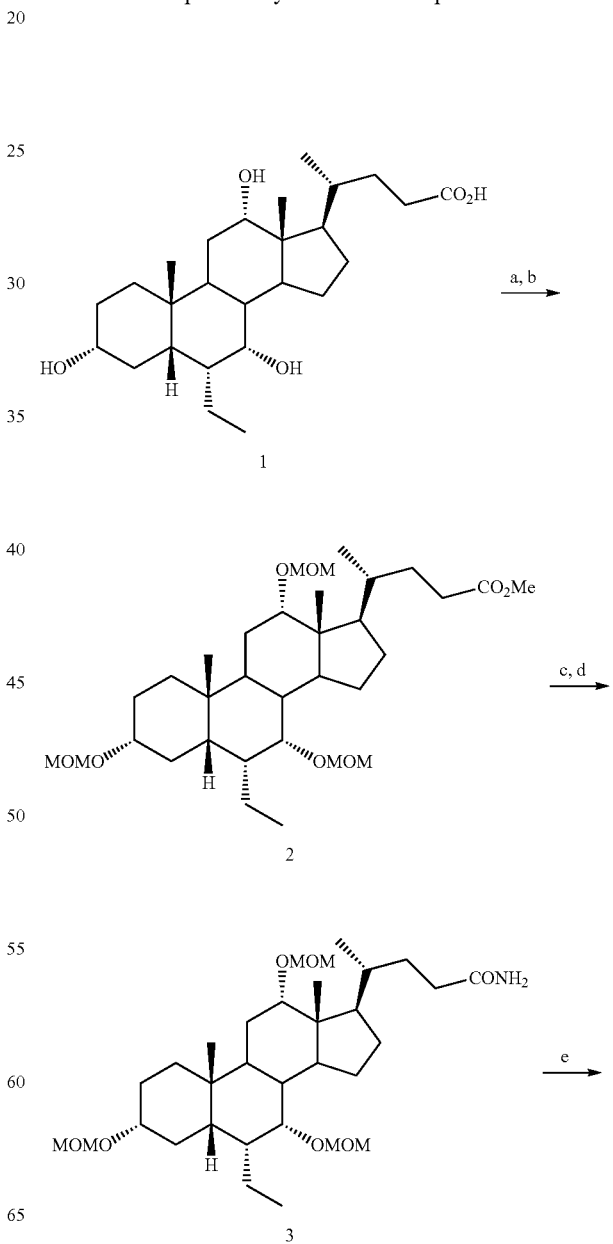

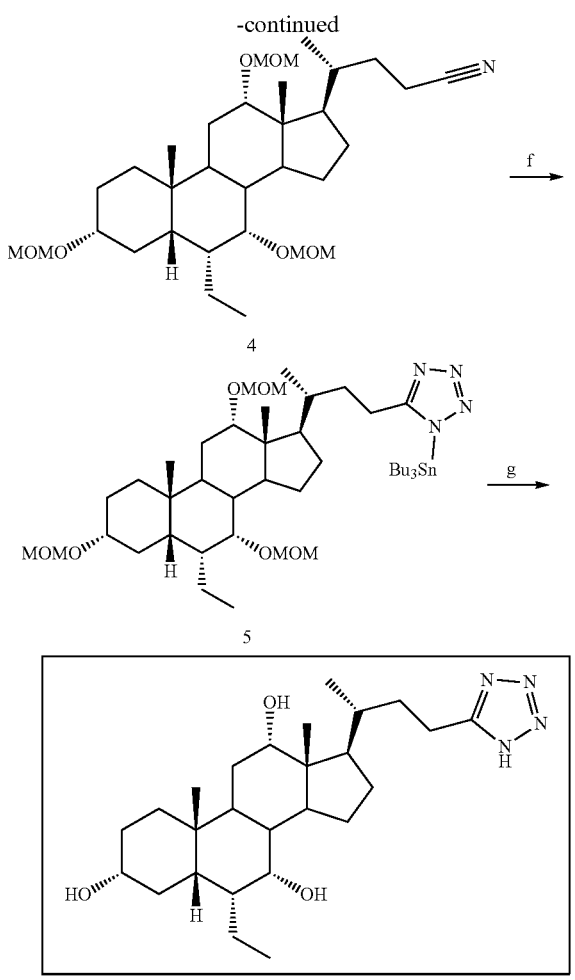

Reagents and conditions: a) pTSA, MeOH, us; b) MOMCl, DIPEA, DMAP, CH$_2$Cl$_2$, reflux; c) NaOH, MeOH; d) EtCO$_2$Cl, Et$_3$N, THF, aq. NH$_3$; e) CNCl, DMF; f) Bu$_3$SnN$_3$, PhMe, reflux; g) MeOH, HCl, 45° C.

Methyl 3α,7α,12α-trimethoxymethyloxy-6α-ethyl-5β-cholan-24-oate (2)

To a solution of 3α,7α,12α-trihydroxy-6α-ethyl-5β-cholan-24-oic acid (6-ECA, 1) (20.0 g, 45.9 mmol) in MeOH (150 mL), p-toluensulfonic acid (0.44 g, 2.29 mmol) was added and the resulting mixture was reacted under ultrasound irradiation for 2 hrs. MeOH was removed under reduced pressure and the residue was dissolved in AcOEt (200 mL) and washed with a saturated solution of NaHCO$_3$ (200 mL), H$_2$O (200 mL) and brine (200 mL). The organic layer was dried over Na$_2$SO$_4$ anhydrous and concentrated under reduced pressure. The residue was then dissolved in CH$_2$Cl$_2$ (180 mL) and the resulting solution was treated with diisopropylethylamine (94 mL, 550.5 mmol), 4-(N,N-dimethylamino)-pyridine (0.56 g, 4.6 mmol) and methoxymethylchloride (31.2 mL, 412.8 mmol). The mixture was stirred and refluxed for 48 hrs. The reaction was cooled at room temperature and washed with H$_2$O (100 mL), HCl 3 N (100 mL), H$_2$O (100 mL), saturated NaHCO$_3$ (100 mL) and brine (100 mL). The organic layer was dried over Na$_2$SO$_4$ anhydrous and concentrated under reduced pressure to afford 26.61 g (45.65 mmol) of 2 as a pale yellow oil (quantitative yield).

3α,7α,12α-Trimethoxymethyloxy-6α-ethyl-5β-cholan-24-amide (3)

2 (1.55 g, 3.44 mmol) was treated with NaOH 5% in MeOH (30 mL) at reflux under magnetic stirring for 2 hrs. MeOH was removed and the residue was dissolved in AcOEt (50 mL) and washed with H$_2$O (50 mL) and brine (50 mL). The organic layer was dried over Na$_2$SO$_4$ anhydrous and concentrated under reduced pressure. The oil residue was dissolved in THF (30 mL) and treated with ethyl chloroformate (0.45 mL, 4.82 mmol) and triethylamine (0.72 mL, 5.16 mmol). The mixture was vigorously stirred for 1 hr. The reaction was diluted with AcOEt (50 mL), washed with H$_2$O (30 mL), aqueous HCl 1 N (30 mL), brine (30 mL), dried over Na$_2$SO$_4$ anhydrous and concentrated under reduced pressure, to obtain the desired amide intermediate 3 in quantitative yield. The crude was used for the next step without further purification.

3α,7α,12α-Trimethoxymethyloxy-6α-ethyl-23-cyano-24-nor-5β-cholane (4)

To a solution of 3 (1.95 g, 3.44 mmol) in DMF (20 mL), cyanuric chloride (0.42 g, 6.88 mmol) was added and the reaction was stirred at room temperature for 18 hrs. The mixture was poured into AcOEt (100 mL) and washed with H$_2$O (5×50 mL), brine (30 mL), dried over Na$_2$SO$_4$ anhydrous and concentrated under reduced pressure. The residue was purified by silica gel flash chromatography with petroleum ether/AcOEt (9:1→7:3, v/v) to get 1.15 g (2.10, mmol, 61%) of the cyano derivative 4.

3α,7α,12α-Trihydroxy-6α-ethyl-23-(tetrazol-5-yl)-24-nor-5β-cholane (Compound 12)

To a solution of 4 (0.20 g, 0.36 mmol) in distilled PhMe (10 mL) and under N$_2$ atmosphere, tributyltin azide (0.50 mL, 1.80 mmol) was added and the resulting mixture was refluxed for 72 hrs. When completed, the reaction mixture was diluted with EtOAc (50 mL), washed with H$_2$O (3×15 mL), brine (15 mL), dried over anhydrous Na$_2$SO$_4$, filtered and concentrated under reduced pressure. The crude 5 (0.24 g) was dissolved in acetone (15 mL) and treated with HCl 3 N (5 mL) at 50° C. for 6 hrs. Acetone was removed under reduced pressure, the residue was diluted with H$_2$O (20 mL) and basified up to pH 14 by adding NaOH 3 N. The mixture was washed with Et$_2$O (3×20 mL), acidified with HCl 3 N, extracted with CHCl$_3$/MeOH (9:1, v/v), dried over Na$_2$SO$_4$ anhydrous and concentrated under reduced pressure. The residue was purified by silica gel flash chromatography using CHCl$_3$/MeOH/AcOH (96:4:0.1→90:10:0.1, v/v/v), to get 0.11 g (0.24 mmol, 66%) of pure Compound 12.

rf: 0.39 (TLC: Silica Gel 60 RP-8 F254S; eluent: H$_2$O/MeCN 50:50). $^1$H-NMR (CD$_3$OD, 400 MHz) δ: 0.70 (3H, s, 18-CH$_3$), 0.88-0.91 (6H, m, 19-CH$_3$+CH$_2$CH$_3$), 1.13 (3H, d, J=6.1 Hz, 21-CH$_3$), 2.18-2.22 (1H, m, 22-CH$_2$), 2.83-2.91 (1H, m, 23-CH$_2$), 2.97-3.04 (1H, m, 23-CH$_2$), 3.29-3.34 (1H, m, 3-CH), 3.66 (1H, s, 7-CH), 3.96 (1H, s, 12-CH). $^{13}$C-NMR (CD$_3$OD, 100.6 MHz) δ: 12.0, 12.9, 17.5, 21.1, 23.4, 23.5, 24.1, 28.2, 28.7, 29.7, 31.0, 34.3, 35.2, 36.3, 36.6, 36.7, 41.7, 43.1, 43.1, 46.9, 47.5, 47.8, 71.1, 73.1, 74.0, 158.8.

Example 13: Synthesis of Compound 13

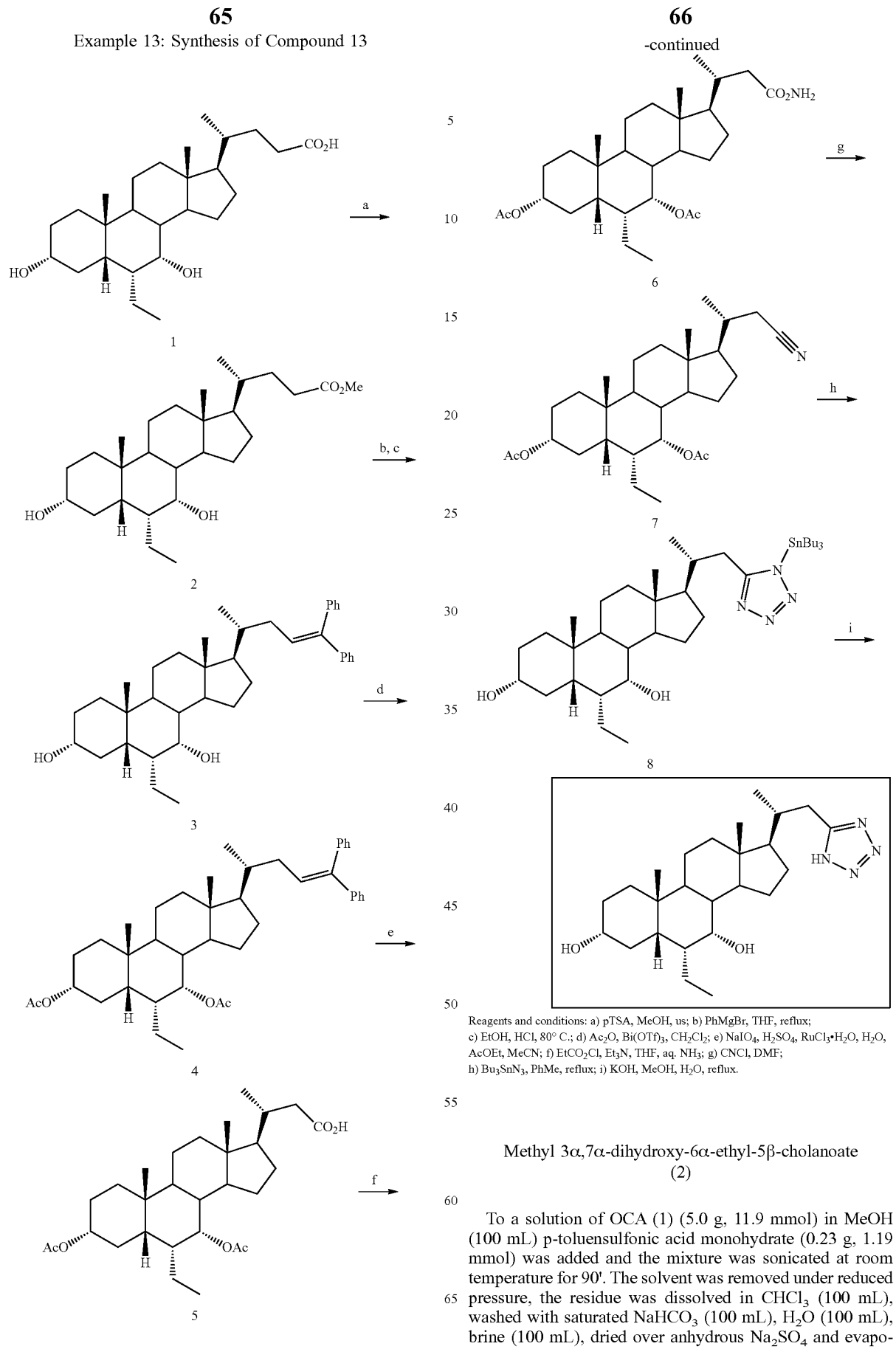

Reagents and conditions: a) pTSA, MeOH, us; b) PhMgBr, THF, reflux; c) EtOH, HCl, 80° C.; d) Ac₂O, Bi(OTf)₃, CH₂Cl₂; e) NaIO₄, H₂SO₄, RuCl₃•H₂O, H₂O, AcOEt, MeCN; f) EtCO₂Cl, Et₃N, THF, aq. NH₃; g) CNCl, DMF; h) Bu₃SnN₃, PhMe, reflux; i) KOH, MeOH, H₂O, reflux.

Methyl 3α,7α-dihydroxy-6α-ethyl-5β-cholanoate (2)

To a solution of OCA (1) (5.0 g, 11.9 mmol) in MeOH (100 mL) p-toluensulfonic acid monohydrate (0.23 g, 1.19 mmol) was added and the mixture was sonicated at room temperature for 90'. The solvent was removed under reduced pressure, the residue was dissolved in CHCl₃ (100 mL), washed with saturated NaHCO₃ (100 mL), H₂O (100 mL), brine (100 mL), dried over anhydrous Na₂SO₄ and evaporated under reduced pressure. The white solid thus obtained (5.17 g, 11.89 mmol) was used for the next step without further purification.

3α,7α-Dihydroxy-6α-ethyl-24,24-biphenyl-5β-cholan-23-ene (3)

To a solution of methyl 6α-ethyl-3α,7α-dihydroxy-5β-cholanoate (2) (5.17 g, 11.89 mmol) in dry THF (125 mL), phenylmagnesium bromide 3 M in Et$_2$O (39.6 mL, 118.9 mmol) was added dropwise. The mixture was refluxed for 12 hrs. After cooling at room temperature, the mixture was treated with H$_2$O (100 mL) and HCl 3 M (100 mL). The mixture was extracted with EtOAc (3×80 mL), the combined organic layers were washed with brine, dried over anhydrous Na$_2$SO$_4$ and evaporated under reduced pressure. The crude was dissolved in MeOH (100 mL) and refluxed in the presence of HCl 37% (10 mL) for 1 hr. MeOH was evaporated, the obtained residue was dissolved in EtOAc (120 mL), washed with H$_2$O (2×100 mL), saturated NaHCO$_3$ (100 mL), brine (100 mL), dried over anhydrous Na$_2$SO$_4$ and evaporated under reduced pressure. The biphenyl derivative 3 was used for the next step without purification.

3α,7α-Diacetoxy-6α-ethyl-24,24-biphenyl-5β-cholan-23-ene (4)

To a solution of 3 (6.42 g, 11.89 mmol) in CH$_2$Cl$_2$ (70 mL), acetic anhydride (6.06 g, 59.45 mmol) and bismuth trifluoromethanesulfonate (0.39 g, 0.59 mmol) were added. The resulting mixture was stirred at room temperature for 1 hr. A saturated aqueous solution of NaHCO$_3$ (50 mL) was then carefully added and the phases were separated. The aqueous layer was extracted with CH$_2$Cl$_2$ (2×50 mL). The combined organic layers were washed with H$_2$O (100 mL), brine (100 mL), dried over anhydrous Na$_2$SO$_4$ and concentrated under reduced pressure. The crude was purified by silica gel flash chromatography using an eluent constituted by petroleum ether/EtOAc (95:5→7:3, v/v) obtaining 5.56 g (8.91 mmol, 75%) of desired intermediate 4.

3α,7α-Diacetoxy-6α-ethyl-24-nor-5β-cholan-23-oic acid (5)

To a suspension of sodium periodate (21.13 g, 98.73 mmol) in H$_2$O (20 mL), H$_2$SO$_4$ 2 N in H$_2$O (3.22 mL) was added and the mixture was stirred at room temperature for 1 hr. The mixture was cooled to 0° C. and treated with ruthenium trichloride hydrate (0.11 g, 0.55 mmol) which was added in one portion. After 1 hr, acetonitrile (31 mL) was added to the solution and after additional 5', a solution of biphenyl derivative 4 (6.85 g, 10.97 mmol) in EtOAc (43 mL) was added. The mixture was stirred at room temperature for 1 hr. The white solid thus formed was filtered off, then the liquor was poured into H$_2$O (100 mL) and extracted with EtOAc (3×50 mL). The combined organic layers were filtered through a Celite pad, washed with a saturated solution of Na$_2$S$_2$O$_3$ in H$_2$O (100 mL), brine (100 mL), dried over anhydrous Na$_2$SO$_4$ and concentrated under reduced pressure. The residue was purified by silica gel flash chromatography eluting with EtOAc in petroleum ether from 10 to 50%. The desired acid 5 was obtained as white solid (5.27 g, 10.75 mmol, 98%).

3α,7α-Diacetoxy-6α-ethyl-24-nor-5β-cholan-23-amide (6)

To a solution of acid 5 (2.12 g, 4.31 mmol) in dry THF (40 mL) at 0° C., triethylamine (0.65 g, 6.47 mmol) and ethyl-chloroformate (0.65 g, 6.04 mmol) were added. The resulting suspension was stirred at room temperature for 1 hr. NH$_3$ (28% in H$_2$O, 0.73 g, 2.94 mL) was added dropwise to the mixture and stirred at room temperature for 12 hrs. The mixture was poured into H$_2$O (50 mL) and extracted with EtOAc (2×50 mL). The combined organic layers were washed with HCl 1 N (50 mL), H$_2$O (50 mL), brine (50 mL), dried over anhydrous Na$_2$SO$_4$ and concentrated under reduced pressure. The compound 6 was used for the next step without further purification.

3α,7α-Diacetoxy-6α-ethyl-22-cyano-23,24-bisnor-5β-cholane (7)

To a solution of amide 6 (1.50 g, 3.06 mmol) in DMF (30 mL), cyanogen chloride (0.37 g, 6.013 mmol) was added and the reaction mixture was stirred at room temperature for 12 hrs. The mixture was diluted with EtOAc (30 mL), washed with H$_2$O (3×30 mL), brine (30 mL), dried over anhydrous Na$_2$SO$_4$ and concentrated under reduced pressure. The oily residue was purified by silica gel flash chromatography eluting with EtOAc in petroleum ether from 10 to 50% (v/v) obtaining 0.98 g (2.08 mmol, 68%) of the desired nitrile derivative 7.

3α,7α-dimethoxymethyloxy-6α-ethyl-22-[1-(tributylstannyl)-tetrazol-5-yl]-23,24-bisnor-5β-cholane (8)

To a solution of nitrile 7 (0.81 g, 1.72 mmol) in toluene (25 mL), tributyltin azide (2.87 g, 8.58 mmol) was added and the reaction was refluxed for 36 hrs. The mixture was then cooled at room temperature, diluted with EtOAc (25 mL), washed with HCl 3 N (3×20 mL), H$_2$O (50 mL), brine (50 mL), dried over anhydrous Na$_2$SO$_4$ and concentrated under reduced pressure dried over Na$_2$SO$_4$ and concentrated under reduced pressure. The residue was purified by silica gel flash chromatography (eluting with methanol in dichloromethane from 2 to 5%, v/v) obtaining 0.31 g (0.61 mmol, 61%) of the desired protected tetrazole 8.

3α,7α-Dihydroxy-6α-ethyl-23-(tetrazol-5-yl)-24-nor-5β-cholane (Compound 13)

To a suspension of tetrazole 8 (0.27 g, 0.53 mmol) in H$_2$O (1 mL) and MeOH (7 mL), KOH (0.444 g, 7.87 mmol) was added. The mixture was submitted to microwave irradiation (T=135° C., P$_{max}$=250 psi, Power$_{max}$=200 W) for 16 hrs. The organic solvent was removed under reduced pressure, the residue was dissolved in H$_2$O (50 mL) and extracted with Et$_2$O (2×15 mL). The aqueous phase was acidified with HCl 3 N and extracted with CH$_2$Cl$_2$ (3×15 mL). The combined organic layers were washed with H$_2$O (50 mL), brine (50 mL), dried over anhydrous Na$_2$SO$_4$ and evaporated under reduced pressure. The crude was purified by silica gel flash chromatography (eluting with MeOH in CHCl$_3$ from 0 to 10%, v/v) to furnish the desired derivative Compound 13 as white solid (0.19 g, 0.44 mmol, 84%).

rf: 0.31 (TLC: Silica Gel 60 F$_{254}$S; eluent: CHCl$_3$/MeOH/AcOH 96:4:1). $^1$H-NMR (CD$_3$OD, 400 MHz) δ 0.75 (3H, s, 18-CH$_3$), 0.89-0.892 (9H, m, 19-CH$_3$+21-CH$_3$+CH$_2$CH$_3$), 2.66 (1H, dd, J$_1$=9.7 Hz, J$_{2=14.5}$ Hz, 22-CH$_2$), 3.04 (1H, dd, J$_1$=3.2 Hz, J$_{2=14.5}$ Hz, 22-CH$_2$), 3.29-3.35 (1H, m, 3-CH), 3.67 (1H, s, 7-CH). $^{13}$C-NMR (CD$_3$OD, 400 MHz) δ 12.9, 13.1, 20.1, 22.8, 24.4, 24.6, 25.5, 30.4, 31.9, 32.1, 35.2, 35.4, 37.5, 37.6, 38.4, 41.7, 42.1, 44.0, 44.7, 47.8, 52.9, 58.3, 72.0, 74.0, 158.1.

Example 14: Synthesis of Compound 14

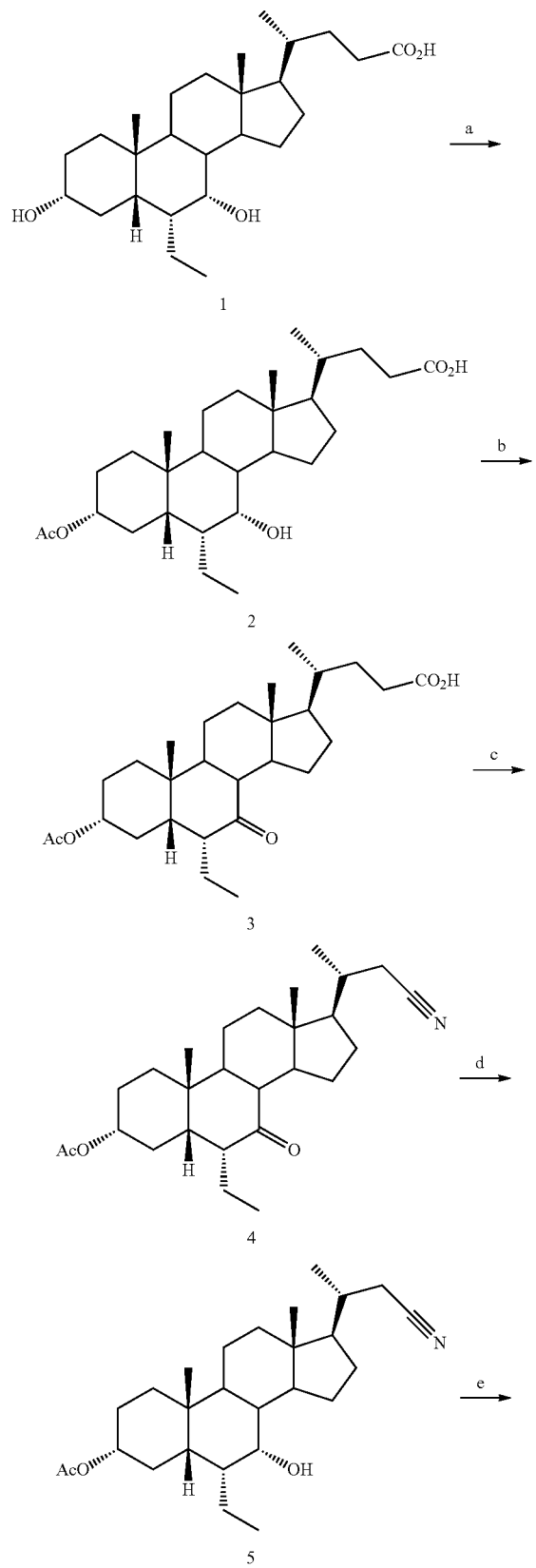

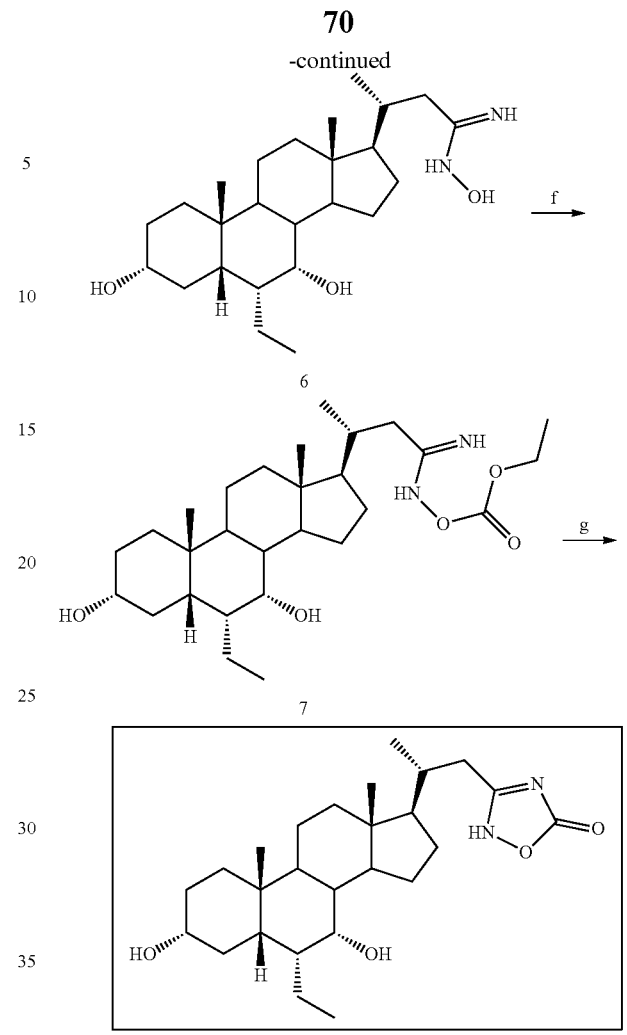

Reagents and conditions: a) Ac$_2$O, DIPEA, DMAP, CH$_2$Cl$_2$; b) PCC, CH$_2$Cl$_2$; c) TFA, TFAA, NaNO$_2$, 0° C.; d) NaBH$_4$, THF, H$_2$O, 0° C.; e) NH$_2$OH•HCl, Na$_2$CO$_3$, EtOH, reflux; f) EtCO$_2$Cl, Pyr, CH$_2$Cl$_2$; g) Pyr, PhMe, reflux.

3α-Acetoxy-6α-ethyl-7α-hydroxy-5β-cholan-24-oic acid (2)

To a solution of OCA (1) (5.00 g, 11.87 mmol) in CH$_2$Cl$_2$ (50 mL), Ac$_2$O (8.4 mL, 89.22 mmol), diisopropylethylamine (15.5 mL, 89.22 mmol) and 4-(N,N-dimethylamino)-pyridine (0.54 g, 4.46 mmol) were added, and the resulting suspension was stirred at reflux for 10'. The mixture was cooled at room temperature, diluted with CH$_2$Cl$_2$ (50 mL) and washed with H$_2$O (3×50 mL) and HCl 3 N (50 mL). The organic layer was treated with HCl 37% (5 mL) for 2'. H$_2$O (50 mL) was added, the two phases separated and the organic one was washed with saturated NaHCO$_3$ (100 mL) and brine (100 mL). The organic layer was dried over anhydrous Na$_2$SO$_4$ and concentrated under reduced pressure, to afford 5.49 g of 2 as pale yellow solid (quantitative yield).

3α-Acetoxy-6α-ethyl-7α-oxo-5β-cholan-24-oic acid (3)

To a solution of 2 (5.49 g, 11.87 mmol) in CH$_2$Cl$_2$ (60 mL), pyridinium chlorochromate (7.67 g, 35.69 mmol) was added, and the resulting dark mixture was stirred at room temperature for 2 hrs. The thus obtained suspension was filtered under vacuum through a celite pad, and the filtrate was washed with saturated NaHCO$_3$ (100 mL), brine (100 mL), dried over anhydrous Na$_2$SO$_4$ and concentrated under reduced pressure. The residue was purified by silica gel flash chromatography, by using petroleum ether/AcOEt (8:2→6: 4, v/v), thereby obtaining 4.43 g (9.61 mmol, 80%) of pure 3.

3α-Acetoxy-6α-ethyl-7α-oxo-22-cyano-23,24-bisnor-5β-cholane (4)

To a solution of 3 (4.43 g, 9.55 mmol) in trifluoroacetic acid (30 mL) cooled at 0° C., trifluoroacetic anhydride (10.1 mL, 71.61 mmol) was added, and the resulting mixture was stirred at the same temperature for 45'. Keeping the temperature at 0° C., sodium nitrite (1.98 g, 28.64 mmol) was added portionwise, and the thus obtained red solution was stirred at 0° C. for 1 hr and then at 45° C. for additional 50'. The mixture was cooled at room temperature and slowly poured in H$_2$O/ice bath (about 150 mL) and extracted with AcOEt (3×50 mL). The collected organic layers were washed with NaOH 5 M (3×50 mL) till neutral pH, washed with H$_2$O (50 mL), brine (50 mL), dried over anhydrous Na$_2$SO$_4$ and concentrated under reduced pressure, to obtain 3.51 g of 4 that was used as such for the next step.

3α-Acetoxy-6α-ethyl-7α-hydroxy-22-cyano-23,24-bisnor-5β-cholane (5)

To a solution of 4 (3.51 g, 8.18 mmol) in THF (80 mL) and H$_2$O (20 mL) cooled at 0° C., NaBH$_4$ (1.25 g, 32.88 mmol) was added portionwise. After 30' the reaction was quenched by adding AcOEt (100 mL) and HCl 3 N (30 mL). The two phases were separated, and the aqueous one was extracted with AcOEt (2×50 mL). The collected organic layers were washed with H$_2$O (50 mL), brine (50 mL), dried over anhydrous Na$_2$SO$_4$ and concentrated under reduced pressure, to afford the desired 5 (3.52 g) in quantitative yield.

3α,7α-Dihydroxy-6α-ethyl-24-nor-5β-23-N-hydroxy-cholanamidine (6)

To a solution of 5 (3.52 g, 8.18 mmol) in EtOH (120 mL), hydroxylamine chlorohydrate (17.55 g, 109.35 mmol) and sodium carbonate decahydrate (31.28 g, 109.35 mmol) were added and the mixture was stirred and refluxed for 48 hrs. Volatiles were removed under reduced pressure and the resulting residue was dissolved in EtOAc (150 mL), washed with H$_2$O (3×100 mL), brine (100 mL), dried over anhydrous Na$_2$SO$_4$, filtered and concentrated under reduced pressure, to obtain 3.45 g of 6, which was used for the next step without further purification.

3α,7α-Dihydroxy-6α-ethyl-24-nor-5β-23-N[(ethoxycarbonyl)oxy]imidocholanamide (7)

To a solution of 6 (3.45 g, 8.18 mmol mmol) in distilled CH$_2$Cl$_2$ (100 mL), cooled at 0° C. and under N$_2$ atmosphere, pyridine (0.99 mL, 12.27 mmol) and ethyl chloroformate (0.70 mL, 7.36 mmol) were added dropwise and the reaction mixture was stirred at room temperature for 1 hr. The reaction was quenched with H$_2$O (50 mL), the two phases were separated and the organic layer was washed with H$_2$O (3×50 mL), brine (50 mL), dried over anhydrous Na$_2$SO$_4$, filtered and concentrated under reduced pressure to afford 7 (3.50 g), which was used for the next step without further purification.

3α,7α-Dihydroxy-6α-ethyl-23,24-bisnor-5β-22([1,2,4]-oxadiazole-3-one-5yl)-cholane (Compound 14)

A solution of crude 7 (3.50 g) in toluene (100 mL) and pyridine (20 mL) was refluxed for 72 hrs. The mixture was then cooled at room temperature, diluted with AcOEt (200 mL), washed with H$_2$O (100 mL), HCl 3 N (100 mL), H$_2$O (100 mL), brine (30 mL), dried over anhydrous Na$_2$SO$_4$, filtered and concentrated under reduced pressure. The residue was purified by silica gel flash chromatography by using a solution of CH$_2$Cl$_2$/MeOH/AcOH (98:2:0.1→95:5:0.1, v/v/v), to obtain 1.23 g of pure Compound 14 in 34% from intermediate 5.

rf: 0.18 (TLC: Silica Gel 60 RP-8 F$_{254}$S; eluent: H$_2$O/MeOH 20:80). $^1$H-NMR (CD$_3$OD, 400 MHz) δ 0.75 (3H, s, 18-CH$_3$), 0.92-0.96 (6H, m, 19-CH$_3$+CH$_2$CH$_3$), 0.99 (3H, d, J=5.8, 21-CH$_3$), 2.19 (1H, m, 22-CH$_2$), 2.67 (1H, m, 22-CH$_2$), 3.28-3.35 (1H, m, 3-CH), 3.66 (1H, s, 7-CH). $^{13}$C-NMR (CD$_3$OD, 400 MHz) δ 12.0, 12.4, 19.1, 21.9, 23.4, 23.7, 24.5, 29.3, 31.2, 32.8, 34.3, 34.5, 35.6, 36.6, 36.7, 40.8, 41.5, 43.1, 43.9, 46.9, 51.6, 57.5, 71.1, 73.1, 160.7, 162.3.

Example 15: Synthesis of Compound 15

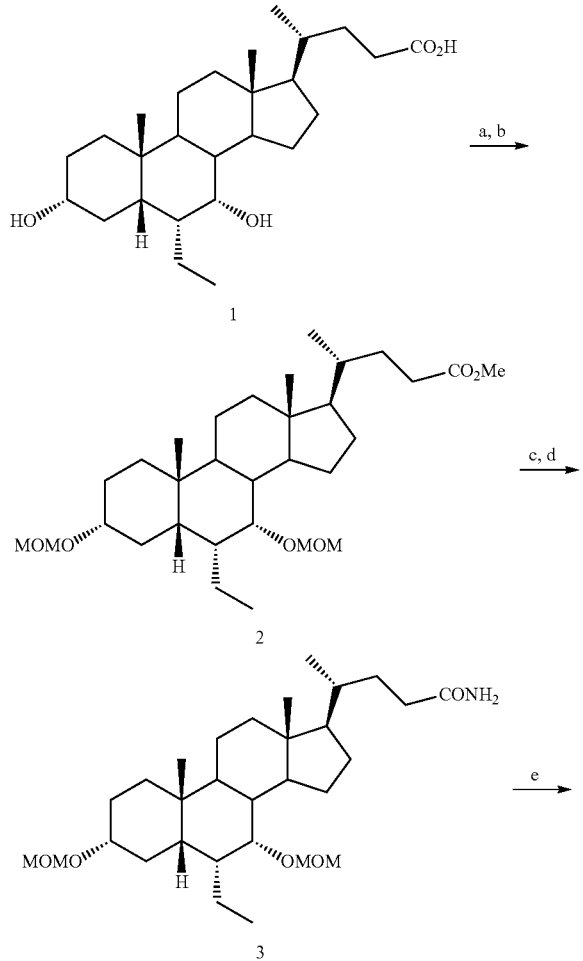

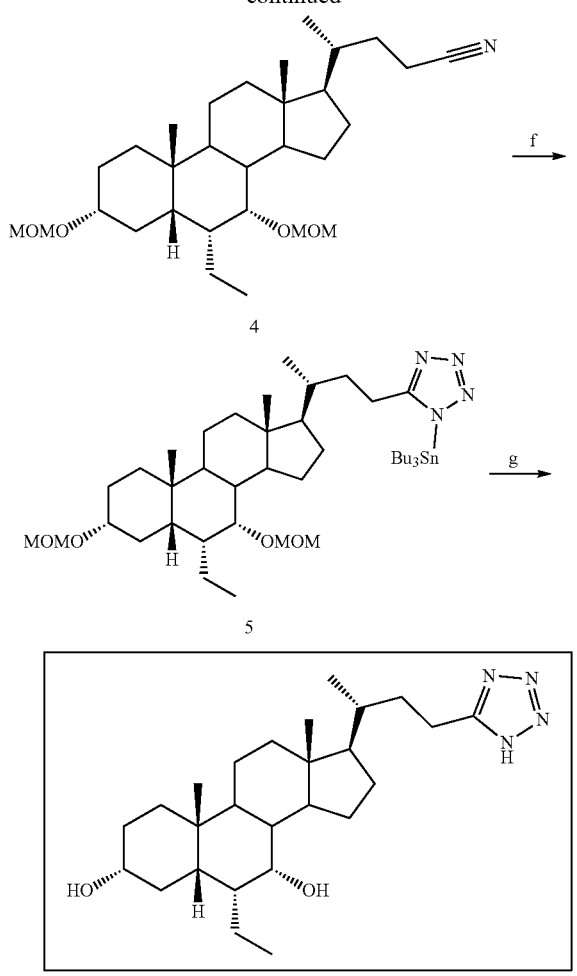

Reagents and conditions: a) pTSA, MeOH, us; b) MOMCl, DIPEA, DMAP, CH₂Cl₂, reflux; c) NaOH, MeOH; d) EtCO₂Cl, Et₃N, THF, aq. NH₃; e) CNCl, DMF; f) Bu₃SnN₃, PhMe, reflux; g) MeOH, HCl, 45° C.

Methyl 3α,7α-Dimethoxymethyloxy-6α-ethyl-5β-cholan-24-oate (2)

To a solution of OCA (1) (1.93 g, 4.59 mmol) in MeOH (30 mL), p-toluensulfonic acid (0.09 g, 0.46 mmol) was added, and the resulting mixture was reacted under ultrasounds irradiation for 2 hrs. MeOH was removed under reduced pressure, and the residue was dissolved in AcOEt (30 mL) and washed with a saturated solution of NaHCO₃ (30 mL), H₂O (30 mL) and brine (20 mL). The organic layer was dried over anhydrous Na₂SO₄ and concentrated under reduced pressure. The residue was then dissolved in CH₂Cl₂ (60 mL), and treated with diisopropylethylamine (7.1 mL, 41.4 mmol), 4-(N,N-dimethylamino)-pyridine (0.05 g, 0.46 mmol) and methoxymethylchloride (2.1 mL, 27.6 mmol). The mixture was then refluxed for 36 hrs. The reaction was cooled at room temperature and washed with H₂O (30 mL), HCl 3 N (30 mL), H₂O (30 mL), saturated NaHCO₃ (300 mL) and brine (30 mL). The organic layer was dried over anhydrous Na₂SO₄ and concentrated under reduced pressure, to afford 2.38 g (4.55 mmol) of 2 as pale yellow oil (quantitative yield).

3α,7α-Dimethoxymethyloxy-6α-ethyl-5β-cholan-24-amide (3)

2 (2.24 g, 4.31 mmol) was treated with 40 mL of a methanolic solution of NaOH 5% at reflux under magnetic stirring for 2 hrs. MeOH was then removed, the residue was dissolved in AcOEt (60 mL) and washed with H₂O (60 mL) and brine (60 mL). The organic layer was dried over anhydrous Na₂SO₄ and concentrated under reduced pressure. The oil residue was dissolved in THF (40 mL) and treated with ethyl chloroformate (0.57 mL, 6.04 mmol) and triethylamine (0.90 mL, 6.47 mmol). The mixture was vigorously stirred for 1 hr. Once the reaction was completed, the mixture was diluted with AcOEt (60 mL), washed with H₂O (30 mL), HCl 1 N (30 mL), brine (30 mL) dried over anhydrous Na₂SO₄ and concentrated under reduced pressure, to obtain the desired intermediate 3 in quantitative yield. The crude was used for the next step without further purification.

3α,7α-dimethoxymethyloxy-6α-ethyl-23-cyano-24-nor-5β-cholane (4)

To a solution of 3 (2.01 g, 3.96 mmol) in DMF (40 mL), cyanuric chloride (0.48 g, 7.92 mmol) were added, and the reaction was stirred at room temperature for 16 hrs. The mixture was poured into AcOEt (100 mL), washed with H₂O (5×50 mL) and brine, (30 mL) dried over anhydrous Na₂SO₄ and concentrated under reduced pressure. The residue was purified by silica gel flash chromatography with petroleum ether/AcOEt as eluent (9:1→65:35, v/v), to obtain 1.43 g (2.93 mmol, 74%) of 4.

3α,7α-Dihydroxy-6α-ethyl-23-(tetrazol-5-yl)-6α-ethyl-24-nor-5β-cholane (Compound 15)

To a solution of 4 (0.70 g, 1.43 mmol) in distilled PhMe (15 mL) and under N₂ atmosphere, tributyltin azide (1.97 ml, 7.45 mmol) was added and the resulting mixture was refluxed for 48 hrs. When completed, the reaction mixture was diluted with EtOAc (40 mL), washed with H₂O (3×20 mL), brine (20 mL), dried over anhydrous Na₂SO₄, filtered and concentrated under reduced pressure. The crude 5 (0.80 g) was dissolved in acetone (30 mL) and HCl 3 N (10 mL), and the resulting mixture was stirred at 50° C. for 6 hrs. Acetone was removed under reduced pressure, the residue was diluted with H₂O (20 mL) and basified up to pH 14 by adding aqueous NaOH 3 N. The mixture was washed with Et₂O (3×20 mL), acidified with HCl 3 N, extracted with a solution of CHCl₃/MeOH (95:15, v/v), dried over anhydrous Na₂SO₄ and concentrated under reduced pressure. The residue was purified by silica gel flash chromatography by using an eluent constituted by CHCl₃/MeOH/AcOH (98:2:0.1→94:17:0.1, v/v/v), to give 0.36 g (0.81 mmol, 57% from intermediate 4) of pure Compound 15.

rf: 0.38 (TLC: Silica Gel F₂₅₄S; eluent: CH₂Cl₂/MeOH/AcOH 90:10:1). ¹H-NMR (CD₃OD, 400 MHz) δ: 0.68 (3H, s, 18-CH₃), 0.89-0.93 (6H, m, 19-CH₃+CH₂CH₃), 1.03 (3H, d, J=5.5 Hz, 21-CH₃), 2.87-2.92 (1H, m, 23-CH₂), 2.97-3.00 (1H, m, 23-CH₂), 3.33-3.37 (1H, m, 3-CH), 3.65 (1H, s, 7-CH). ¹³C-NMR (CDCl₃, 100.6 MHz) δ: 12.9, 13.1, 19.6, 21.9, 22.9, 24.4, 24.6, 25.4, 30.2, 32.1, 35.3, 35.4, 36.0, 37.5, 37.6, 41.9, 42.4, 44.0, 44.7, 47.8, 52.5, 58.0, 72.0, 74.1, 159.2.

Example 16: Synthesis of Compound 16

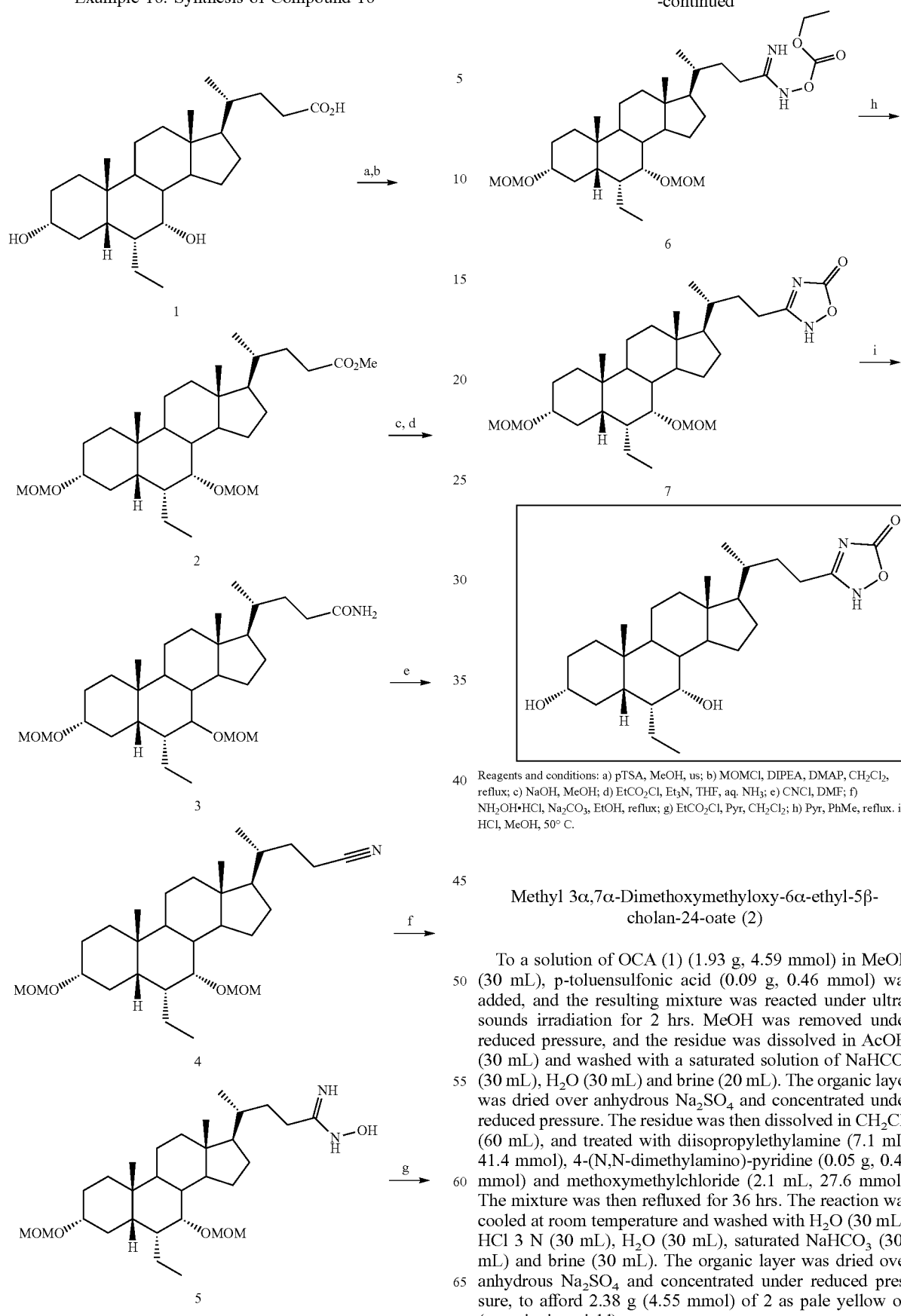

Reagents and conditions: a) pTSA, MeOH, us; b) MOMCl, DIPEA, DMAP, CH$_2$Cl$_2$, reflux; c) NaOH, MeOH; d) EtCO$_2$Cl, Et$_3$N, THF, aq. NH$_3$; e) CNCl, DMF; f) NH$_2$OH·HCl, Na$_2$CO$_3$, EtOH, reflux; g) EtCO$_2$Cl, Pyr, CH$_2$Cl$_2$; h) Pyr, PhMe, reflux. i) HCl, MeOH, 50° C.

Methyl 3α,7α-Dimethoxymethyloxy-6α-ethyl-5β-cholan-24-oate (2)

To a solution of OCA (1) (1.93 g, 4.59 mmol) in MeOH (30 mL), p-toluensulfonic acid (0.09 g, 0.46 mmol) was added, and the resulting mixture was reacted under ultrasounds irradiation for 2 hrs. MeOH was removed under reduced pressure, and the residue was dissolved in AcOEt (30 mL) and washed with a saturated solution of NaHCO$_3$ (30 mL), H$_2$O (30 mL) and brine (20 mL). The organic layer was dried over anhydrous Na$_2$SO$_4$ and concentrated under reduced pressure. The residue was then dissolved in CH$_2$Cl$_2$ (60 mL), and treated with diisopropylethylamine (7.1 mL, 41.4 mmol), 4-(N,N-dimethylamino)-pyridine (0.05 g, 0.46 mmol) and methoxymethylchloride (2.1 mL, 27.6 mmol). The mixture was then refluxed for 36 hrs. The reaction was cooled at room temperature and washed with H$_2$O (30 mL), HCl 3 N (30 mL), H$_2$O (30 mL), saturated NaHCO$_3$ (300 mL) and brine (30 mL). The organic layer was dried over anhydrous Na$_2$SO$_4$ and concentrated under reduced pressure, to afford 2.38 g (4.55 mmol) of 2 as pale yellow oil (quantitative yield).

3α,7α-Dimethoxymethyloxy-6α-ethyl-5β-cholan-24-amide (3)

2 (2.24 g, 4.31 mmol) was treated with 40 mL of a methanolic solution of NaOH 5% at reflux under magnetic stirring for 2 hrs. MeOH was then removed, the residue was dissolved in AcOEt (60 mL) and washed with $H_2O$ (60 mL) and brine (60 mL). The organic layer was dried over anhydrous $Na_2SO_4$ and concentrated under reduced pressure. The oil residue was dissolved in THF (40 mL) and treated with ethyl chloroformiate (0.57 mL, 6.04 mmol) and triethylamine (0.90 mL, 6.47 mmol). The mixture was vigorously stirred for 1 hr. Once the reaction was completed, the mixture was diluted with AcOEt (60 mL), washed with $H_2O$ (30 mL), HCl 1 N (30 mL), brine (30 mL) dried over anhydrous $Na_2SO_4$ and concentrated under reduced pressure, to obtain the desired intermediate 3 in quantitative yield. The crude was used for the next step without further purification.

3α,7α-dimethoxymethyloxy-6α-ethyl-23-cyano-24-nor-5β-cholane (4)

To a solution of 3 (2.01 g, 3.96 mmol) in DMF (40 mL), cyanuric chloride (0.48 g, 7.92 mmol) were added, and the reaction was stirred at room temperature for 16 hrs. The mixture was poured into AcOEt (100 mL), washed with $H_2O$ (5×50 mL) and brine, (30 mL) dried over anhydrous $Na_2SO_4$ and concentrated under reduced pressure. The residue was purified by silica gel flash chromatography with petroleum ether/AcOEt as eluent (9:1→65:35, v/v), to obtain 1.43 g (2.93 mmol, 74%) of 4.

3α,7α-Dimethoxymethyloxy-6α-ethyl-5β-24-N-hydroxy-cholanamidine (5)

To a solution of 4 (0.79 g, 1.61 mmol) in EtOH (45 mL), hydroxylamine chlorohydrate (1.68 g, 24.20 mmol) and sodium carbonate decahydrate (6.92 g, 24.20 mmol) were added and the mixture refluxed for 24 hrs. Volatiles were removed under reduced pressure and the resulting residue was dissolved in EtOAc (50 mL), washed with $H_2O$ (3×50 mL), brine (50 mL), dried over anhydrous $Na_2SO_4$, filtered and concentrated under reduced pressure, to obtain 5 (0.81 g) in nearly quantitative yield. The crude was used as such for the next step.

3α,7α-Dimethoxymethyloxy-6α-ethyl-5β-24-N[(ethoxycarbonyl)oxy]imidocholanamide (6)

To a solution of 5 (0.81 g, 1.61 mmol) in distilled $CH_2Cl_2$ (30 mL), cooled at 0° C. and under $N_2$ atmosphere, ethyl chloroformate (0.20 mL, 2.10 mol) and pyridine (0.19 mL, 2.42 mmol) were added dropwise and the reaction mixture was stirred at room temperature for 1 hr. The reaction was quenched with $H_2O$ (15 mL) and the two phases were separated. The organic layer was thus washed with $H_2O$ (3×15 mL), brine (15 mL), dried over anhydrous $Na_2SO_4$, filtered and concentrated under reduced pressure to afford 6 as crude (0.83 g), which was used for the next step without further purification.

3α,7α-Dimethoxymethyloxy-6α-ethyl-24-nor-5β-23([1,2,4]-oxadiazole-3-one-5yl)-cholane (7)

A solution of crude 6 (0.83 g) in toluene (15 mL) and pyridine (3 mL) was refluxed for 48 hrs. The mixture was diluted with AcOEt (30 mL), washed with $H_2O$ (3×50 mL), brine (30 mL), dried over anhydrous $Na_2SO_4$, filtered and concentrated under reduced pressure, to yield 0.81 g of 7 which was used as such for the next step.

3α,7α-Dihydroxy-6α-ethyl-24-nor-5β-23([1,2,4]-oxadiazole-3-one-5-yl)-cholane (Compound 16)

To a solution of crude 7 (0.81 g) in acetone (15 mL), HCl 3 N (5 mL) was added, and the mixture was stirred at 50° C. for 6 hrs. The organic solvent was removed under reduced pressure, the residue was dissolved in $CH_2Cl_2$ (30 mL) and washed with $H_2O$ (3×30 mL), brine (30 mL), dried over anhydrous $Na_2SO_4$, filtered and concentrated under reduced pressure. The residue was purified by silica gel flash chromatography using a solution of $CH_2Cl_2$/MeOH/AcOH (97:3:0.1→93:7:0.1, v/v/v) as eluent to afford 0.27 g (0.59 mmol, 36% from intermediate 4) of pure Compound 16.

rf: 0.49 (TLC: Silica Gel $F_{254}S$; eluent: $CH_2Cl_2$/MeOH/AcOH 90:10:1). $^1$H-NMR ($CD_3OD$, 400 MHz) δ: 0.70 (3H, s, 18-$CH_3$), 0.90-0.96 (6H, m, 19-$CH_3$+$CH_2CH_3$), 1.02 (3H, d, J=6.1 Hz, 21-$CH_3$), 2.43-2.43 (1H, m, 23-$CH_2$), 2.57-2.64 (1H, m, 23-$CH_2$), 3.29-3.33 (1H, m, 3-CH), 3.66 (1H, s, 7-CH). $^{13}$C-NMR ($CDCl_3$, 100.6 MHz) δ: 12.9, 13.1, 19.6, 22.9, 23.8, 24.4, 24.6, 25.5, 30.2, 32.1, 33.9, 35.3, 35.4, 37.5, 37.6, 37.7, 41.9, 42.5, 44.0, 44.7, 47.8, 52.6, 58.0, 72.0, 74.1, 162.7, 163.2.

Example 17: Synthesis of Compound 17

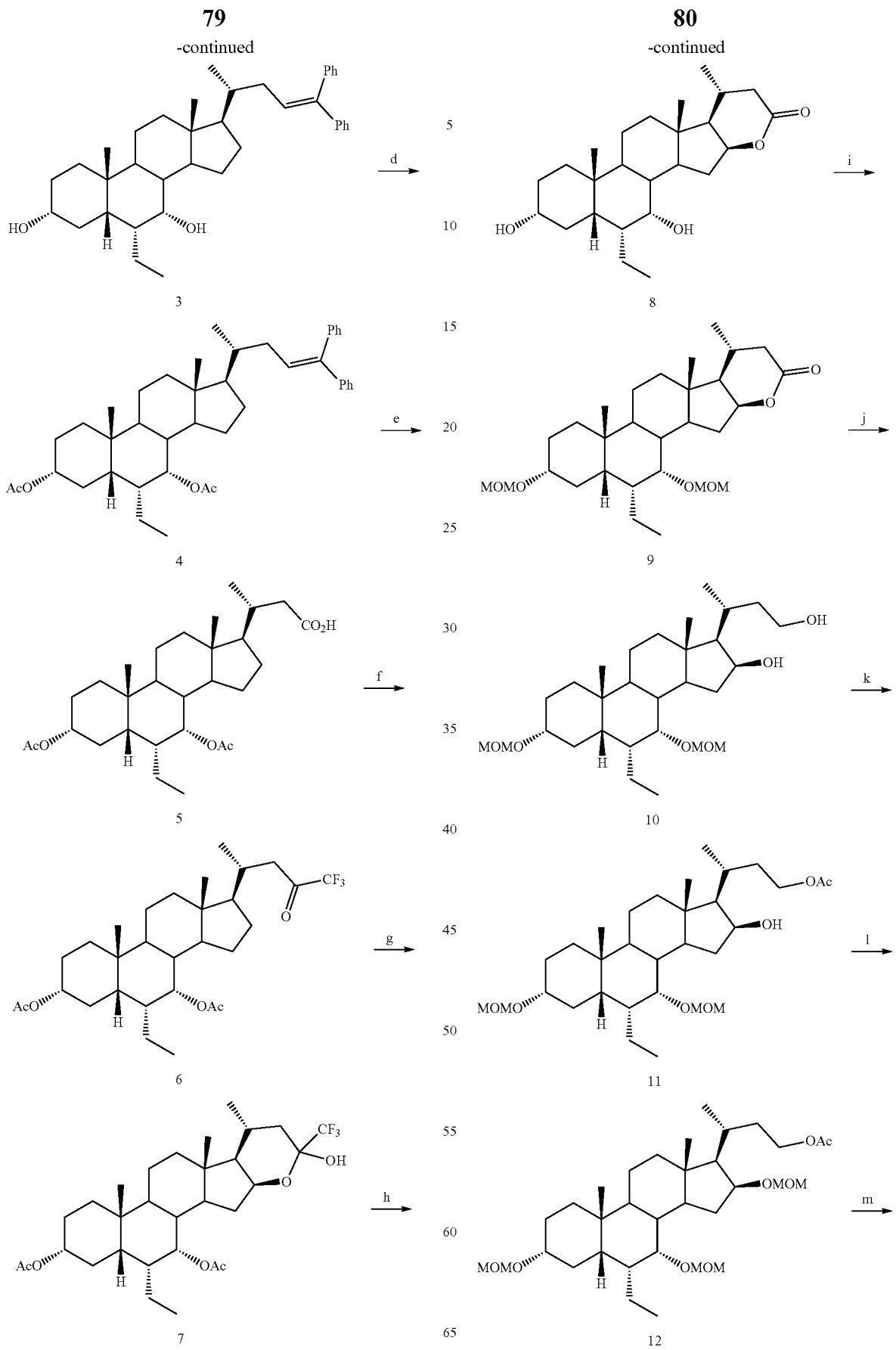

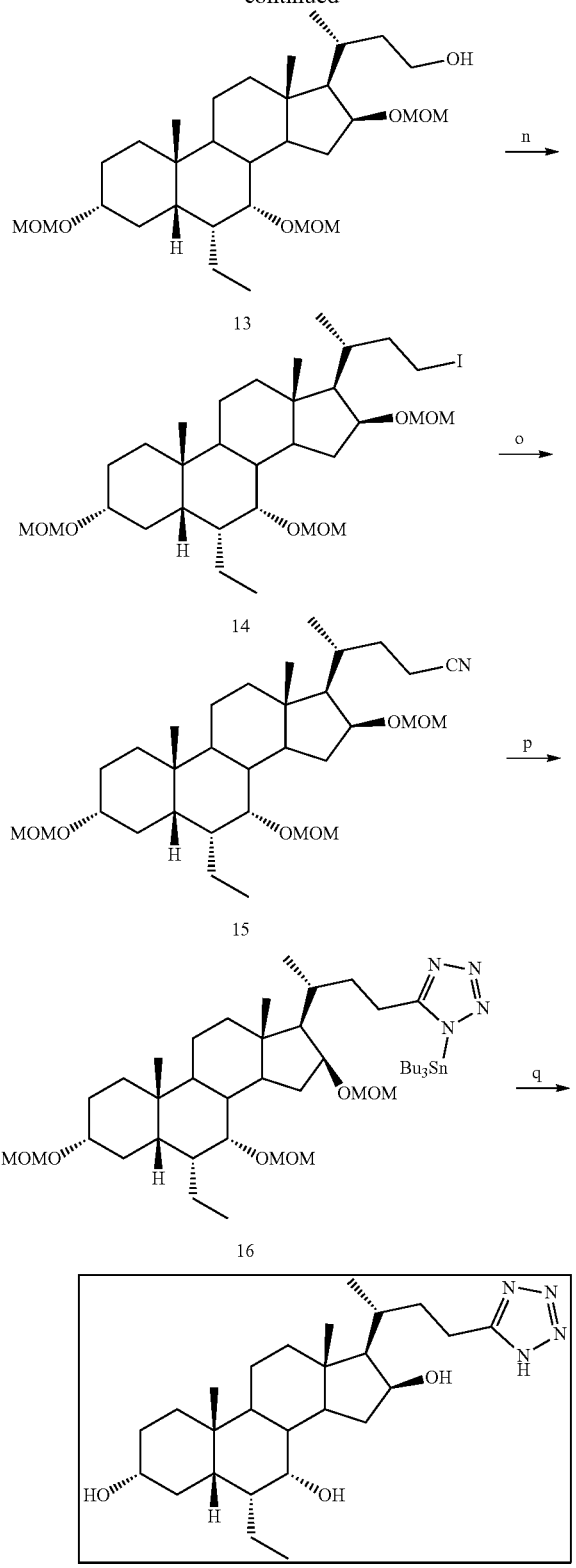

Reagents and conditions: a) pTSA, MeOH, us; b) PhMgBr, THF, reflux; c) EtOH, HCl, 80° C.; d) Ac₂O, Bi(OTf)₃, CH₂Cl₂; e) NaIO₄, H₂SO₄, RuCl₃•H₂O, H₂O, AcOEt, MeCN; f) TFAA, Pyr, PhMe, reflux; g) Oxone, NaHCO₃, EDTA, tBuOH, H₂O, MeCN; h) KOH, MeOH, H₂O, reflux; i) MOMCl, DIPEA, DMAP, CH₂Cl₂, reflux; j) LiAlH₄, THF, 0° C.; k) Ac₂O, Et₃N, CH₂Cl₂; l) MOMCl, DIPEA, DMAP, CH₂Cl₂, reflux; m) NaOH, MeOH, reflux; n) I₂, imidazole, PPh₃, CH₂Cl₂; o) NaCN, PPh₃, DMSO, 80° C.; p) Bu₃SnN₃, PhMe, reflux; q) HCl, MeOH, 45° C..

Methyl 3α,7α-dihydroxy-6α-ethyl-5β-cholanoate (2)

To a solution of OCA (1) (5.0 g, 11.9 mmol) in MeOH (100 mL) p-toluensulfonic acid monohydrate (0.23 g, 1.19 mmol) was added and the mixture was sonicated at room temperature for 90'. The solvent was removed under reduced pressure, the residue was dissolved in CHCl₃ (100 mL), washed with a saturated solution of NaHCO₃ (100 mL), H₂O (100 mL), brine (100 mL), dried over anhydrous Na₂SO₄ and evaporated under reduced pressure. The white solid thus obtained (5.17 g, 11.89 mmol) was used for the next step without further purification.

3α,7α-Dihydroxy-6α-ethyl-24,24-biphenyl-5β-cholan-23-ene (3)

To a solution of methyl 6α-ethyl-3α,7α-dihydroxy-5β-cholanoate (2) (5.17 g, 11.89 mmol) in dry THF (125 mL), phenylmagnesium bromide 3 M in Et₂O (39.6 mL, 118.9 mmol) was added dropwise. The mixture was refluxed for 12 hrs. After cooling at room temperature, the mixture was treated with H₂O (100 mL) and HCl 3 M (100 mL). The mixture was extracted with EtOAc (3×80 mL). The combined organic layers were washed with brine, dried over anhydrous Na₂SO₄ and evaporated under reduced pressure. The crude was dissolved in MeOH (100 mL) and refluxed in the presence of HCl 37% (10 mL) for 1 hr. MeOH was evaporated, the obtained residue was dissolved in EtOAc (120 mL), washed with H₂O (2×100 mL), saturated NaHCO₃ (100 mL), brine (100 mL), dried over anhydrous Na₂SO₄ and evaporated under reduced pressure. The biphenyl derivative 3 was used for the next step without purification.

3α,7α-Diacetoxy-6α-ethyl-24,24-biphenyl-5β-cholan-23-ene (4)

To a solution of 3 (6.42 g, 11.89 mmol) in CH₂Cl₂ (70 mL), acetic anhydride (6.06 g, 59.45 mmol) and bismuth trifluoromethanesulfonate (0.39 g, 0.59 mmol) were added. The resulting mixture was stirred at room temperature for 1 hr. A saturated aqueous solution of NaHCO₃ (50 mL) was then carefully added and the phases were separated. The aqueous layer was extracted with CH₂Cl₂ (2×50 mL). The combined organic layers were washed with H₂O (100 mL), brine (100 mL), dried over anhydrous Na₂SO₄ and concentrated under reduced pressure. The crude was purified by silica gel flash chromatography using an eluent constituted by petroleum ether/EtOAc (95:5→7:3, v/v) obtaining 5.56 g (8.91 mmol, 75%) of desired intermediate 4.

3α,7α-Diacetoxy-6α-ethyl-24-nor-5β-cholan-23-oic acid (5)

To a suspension of sodium periodate (21.13 g, 98.73 mmol) in H₂O (20 mL), H₂SO₄ 2 N in H₂O (3.22 mL) was added and the mixture was stirred at room temperature for 1 hr. The mixture was cooled to 0° C. and treated with ruthenium trichloride hydrate (0.11 g, 0.55 mmol) which was added in one portion. After 1 hr, acetonitrile (31 mL) was added to the solution and after additional 5', a solution of biphenyl derivative 4 (6.85 g, 10.97 mmol) in EtOAc (43 mL) was added. The mixture was stirred at room temperature for 1 hr. The white solid thus formed was filtered off, then the liquor was poured into H₂O (100 mL) and extracted with EtOAc (3×50 mL). The combined organic layers were filtered through a Celite pad, washed with a saturated solution of $Na_2S_2O_3$ in $H_2O$ (100 mL), brine (100 mL), dried over anhydrous $Na_2SO_4$ and concentrated under reduced pressure. The residue was purified by silica gel flash chromatography eluting with EtOAc in petroleum ether from 10 to 50%. The desired acid 5 was obtained as white solid (5.27 g, 10.75 mmol, 98%).

3α,7α-Diacetoxy-6α-ethyl-23-oxo-24,24,24-trifluoromethyl-5β-cholane (6)

To a solution of 5 (14.20 g, 28.98 mmol) in toluene (125 mL) cooled at 0° C., pyridine (11.44 g, 144.90 mmol) and trifluoroacetic anhydride (30.43 g, 144.90 mmol) were added. The mixture was refluxed for 18 hrs. After cooling at room temperature, the dark mixture was treated with $H_2O$ (120 mL) at 45° C. for 1 hr, cooled at room temperature and acidified by the careful addition of HCl 1 N (100 mL). The mixture was then extracted with AcOEt (3×80 mL), the collected organic layers were washed with brine (100 mL), dried over anhydrous $Na_2SO_4$, filtered under vacuum and concentrated under reduced pressure. The brown oil residue was filtered through a silica gel pad (h: 10 cm, φ: 4 cm), collecting the crude with petroleum ether/AcOEt (8:2, v/v) and obtaining the desired trifluoromethyl ketone 6 as pale yellow solid (15.7 g), which was used for the next step without further purification.

3α,7α-Diacetoxy-6α-ethyl-23-lactol Derivative (7)

To a solution of crude 6 (15.7 g) in acetonitrile (415 mL) in a flask equipped with mechanical stirring and repaired from light, $^t$BuOH (135 mL) and EDTA (170 mg, 0.584 mmol) dissolved in $H_2O$ (395 mL) were added. $NaHCO_3$ (36.79 g, 438.00 mmol) and oxone (89.64 g, 146.00 mmol) were added portionwise, and the resulting suspension was vigorously stirred for 18 hrs. The mixture was filtered to remove the solid, diluted with brine (100 mL) and extracted with $Et_2O$ (3×150 mL). The combined organic layers were washed with brine (150 mL), dried over anhydrous $Na_2SO_4$ and concentrated under reduced pressure. The residue was filtered through a silica gel pad (h: 12 cm, φ: 5 cm), collecting the crude with petroleum ether/AcOEt (9:1, v/v). 9.60 g of desired lactol 7 were obtained. The crude material was used as such for the next step.

3α,7α-Diacetoxy-6α-ethyl-23-lactone Derivative (8)

To a solution of 7 (9.60 g, 17.20 mmol) in MeOH (50 mL), a solution of aqueous KOH 10 M (25.8 mL, 258.0 mmol) was added and the mixture was stirred at reflux for 18 hrs. MeOH was removed under reduced pressure, $H_2O$ (25 mL) was added and the resulting mixture was refluxed for additional 24 hrs. After cooling at room temperature, the mixture was washed with $Et_2O$ (3×50 mL), acidified with HCl 3 N and extracted with $CHCl_3$ (3×150 mL). The collected organic layers were dried over anhydrous $Na_2SO_4$ and concentrated under reduced pressure. The residue was purified by silica gel flash chromatography eluting with an isocratic solution of $CHCl_3$/MeOH/AcOH (97:3:0.1, v/v). After removal of solvent, 5.70 g (mmol, 48% from intermediate 5) of desired intermediate 8 were obtained.

3α,7α-Dimethoxymethyloxy-6α-ethyl-23-lactone Derivative (9)

To a solution of lactone 8 (1.75 g, 4.33 mmol) in $CH_2Cl_2$ (30 mL), diisopropylethylamine (5.03 g, 38.98 mmol), dimethylaminopyridine (0.05 g, 0.43 mmol) and chloromethyl methyl ether (2.08 g, 25.99 mmol) were sequentially added, and the mixture was refluxed for 48 hrs. The reaction was quenched by adding $H_2O$ (30 mL) and the two phases were separated. The organic phase was washed with HCl 1 N (30 mL), with a saturated solution of $NaHCO_3$ (30 mL), brine (50 mL), dried over anhydrous $Na_2SO_4$, filtered under vacuum and concentrated under reduced pressure. The protected derivative 9 was used for the following step without further purification.

3α,7α-Dimethoxymethyloxy-6α-ethyl-16β,23-dihydroxy-24-nor-5β-cholane (10)

To a suspension of $LiAlH_4$ (0.49 g, 12.99 mmol) in THF (30 mL) cooled at 0° C., a solution of 9 (2.13 g, 4.33 mmol) in THF (20 mL) was added dropwise. The reaction was stirred for 30'. $Na_2SO_4$ decahydrate was slowly and cautiously added portionwise, until the hydrogen liberation disappeared. The mixture was filtered under vacuum washing the solid residue with AcOEt (5×5 mL); the collected organic phases were concentrated under reduced pressure, to afford 1.91 g (3.86 mmol, 89%) of the desired tetrahydroxy bile derivative 10 which was for the next step without further purification.

3α,7α-Dimethoxymethyloxy-6α-ethyl-16β-hydroxy-23-acetoxy-24-nor-5β-cholane (11)

To a solution of 10 (1.42 g, 2.86 mmol) in $CH_2Cl_2$ (120 mL), $Ac_2O$ (0.81 mL, 8.59 mmol) and $Et_3N$ (1.81 mL, 12.88 mmol) were added, and the resulting solution was stirred at room temperature for 12 hrs. The mixture was poured into a saturated solution of $NaHCO_3$ (100 mL) and extracted with $CH_2Cl_2$ (2×60 mL). The combined organic layers were washed with $H_2O$ (100 mL), brine (100 mL), dried over anhydrous $Na_2SO_4$ and concentrated under reduced pressure. The crude 11 (1.46 g) was used as such for the next step.

3α,7α,16β-Trimethoxymethyloxy 6α-ethyl-23-acetoxy-24-nor-5β-cholane (12)

To a solution of 11 (1.46 g, about 2.86 mmol) in $CH_2Cl_2$ (50 mL), diisopropylethylamine (1.97 mL, 11.45 mmol), dimethylaminopyridine (0.03 g, 0.27 mmol) and chloromethyl methyl ether (0.65 mL, 8.59 mmol) were sequentially added. The mixture was refluxed for 5 hrs. The reaction was quenched by adding $H_2O$ (30 mL) and the two phases were separated. The organic phase was washed with HCl 1 N (30 mL), with a saturated solution of $NaHCO_3$ (30 mL), brine (50 mL), dried over anhydrous $Na_2SO_4$ and concentrated under reduced pressure. The derivative 12 (1.51 g) was used for the following step without further purification.

3α,7α,16β-Trimethoxymethyloxy-6α-ethyl-23-hydroxy-24-nor-5β-cholane (13)

To a solution of 12 (1.51 g, about 2.86 mmol) in MeOH (50 mL), NaOH (0.57 g, 14.31 mmol) was added and the mixture was refluxed for 3 hrs. The reaction was cooled at room temperature and the solvent was removed under reduced pressure. The crude was dissolved in $CH_2Cl_2$ (50 mL), washed with $H_2O$ (50 mL), brine (50 mL), dried over anhydrous $Na_2SO_4$ and evaporated under reduced pressure. The residue was purified by silica gel flash chromatography eluting with ethyl acetate in petroleum ether (from 5 to 30%)

obtaining the desired compound 13 (1.35 g, 2.49 mmol, 87% from intermediate 10) as pale yellow oil.

3α,7α,16β-Trimethoxymethyloxy-6α-ethyl-23-iodio-24-nor-5β-cholane (14)

To a solution of triphenylphosphine (4.6 g, 17.56 mmol) in $CH_2Cl_2$ (50 mL), iodine (2.05 g, 16.18 mmol) was added. After 10', imidazole (1.16 g, 17.10 mmol) was added to the solution. After additional 15', a solution of alcohol 13 (1.25 g, 2.31 mmol) in $CH_2Cl_2$ (50 mL) was added and the resulting mixture was stirred at room temperature for 48 hrs. The reaction was then poured into $H_2O$ (100 mL), the phases were separated and the aqueous phase was extracted with $CH_2Cl_2$ (2×60 mL). The combined organic layers were washed with brine (100 mL), dried over anhydrous $Na_2SO_4$ and evaporated under reduced pressure. The crude was purified by silica gel flash chromatography eluting with ethyl acetate in petroleum ether (from 5 to 20%) yieding 1.05 g (1.65 mmol, 71%) of the desired pure iodo derivative 14.

3α,7α,16β-Trimethoxymethyloxy-6α-ethyl-23-cyano-24-nor-5β-cholane (15)

To a solution of iodo derivative 14 (1.03 g, 1.58 mmol) in DMSO (15 mL), sodium cyanide (0.09 g, 1.90 mmol) was added and the mixture was stirred at 80° C. for 3 hrs. The mixture was then allowed to cool to room temperature, diluted with $CH_2Cl_2$ (100 mL), washed with a saturated solution of $NaHCO_3$ (50 mL), $H_2O$ (50 mL), brine (50 mL), dried over anhydrous $Na_2SO_4$ and concentrated under reduced pressure. The mixture was purified by silica gel flash chromatography eluting with ethyl acetate in petroleum ether (from 10 to 30%) to give 0.80 g (1.45 mmol, 92%) of pure 15.

3α,7α,16β-Trimethoxymethyloxy-6α-ethyl-23-[1-(tributylstannyl)-tetrazol-5-yl]-24-nor-5β-cholane (16)

A solution of nitrile 15 (0.68 g, 1.14 mmol) in toluene (12 mL) was refluxed with azidotributyltin(IV) (1.91 g, 5.72 mmol) for 36 hrs. The mixture was cooled at room temperature, diluted with EtOAc (15 mL), washed with $H_2O$ (50 mL), brine (50 mL), dried over anhydrous $Na_2SO_4$ and concentrated under reduced pressure. The residue (0.82 g) was used for the following step without further purification.

3α,7α,16β-Trihydroxy-6α-ethyl-23-(tetrazol-5-yl)-24-nor-5β-cholane (Compound 17)

To a solution of crude 16 (0.80 g) in MeOH (20 mL), HCl 3 N (5 mL) was added and the mixture was stirred at 50° C. for 48 hrs. The mixture was cooled at room temperature and treated with then NaOH 3 N (7 mL). Ufter evaporation of the solvent, the crude residue was dissolved into $H_2O$ (50 mL) and washed with $Et_2O$ (3×40 mL). The aqueous phase was then acidified up to pH=1 with HCl 3 N and extracted with a mixture of EtOAc/MeOH (9:1, v/v, 3×50 mL). The combined organic layers were washed with brine (100 mL), dried over anhydrous $Na_2SO_4$ and concentrated under reduced pressure. The mixture was purified by silica gel flash chromatography eluting with methanol in chloroform (from 1 to 10%) in the presence of 0.1% of AcOH. 0.28 g of the final compound Compound 17 were obtained as white solid (54% from intermediate 15).

rf: 0.53 (TLC: Silica Gel 60 $F_{254}S$; eluent: $CHCl_3$/MeOH/AcOH 90:10:1). $^1$H-NMR (CD$_3$OD, 400 MHz) δ: 0.87-0.93 (9H, m, 18-CH$_3$+19-CH$_3$+CH$_2$CH$_3$), 1.07 (3H, d, J=6.2 Hz, 21-CH$_3$), 2.12-2.17 (1H, m, 22-CH$_2$), 2.37-2.41 (1H, m, 22-CH$_2$), 2.91-3.08 (2H, m, 23-CH$_2$), 3.31-3.35 (1H, m, 3-CH), 3.66 (1H, s, 7-CH), 4.40-4.44 (1H, m, 16-CH). $^{13}$C-NMR (CDCl$_3$, 100.6 MHz) δ: 10.5, 11.8, 16.9, 19.9, 20.1, 22.0, 22.2, 29.5, 29.7, 32.7, 32.8, 33.0, 35.1 (×2), 35.4, 39.5, 39.6, 41.6, 42.0, 45.4, 48.0, 61.1, 69.5, 71.6 (×2), 157.1.

Example 18: Synthesis of Compound 18

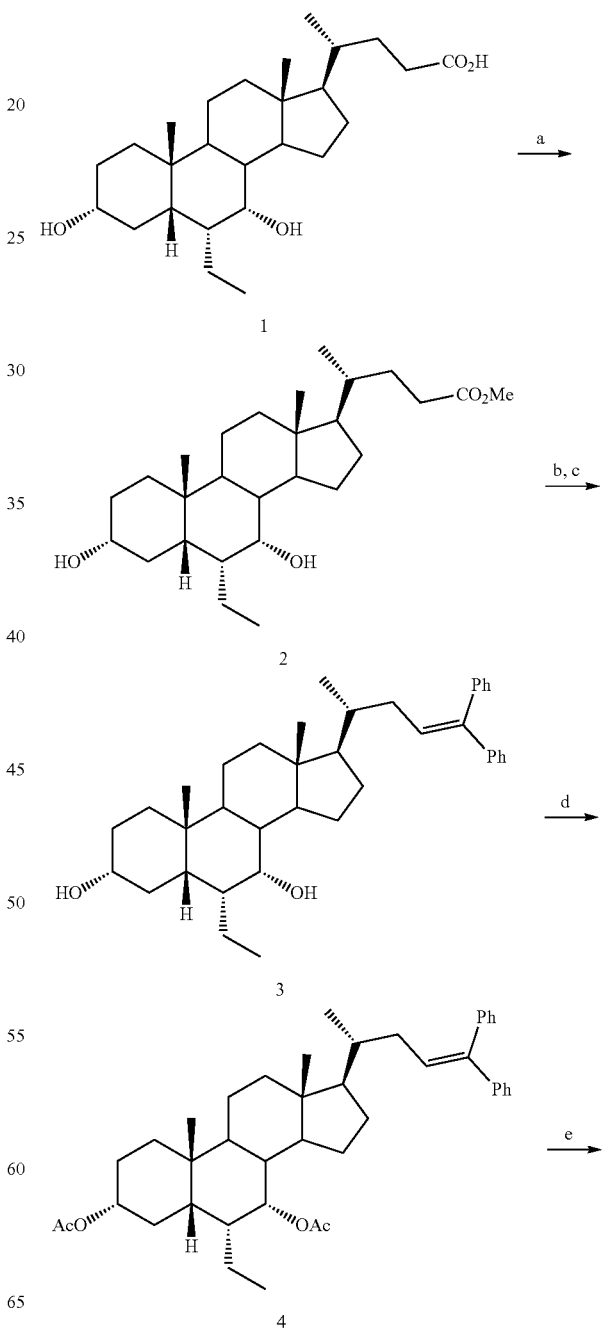

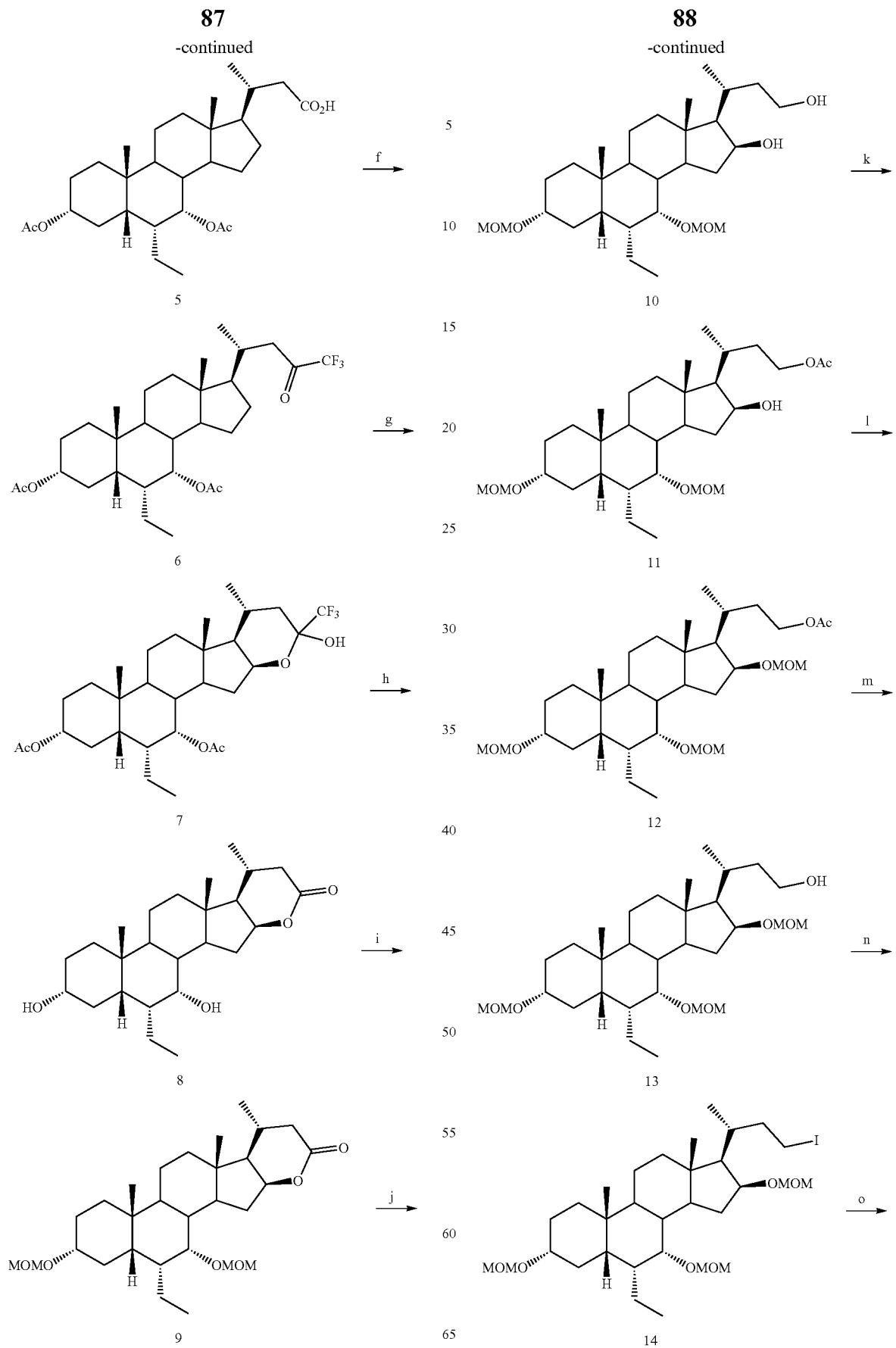

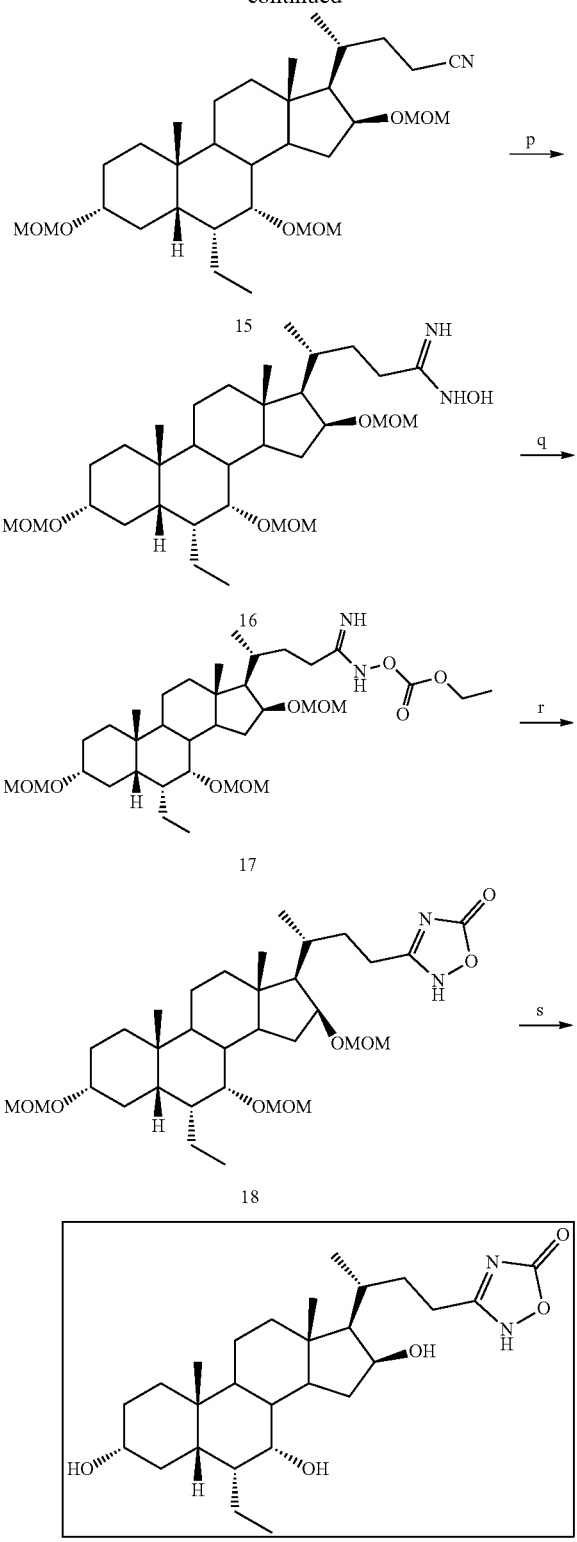

Reagents and conditions: a) pTSA, MeOH, us; b) PhMgBr, THF, reflux; c) EtOH, HCl, 80° C.; d) Ac₂O, Bi(OTf)₃, CH₂Cl₂; e) NaIO₄, H₂SO₄, RuCl₃•H₂O, H₂O, AcOEt, MeCN; f) TFAA, Pyr, PhMe, reflux; g) Oxone, NaHCO₃, EDTA, tBuOH, H₂O, MeCN; h) KOH, MeOH, H₂O, reflux; i) MOMCl, DIPEA, DMAP, CH₂Cl₂, reflux; j) LiAlH₄, THF, 0° C.; k) Ac₂O, Et₃N, CH₂Cl₂; l) MOMCl, DIPEA, DMAP, CH₂Cl₂, reflux; m) NaOH, MeOH, reflux; n) I₂, imidazole, PPh₃, CH₂Cl₂; o) NaCN, PPh₃, DMSO, 80° C.; p) NH₂OH•HCl, Na₂CO₃, EtOH, reflux; q) EtCO₂Cl, Pyr, CH₂Cl₂; r) Pyr, PhMe, reflux; s) HCl, MeOH, 45° C..

Methyl 3α,7α-dihydroxy-6α-ethyl-5β-cholanoate (2)

To a solution of OCA (1) (5.0 g, 11.9 mmol) in MeOH (100 mL) p-toluensulfonic acid monohydrate (0.23 g, 1.19 mmol) was added and the mixture was sonicated at room temperature for 90'. The solvent was removed under reduced pressure, the residue was dissolved in CHCl₃ (100 mL), washed with a saturated solution of NaHCO₃ (100 mL), H₂O (100 mL), brine (100 mL), dried over anhydrous Na₂SO₄ and evaporated under reduced pressure. The white solid thus obtained (5.17 g, 11.89 mmol) was used for the next step without further purification.

3α,7α-Dihydroxy-6α-ethyl-24,24-biphenyl-5β-cholan-23-ene (3)

To a solution of methyl 6α-ethyl-3α,7α-dihydroxy-5β-cholanoate (2) (5.17 g, 11.89 mmol) in dry THF (125 mL), phenylmagnesium bromide 3 M in Et₂O (39.6 mL, 118.9 mmol) was added dropwise. The mixture was refluxed for 12 hrs. After cooling at room temperature, the mixture was treated with H₂O (100 mL) and HCl 3 M (100 mL). The mixture was extracted with EtOAc (3×80 mL), the combined organic layers were washed with brine, dried over anhydrous Na₂SO₄ and evaporated under reduced pressure. The crude was dissolved in MeOH (100 mL) and refluxed in the presence of HCl 37% (10 mL) for 1 hr. MeOH was evaporated, the obtained residue was dissolved in EtOAc (120 mL), washed with H₂O (2×100 mL), saturated NaHCO₃ (100 mL), brine (100 mL), dried over anhydrous Na₂SO₄ and evaporated under reduced pressure. The biphenyl derivative 3 was used for the next step without purification.

3α,7α-Diacetoxy-6α-ethyl-24,24-biphenyl-5β-cholan-23-ene (4)

To a solution of 3 (6.42 g, 11.89 mmol) in CH₂Cl₂ (70 mL), acetic anhydride (6.06 g, 59.45 mmol) and bismuth trifluoromethanesulfonate (0.39 g, 0.59 mmol) were added. The resulting mixture was stirred at room temperature for 1 hr. A saturated aqueous solution of NaHCO₃ (50 mL) was then carefully added and the phases were separated. The aqueous layer was extracted with CH₂Cl₂ (2×50 mL). The combined organic layers were washed with H₂O (100 mL), brine (100 mL), dried over anhydrous Na₂SO₄ and concentrated under reduced pressure. The crude was purified by silica gel flash chromatography using an eluent constituted by petroleoum ether/EtOAc (95:5→7:3, v/v) obtaining 5.56 g (8.91 mmol, 75%) of desired intermediate 4.

3α,7α-Diacetoxy-6α-ethyl-24-nor-5β-cholan-23-oic acid (5)

To a suspension of sodium periodate (21.13 g, 98.73 mmol) in H₂O (20 mL), H₂SO₄ 2 N in H₂O (3.22 mL) was added and the mixture was stirred at room temperature for 1 hr. The mixture was cooled to 0° C. and treated with ruthenium trichloride hydrate (0.11 g, 0.55 mmol) which was added in one portion. After 1 hr, acetonitrile (31 mL) was added to the solution and after additional 5', a solution of biphenyl derivative 4 (6.85 g, 10.97 mmol) in EtOAc (43 mL) was added. The mixture was stirred at room temperature for 1 hr. The white solid thus formed was filtered off, then the liquor was poured into H₂O (100 mL) and extracted with EtOAc (3×50 mL). The combined organic layers were filtered through a Celite pad, washed with a saturated solution of Na$_2$S$_2$O$_3$ in H$_2$O (100 mL), brine (100 mL), dried over anhydrous Na$_2$SO$_4$ and concentrated under reduced pressure. The residue was purified by silica gel flash chromatography eluting with EtOAc in petroleum ether from 10 to 50%. The desired acid 5 was obtained as white solid (5.27 g, 10.75 mmol, 98%).

3α,7α-Diacetoxy-6α-ethyl-23-oxo-24,24,24-trifluoromethyl-5β-cholane (6)

To a solution of 5 (14.20 g, 28.98 mmol) in toluene (125 mL) cooled at 0° C., pyridine (11.44 g, 144.90 mmol) and trifluoroacetic anhydride (30.43 g, 144.90 mmol) were added. The mixture was refluxed for 18 hrs. After cooling at room temperature, the dark mixture was treated with H$_2$O (120 mL) at 45° C. for 1 hr, cooled at room temperature and acidified by the careful addition of HCl 1 N (100 mL). The mixture was then extracted with AcOEt (3×80 mL), the collected organic layers were washed with brine (100 mL), dried over anhydrous Na$_2$SO$_4$, filtered under vacuum and concentrated under reduced pressure. The brown oil residue was filtered through a silica gel pad (h: 10 cm, φ: 4 cm), collecting the crude with petroleum ether/AcOEt (8:2, v/v) and obtaining the desired trifluoromethyl ketone 6 as pale yellow solid (15.7 g), which was used for the next step without further purification.

3α,7α-Diacetoxy-6α-ethyl-23-lactol Derivative (7)

To a solution of crude 6 (15.7 g) in acetonitrile (415 mL) in a flask equipped with mechanical stirring and repaired from light, $^t$BuOH (135 mL) and EDTA (170 mg, 0.584 mmol) dissolved in H$_2$O (395 mL) were added. NaHCO$_3$ (36.79 g, 438.00 mmol) and oxone (89.64 g, 146.00 mmol) were added portionwise, and the resulting suspension was vigorously stirred for 18 hrs. The mixture was filtered to remove the solid, diluted with brine (100 mL) and extracted with Et$_2$O (3×150 mL). The combined organic layers were washed with brine (150 mL), dried over anhydrous Na$_2$SO$_4$ and concentrated under reduced pressure. The residue was filtered through a silica gel pad (h: 12 cm, φ: 5 cm), collecting the crude with petroleum ether/AcOEt (9:1, v/v). 9.60 g of desired lactol 7 were obtained. The crude material was used as such for the next step.

3α,7α-Diacetoxy-6α-ethyl-23-lactone Derivative (8)

To a solution of 7 (9.60 g, 17.20 mmol) in MeOH (50 mL), a solution of aqueous KOH 10 M (25.8 mL, 258.0 mmol) was added and the mixture was stirred at reflux for 18 hrs. MeOH was removed under reduced pressure, H$_2$O (25 mL) was added and the resulting mixture was refluxed for additional 24 hrs. After cooling at room temperature, the mixture was washed with Et$_2$O (3×50 mL), acidified with HCl 3 N and extracted with CHCl$_3$ (3×150 mL). The collected organic layers were dried over anhydrous Na$_2$SO$_4$ and concentrated under reduced pressure. The residue was purified by silica gel flash chromatography eluting with an isocratic solution of CHCl$_3$/MeOH/AcOH (97:3:0.1, v/v). After removal of solvent, 5.70 g (mmol, 48% from intermediate 5) of desired intermediate 8 were obtained.

3α,7α-Dimethoxymethyloxy-6α-ethyl-23-lactone Derivative (9)

To a solution of lactone 8 (1.75 g, 4.33 mmol) in CH$_2$Cl$_2$ (30 mL), diisopropylethylamine (5.03 g, 38.98 mmol), dim-ethylaminopyridine (0.05 g, 0.43 mmol) and chloromethyl methyl ether (2.08 g, 25.99 mmol) were sequentially added, and the mixture was refluxed for 48 hrs. The reaction was quenched by adding H$_2$O (30 mL) and the two phases were separated. The organic phase was washed with HCl 1 N (30 mL), with a saturated solution of NaHCO$_3$ (30 mL), brine (50 mL), dried over anhydrous Na$_2$SO$_4$, filtered under vacuum and concentrated under reduced pressure. The protected derivative 9 was used for the following step without further purification.

3α,7α-Dimethoxymethyloxy-6α-ethyl-16β,23-dihydroxy-24-nor-5β-cholane (10)

To a suspension of LiAlH$_4$ (0.49 g, 12.99 mmol) in THF (30 mL) cooled at 0° C., a solution of 9 (2.13 g, 4.33 mmol) in THF (20 mL) was added dropwise. The reaction was stirred for 30'. Na$_2$SO$_4$ decahydrate was slowly and cautiously added portionwise, until the hydrogen liberation disappeared. The mixture was filtered under vacuum washing the solid residue with AcOEt (5×5 mL); the collected organic phases were concentrated under reduced pressure, to afford 1.91 g (3.86 mmol, 89%) of the desired tetrahydroxy bile derivative 10 which was for the next step without further purification.

3α,7α-Dimethoxymethyloxy-6α-ethyl-16β-hydroxy-23-acetoxy-24-nor-5β-cholane (11)

To a solution of 10 (1.42 g, 2.86 mmol) in CH$_2$Cl$_2$ (120 mL), Ac$_2$O (0.81 mL, 8.59 mmol) and Et$_3$N (1.81 mL, 12.88 mmol) were added, and the resulting solution was stirred at room temperature for 12 hrs. The mixture was poured into a saturated solution of NaHCO$_3$ (100 mL) and extracted with CH$_2$Cl$_2$ (2×60 mL). The combined organic layers were washed with H$_2$O (100 mL), brine (100 mL), dried over anhydrous Na$_2$SO$_4$ and concentrated under reduced pressure. The crude 11 (1.46 g) was used as such for the next step.

3α,7α,16β-Trimethoxymethyloxy 6α-ethyl-23-acetoxy-24-nor-5β-cholane (12)

To a solution of 11 (1.46 g, about 2.86 mmol) in CH$_2$Cl$_2$ (50 mL), diisopropylethylamine (1.97 mL, 11.45 mmol), dimethylaminopyridine (0.03 g, 0.27 mmol) and chloromethyl methyl ether (0.65 mL, 8.59 mmol) were sequentially added. The mixture was refluxed for 5 hrs. The reaction was quenched by adding H$_2$O (30 mL) and the two phases were separated. The organic phase was washed with HCl 1 N (30 mL), with a saturated solution of NaHCO$_3$ (30 mL), brine (50 mL), dried over anhydrous Na$_2$SO$_4$ and concentrated under reduced pressure. The derivative 12 (1.51 g) was used for the following step without further purification.

3α,7α,16β-Trimethoxymethyloxy-6α-ethyl-23-hydroxy-24-nor-5β-cholane (13)

To a solution of 12 (1.51 g, about 2.86 mmol) in MeOH (50 mL), NaOH (0.57 g, 14.31 mmol) was added and the mixture was refluxed for 3 hrs. The reaction was cooled at room temperature and the solvent was removed under reduced pressure. The crude was dissolved in CH$_2$Cl$_2$ (50 mL), washed with H$_2$O (50 mL), brine (50 mL), dried over anhydrous Na$_2$SO$_4$ and evaporated under reduced pressure. The residue was purified by silica gel flash chromatography eluting with ethyl acetate in petroleum ether (from 5 to 30%)

obtaining the desired compound 64 (1.35 g, 2.49 mmol, 87% from intermediate 10) as pale yellow oil.

3α,7α,1613-Trimethoxymethyloxy-6α-ethyl-23-iodio-24-nor-5β-cholane (14)

To a solution of triphenylphosphine (4.6 g, 17.56 mmol) in CH$_2$Cl$_2$ (50 mL), iodine (2.05 g, 16.18 mmol) was added. After 10', imidazole (1.16 g, 17.10 mmol) was added to the solution. After additional 15', a solution of alcohol 13 (1.25 g, 2.31 mmol) in CH$_2$Cl$_2$ (50 mL) was added and the resulting mixture was stirred at room temperature for 48 hrs. The reaction was then poured into H$_2$O (100 mL), the phases were separated and the aqueous phase was extracted with CH$_2$Cl$_2$ (2×60 mL). The combined organic layers were washed with brine (100 mL), dried over anhydrous Na$_2$SO$_4$ and evaporated under reduced pressure. The crude was purified by silica gel flash chromatography eluting with ethyl acetate in petroleum ether (from 5 to 20%) yielding 1.05 g (1.65 mmol, 71%) of the desired pure iodo derivative 14.

3α,7α,16β-Trimethoxymethyloxy-6α-ethyl-23-cyano-24-nor-5β-cholane (15)

To a solution of iodo derivative 14 (1.03 g, 1.58 mmol) in DMSO (15 mL), sodium cyanide (0.09 g, 1.90 mmol) was added and the mixture was stirred at 80° C. for 3 hrs. The mixture was then allowed to cool to room temperature, diluted with CH$_2$Cl$_2$ (100 mL), washed with a saturated solution of NaHCO$_3$ (50 mL), H$_2$O (50 mL), brine (50 mL), dried over anhydrous Na$_2$SO$_4$ and concentrated under reduced pressure. The mixture was purified by silica gel flash chromatography eluting with ethyl acetate in petroleum ether (from 10 to 30%) to give 0.80 g (1.45 mmol, 92%) of pure 15.

3α,7α,16β-Trimethoxymethyloxy-6α-ethyl-5β-24-N-hydroxy-cholanamidine (16)

To a solution of 15 (0.16 g, 0.29 mmol) in ethanol (15 mL), sodium carbonate decahydrate (1.25 g, 4.36 mmol) and hydroxylamine hydrochloride (0.30 g, 4.36 mmol) were added. The resulting mixture was refluxed for 18 hrs. The solvent was removed under reduced pressure, the crude was dissolved in CH$_2$Cl$_2$ (30 mL), washed with H$_2$O (30 mL), brine (30 mL), dried over anhydrous Na$_2$SO$_4$ and evaporated under reduced pressure. The residue (0.17 g) was used as such for the following step.

3α,7α,16β-Trimethoxymethyloxy-6α-ethyl-5β-24-N-[(ethoxycarbonyl)oxy]imido cholanamide (17)

To a solution of crude hydroxyamidine 16 (0.17 g, 0.29 mmol) in CH$_2$Cl$_2$ (10 mL), ethylchloroformate (0.04 g, 0.38 mmol) and pyridine (0.03 g, 0.44 mmol) were added at 0° C. The mixture was stirred at room temperature for 1 hr. The reaction was quenched by adding H$_2$O (15 mL). The phases were separated and the water phase was extracted with CH$_2$Cl$_2$ (2×15 mL). The combined organic layers were washed with brine (30 mL), dried over anhydrous Na$_2$SO$_4$ and evaporated under reduced pressure. The crude residue (0.18 g) was used for the following step without further purification.

3α,7α,16β-Trimethoxymethyloxy-6α-ethyl-24-nor-5β-23-([1,2,4]-oxadiazole-3-one-5yl)-cholane (18)

A solution of crude 17 (0.18 g, 0.29 mmol) in toluene (5 mL) was refluxed in the presence of pyridine (1 mL) for 48 hrs. The reaction was diluted with EtOAc (20 mL), washed with H$_2$O (30 mL) and HCl 3 N (30 mL), with a saturated solution of NaHCO$_3$ (30 mL), brine (50 mL), dried over anhydrous Na$_2$SO$_4$ and concentrated under reduced pressure. The derivative 18 (0.17 g) was used for the following step without further purification.

3α,7α16β-Trihydroxy-6α-ethyl-24-nor-5β-23-([1,2,4]-oxadiazole-3-one-5yl)-cholane (Compound 18)

To a solution of crude compound 18 (0.19 g) in acetone (5 mL), HCl 3 N (1 mL) was added and the mixture was stirred at 35° C. for 48 hrs. The solvent was evaporated under reduced pressure, suspended in H$_2$O (10 mL) and extracted with CH$_2$Cl$_2$ (2×10 mL). The combined organic layers were washed with H$_2$O (10 mL), brine (10 mL), dried over anhydrous Na$_2$SO$_4$ and evaporated under reduced pressure. The mixture was purified by silica gel flash chromatography using a solution of methanol in chloroform (from 1 to 10%) in the presence of 0.1% of AcOH. Evaporation of the solvent afforded 11 mg of Compound 18 (8% yield from 13) as white solid.

rf: 0.51 (TLC: Silica Gel 60 F$_{254}$S; eluent: CHCl$_3$/MeOH/AcOH 90:10:1). $^1$H-NMR (CD$_3$OD, 400 MHz) δ: 0.87-0.93 (9H, m, 18-CH$_3$+19-CH$_3$+CH$_2$CH$_3$), 1.03 (3H, d, J=6.4 Hz, 21-CH$_3$), 2.36-2.32 (1H, m, 22-CH$_2$), 2.50-2.57 (1H, m, 23-CH$_2$), 2.63-2.67 (1H, m, 23-CH$_2$), 3.25-3.33 (1H, m, 3-CH), 3.65 (1H, s, 7-CH), 4.33-4.37 (1H, m, 16-CH). $^{13}$C-NMR (CDCl$_3$, 100.6 MHz) δ: 10.9, 12.2, 17.2, 20.5, 22.1, 22.4, 22.6, 30.0, 30.1, 31.5, 33.2, 33.4, 35.5 (×2), 36.0, 39.9, 40.0, 42.0, 42.5, 45.8, 61.3, 70.0, 71.8, 72.0, 160.8, 161.1.

Example 19: Synthesis of Compound 19

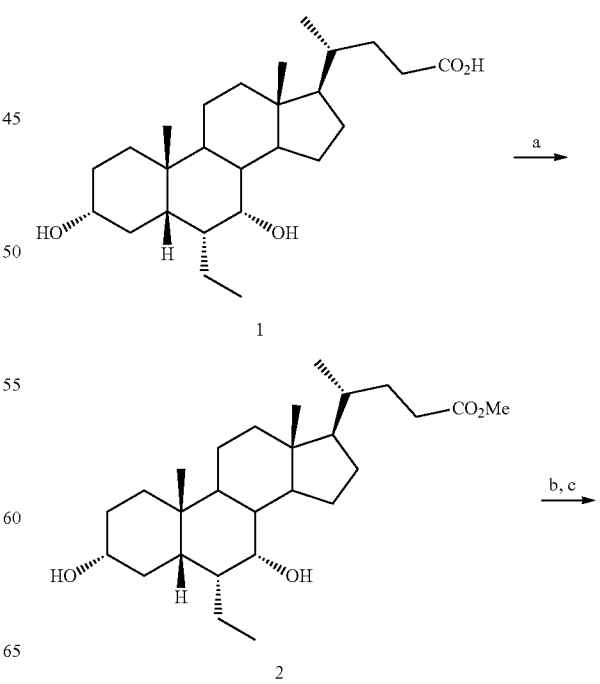

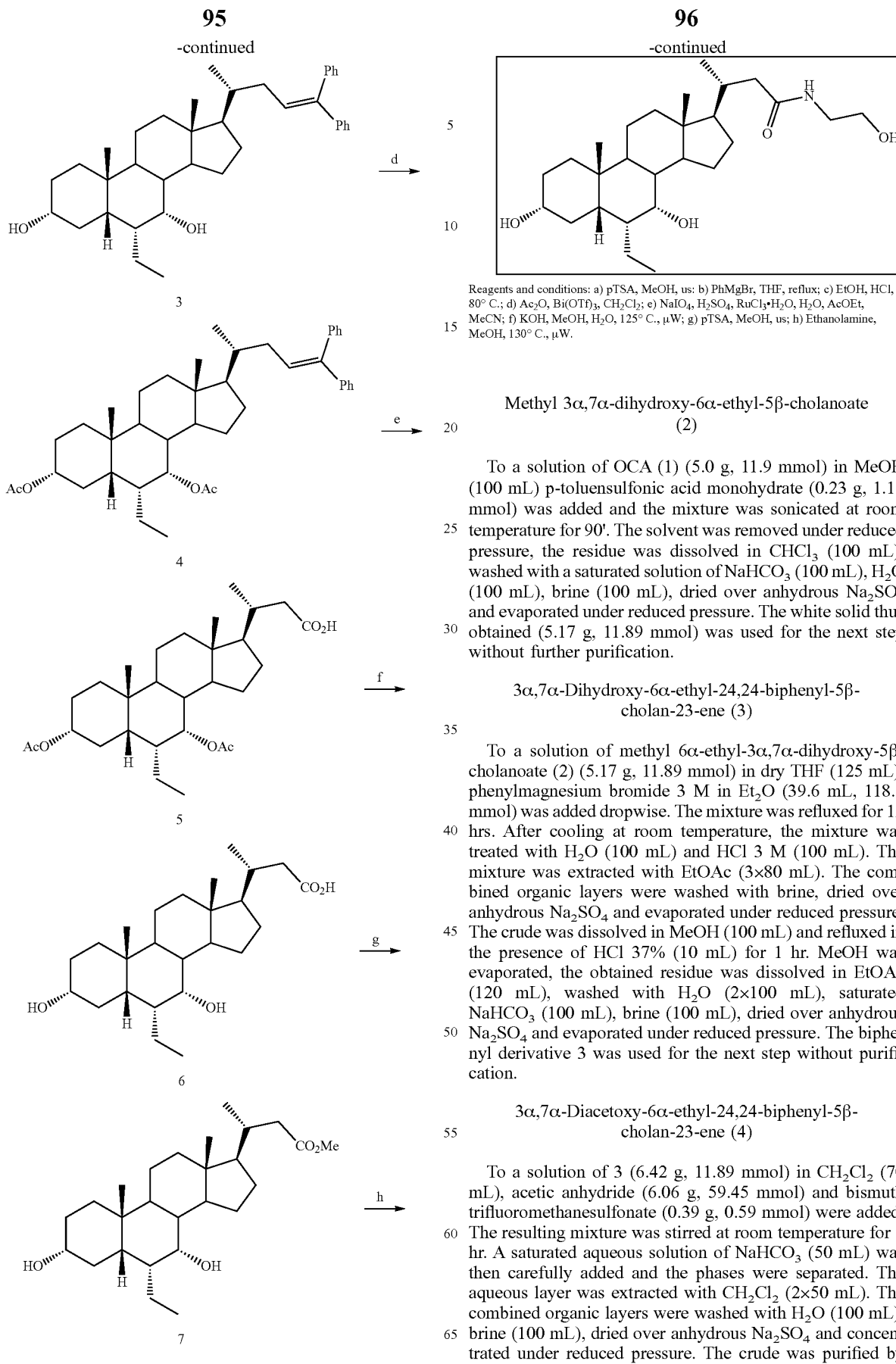

Reagents and conditions: a) pTSA, MeOH, us; b) PhMgBr, THF, reflux; c) EtOH, HCl, 80° C.; d) Ac₂O, Bi(OTf)₃, CH₂Cl₂; e) NaIO₄, H₂SO₄, RuCl₃•H₂O, H₂O, AcOEt, MeCN; f) KOH, MeOH, H₂O, 125° C., µW; g) pTSA, MeOH, us; h) Ethanolamine, MeOH, 130° C., µW.

Methyl 3α,7α-dihydroxy-6α-ethyl-5β-cholanoate
(2)

To a solution of OCA (1) (5.0 g, 11.9 mmol) in MeOH (100 mL) p-toluensulfonic acid monohydrate (0.23 g, 1.19 mmol) was added and the mixture was sonicated at room temperature for 90'. The solvent was removed under reduced pressure, the residue was dissolved in CHCl₃ (100 mL), washed with a saturated solution of NaHCO₃ (100 mL), H₂O (100 mL), brine (100 mL), dried over anhydrous Na₂SO₄ and evaporated under reduced pressure. The white solid thus obtained (5.17 g, 11.89 mmol) was used for the next step without further purification.

3α,7α-Dihydroxy-6α-ethyl-24,24-biphenyl-5β-cholan-23-ene (3)

To a solution of methyl 6α-ethyl-3α,7α-dihydroxy-5β-cholanoate (2) (5.17 g, 11.89 mmol) in dry THF (125 mL), phenylmagnesium bromide 3 M in Et₂O (39.6 mL, 118.9 mmol) was added dropwise. The mixture was refluxed for 12 hrs. After cooling at room temperature, the mixture was treated with H₂O (100 mL) and HCl 3 M (100 mL). The mixture was extracted with EtOAc (3×80 mL). The combined organic layers were washed with brine, dried over anhydrous Na₂SO₄ and evaporated under reduced pressure. The crude was dissolved in MeOH (100 mL) and refluxed in the presence of HCl 37% (10 mL) for 1 hr. MeOH was evaporated, the obtained residue was dissolved in EtOAc (120 mL), washed with H₂O (2×100 mL), saturated NaHCO₃ (100 mL), brine (100 mL), dried over anhydrous Na₂SO₄ and evaporated under reduced pressure. The biphenyl derivative 3 was used for the next step without purification.

3α,7α-Diacetoxy-6α-ethyl-24,24-biphenyl-5β-cholan-23-ene (4)

To a solution of 3 (6.42 g, 11.89 mmol) in CH₂Cl₂ (70 mL), acetic anhydride (6.06 g, 59.45 mmol) and bismuth trifluoromethanesulfonate (0.39 g, 0.59 mmol) were added. The resulting mixture was stirred at room temperature for 1 hr. A saturated aqueous solution of NaHCO₃ (50 mL) was then carefully added and the phases were separated. The aqueous layer was extracted with CH₂Cl₂ (2×50 mL). The combined organic layers were washed with H₂O (100 mL), brine (100 mL), dried over anhydrous Na₂SO₄ and concentrated under reduced pressure. The crude was purified by silica gel flash chromatography using an eluent constituted by petroleum ether/EtOAc (95:5→7:3, v/v) obtaining 5.56 g (8.91 mmol, 75%) of desired intermediate 4.

3α,7α-Diacetoxy-6α-ethyl-24-nor-5β-cholan-23-oic acid (5)

To a suspension of sodium periodate (21.13 g, 98.73 mmol) in $H_2O$ (20 mL), $H_2SO_4$ 2 N in $H_2O$ (3.22 mL) was added and the mixture was stirred at room temperature for 1 hr. The mixture was cooled to 0° C. and treated with ruthenium trichloride hydrate (0.11 g, 0.55 mmol) which was added in one portion. After 1 hr, acetonitrile (31 mL) was added to the solution and after additional 5', a solution of biphenyl derivative 4 (6.85 g, 10.97 mmol) in EtOAc (43 mL) was added. The mixture was stirred at room temperature for 1 hr. The white solid thus formed was filtered off, then the liquor was poured into $H_2O$ (100 mL) and extracted with EtOAc (3×50 mL). The combined organic layers were filtered through a Celite pad, washed with a saturated solution of $Na_2S_2O_3$ in $H_2O$ (100 mL), brine (100 mL), dried over anhydrous $Na_2SO_4$ and concentrated under reduced pressure. The residue was purified by silica gel flash chromatography eluting with EtOAc in petroleum ether from 10 to 50%. The desired acid 5 was obtained as white solid (5.27 g, 10.75 mmol, 98%).

3α,7α-dihydroxy-6α-ethyl-24-nor 5-cholan-23-oic acid (6)

To a solution of 3α,7α-diacetoxy-6α-ethyl-24-nor-5β-cholanoic acid (5) (5.27 g, 10.75 mmol) in MeOH (70 mL), an aqueous solution of KOH (6.02 g, 107.5 mmol in 10 mL of $H_2O$) was added. The reaction was divided in 6 batches of about 15 mL. Each lot was submitted to microwave irradiation (T=120° C., $P_{max}$=270 psi, Power$_{max}$=200 W) for 2 hrs. The diverse lots were collected, the solvent was removed under reduced pressure, the crude was dissolved in $H_2O$ (100 mL) and extracted with $Et_2O$ (2×50 mL). The aqueous phase was acidified with HCl 3 N and extracted with $CH_2Cl_2$ (3×80 mL). The combined organic layers were washed with $H_2O$ (100 mL), brine (100 mL), dried over anhydrous $Na_2SO_4$ and evaporated under reduced pressure. The crude was purified by flash chromatography eluting with MeOH in $CHCl_3$ (from 0 to 10%) in the presence of 0.1% of AcOH to furnish the desired acid 6 as white solid (3.85 g, 9.46 mmol, 88%).

Methyl 3α,7α-dihydroxy-6α-ethyl-24-nor 5β-cholan-23-oate (7)

To a solution of 3α,7α-dihydroxy-6α-ethyl-24-nor 5β-cholan-23-oic acid (6) (0.80 g, 1.72 mmol) in MeOH (20 mL) p-toluensulfonic acid monohydrate (0.04 g, 0.17 mmol) was added and the mixture was sonicated at 25° C. for 4 hrs. The solvent was removed under reduced pressure, the residue was dissolved in $CHCl_3$ (80 mL), washed with a saturated solution of $NaHCO_3$ (80 mL), $H_2O$ (80 mL), brine (80 mL), dried over anhydrous $Na_2SO_4$ and evaporated under reduced pressure. The white solid thus obtained (0.82 g, 1.72 mmol) was used for the following step without further purification.

3α,7α-Dihydroxy-6α-ethyl-N-(2-hydroxyethyl)-24-nor-5β-cholan-23-amide (Compound 19)

A mixture of methyl ester 7 (0.82 g, 1.72 mmol) and ethanolamine (8.08 g, 132.24 mmol) in MeOH (8 mL) was submitted to microwave irradiation (T=130° C., $P_{max}$=200 psi, Power$_{max}$=200 W) for 1 hr. The mixture was concentrated under reduced pressure, the residue was dissolved in $CH_2Cl_2$ (50 mL), washed with HCl 3 N (50 mL), $H_2O$ (50 mL), brine (50 mL), dried over anhydrous $Na_2SO_4$ and evaporated under reduced pressure. The crude was purified by silica gel flash chromatography eluting with $CHCl_3$/MeOH (0→10%+0.1% of AcOH) to furnish the desired derivative Compound 19 as white solid (0.60 g, 1.34 mmol, 78%).

rf: 0.42 (TLC: Silica Gel $F_{254}$S; eluent: $CHCl_3$/MeOH/AcOH 90:10:0.1). $^1$H-NMR (DMSO-d6, 400 MHz) δ 0.53 (3H, s, 18-$CH_3$), 0.71-0.77 (9H, m, 19-$CH_3$+$CH_2CH_3$+21-$CH_3$), 2.05 (1H, m, 22-$CH_2$), 2.98-3.04 (3H, m, 3-CH+$CH_2CH_2OH$), 3.27 (2H, t, J=6.0 Hz, $CH_2CH_2OH$), 3.39 (1H, s, 7-CH), 3.10-3.40 (1H, bs, OH), 3.96 (1H, s, OH), 4.05-4.37 (1H, bs, OH). $^{13}$C-NMR (CD$_3$OD, 400 MHz) δ 12.1 (×2), 19.4, 20.7, 22.5, 23.4 (×2), 28.2, 30.7, 32.9, 33.8, 33.9, 35.5, 35.8, 41.6, 41.7, 42.4, 43.2, 45.6, 50.5, 56.4, 60.3, 68.7, 70.9, 172.3.

Example 20: Synthesis of Compound 20

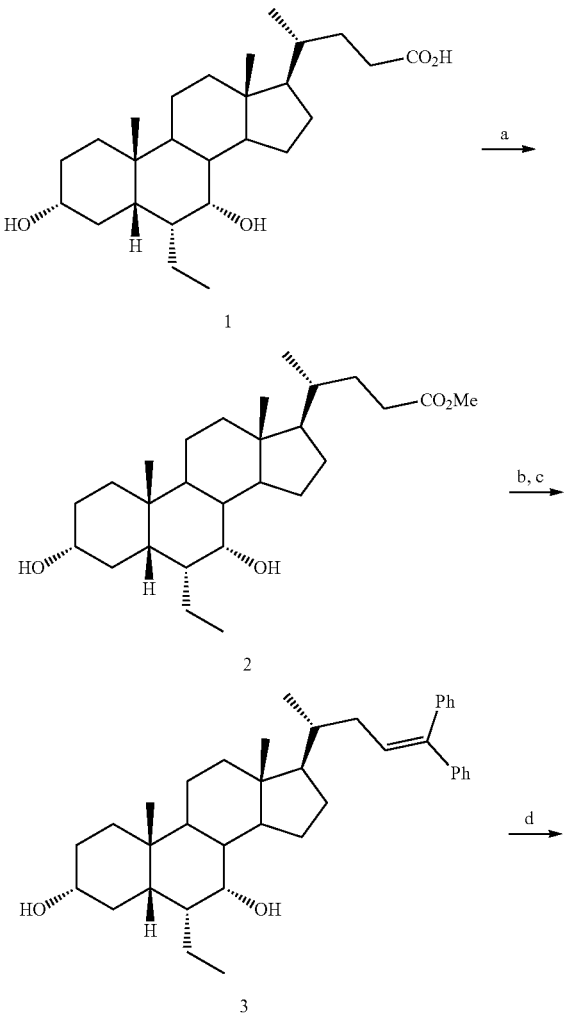

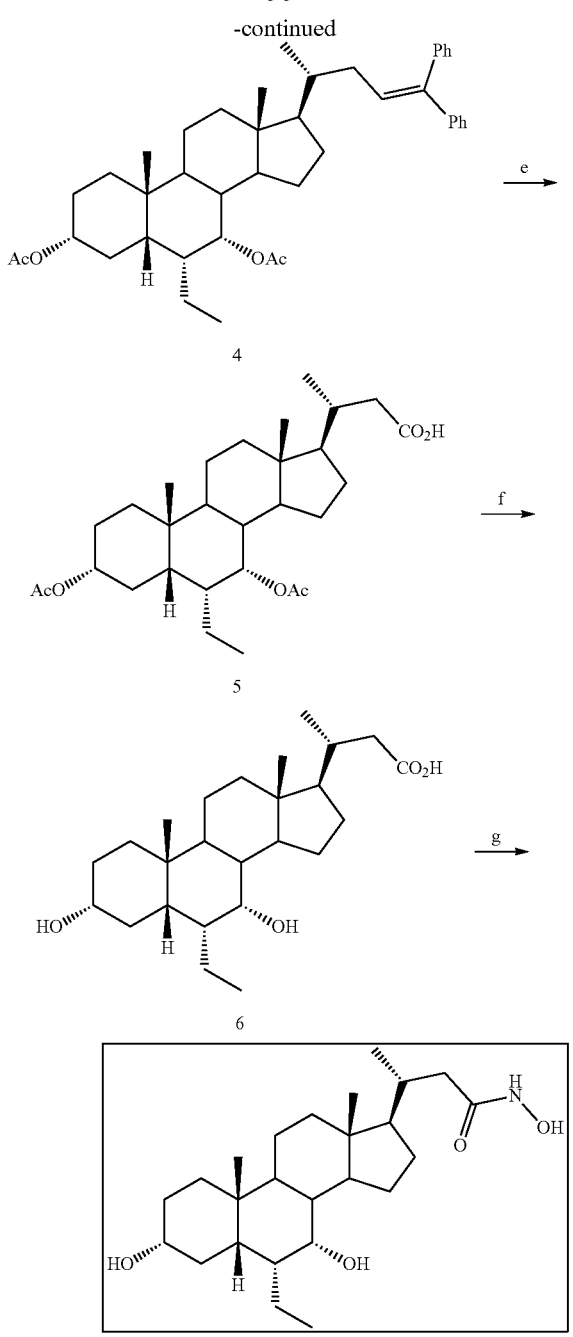

Reagents and conditions: a) pTSA, MeOH, us: b) PhMgBr, THF, reflux; c) EtOH, HCl, 80° C.; d) Ac₂O, Bi(OTf)₃, CH₂Cl₂; e) NaIO₄, H₂SO₄, RuCl₃·H₂O, H₂O, AcOEt, MeCN; f) KOH, MeOH, H₂O, 125° C., μW; g) DMT-MM, Et₃N, NH₂OH, EtOH, reflux.

Methyl 3α,7α-dihydroxy-6α-ethyl-5β-cholanoate (2)

To a solution of OCA (1) (5.0 g, 11.9 mmol) in MeOH (100 mL) p-toluensulfonic acid monohydrate (0.23 g, 1.19 mmol) was added and the mixture was sonicated at room temperature for 90'. The solvent was removed under reduced pressure, the residue was dissolved in CHCl₃ (100 mL), washed with a saturated solution of NaHCO₃ (100 mL), H₂O (100 mL), brine (100 mL), dried over anhydrous Na₂SO₄ and evaporated under reduced pressure. The white solid thus obtained (5.17 g, 11.89 mmol) was used for the next step without further purification.

3α,7α-Dihydroxy-6α-ethyl-24,24-biphenyl-5β-cholan-23-ene (3)

To a solution of methyl 6α-ethyl-3α,7α-dihydroxy-5β-cholanoate (2) (5.17 g, 11.89 mmol) in dry THF (125 mL), phenylmagnesium bromide 3 M in Et₂O (39.6 mL, 118.9 mmol) was added dropwise. The mixture was refluxed for 12 hrs. After cooling at room temperature, the mixture was treated with H₂O (100 mL) and HCl 3 M (100 mL). The mixture was extracted with EtOAc (3×80 mL), the combined organic layers were washed with brine, dried over anhydrous Na₂SO₄ and evaporated under reduced pressure. The crude was dissolved in MeOH (100 mL) and refluxed in the presence of HCl 37% (10 mL) for 1 hr. MeOH was evaporated, the obtained residue was dissolved in EtOAc (120 mL), washed with H₂O (2×100 mL), saturated NaHCO₃ (100 mL), brine (100 mL), dried over anhydrous Na₂SO₄ and evaporated under reduced pressure. The biphenyl derivative 3 was used for the next step without purification.

3α,7α-Diacetoxy-6α-ethyl-24,24-biphenyl-5β-cholan-23-ene (4)

To a solution of 3 (6.42 g, 11.89 mmol) in CH₂Cl₂ (70 mL), acetic anhydride (6.06 g, 59.45 mmol) and bismuth trifluoromethanesulfonate (0.39 g, 0.59 mmol) were added. The resulting mixture was stirred at room temperature for 1 hr. A saturated aqueous solution of NaHCO₃ (50 mL) was then carefully added and the phases were separated. The aqueous layer was extracted with CH₂Cl₂ (2×50 mL). The combined organic layers were washed with H₂O (100 mL), brine (100 mL), dried over anhydrous Na₂SO₄ and concentrated under reduced pressure. The crude was purified by silica gel flash chromatography using an eluent constituted by petroleum ether/EtOAc (95:5→7:3, v/v) obtaining 5.56 g (8.91 mmol, 75%) of desired intermediate 4.

3α,7α-Diacetoxy-6α-ethyl-24-nor-5β-cholan-23-oic acid (5)

To a suspension of sodium periodate (21.13 g, 98.73 mmol) in H₂O (20 mL), H₂SO₄ 2 N in H₂O (3.22 mL) was added and the mixture was stirred at room temperature for 1 hr. The mixture was cooled to 0° C. and treated with ruthenium trichloride hydrate (0.11 g, 0.55 mmol) which was added in one portion. After 1 hr, acetonitrile (31 mL) was added to the solution and after additional 5', a solution of biphenyl derivative 4 (6.85 g, 10.97 mmol) in EtOAc (43 mL) was added. The mixture was stirred at room temperature for 1 hr. The white solid thus formed was filtered off, then the liquor was poured into H₂O (100 mL) and extracted with EtOAc (3×50 mL). The combined organic layers were filtered through a Celite pad, washed with a saturated solution of Na₂S₂O₃ in H₂O (100 mL), brine (100 mL), dried over anhydrous Na₂SO₄ and concentrated under reduced pressure. The residue was purified by silica gel flash chromatography eluting with EtOAc in petroleum ether from 10 to 50%. The desired acid 5 was obtained as white solid (5.27 g, 10.75 mmol, 98%).

3α,7α-dihydroxy-6α-ethyl-24-nor 5β-cholan-23-oic acid (6)

To a solution of 3α,7α-diacetoxy-6α-ethyl-24-nor-5β-cholanoic acid (5) (5.27 g, 10.75 mmol) in MeOH (70 mL), an aqueous solution of KOH (6.02 g, 107.5 mmol in 10 mL of $H_2O$) was added. The reaction was divided in 6 batches of about 15 mL. Each lot was submitted to microwave irradiation (T=120° C., $P_{max}$=270 psi, $Power_{max}$=200 W) for 2 hrs. The diverse lots were collected, the solvent was removed under reduced pressure, the crude was dissolved in $H_2O$ (100 mL) and extracted with $Et_2O$ (2×50 mL). The aqueous phase was acidified with HCl 3 N and extracted with $CH_2Cl_2$ (3×80 mL). The combined organic layers were washed with $H_2O$ (100 mL), brine (100 mL), dried over anhydrous $Na_2SO_4$ and evaporated under reduced pressure. The crude was purified by flash chromatography eluting with MeOH in $CHCl_3$ (from 0 to 10%) in the presence of 0.1% of AcOH to furnish the desired acid 6 as white solid (3.85 g, 9.46 mmol, 88%).

3α,7α-Dihydroxy-6α-ethyl-N-(2-hydroxyethyl)-24-nor 5β-cholan-23-hydroxyamide (Compound 20)

To a solution of 6α-ethyl-3α,7α-dihydroxy-23-nor-5β-cholanoate (6) (0.50 g, 1.23 mmol) in dry DMF (20 mL), DMT-MM (1.36 g, 4.92 mmol) and triethylamine (1.24 g, 12.30 mmol) were added and the mixture was stirred at room temperature for 1 hr. Freshly prepared solution of $NH_2OH$ (0.06 g, 1.84 mmol) in dry DMF was added and the mixture was refluxed for 4 hrs. The reaction was poured into $H_2O$ (40 mL) and extracted with $CHCl_3$ (3×30 mL). The combined organic layers were washed with HCl 1 N (40 mL), with a saturated solution of $NaHCO_3$ (40 mL), $H_2O$ (40 mL), brine (40 mL), dried over anhydrous $Na_2SO_4$ and evaporated under reduced pressure. The crude was purified by silica gel flash chromatography using a solution of $CHCl_3$/MeOH (0→8%+0.1% AcOH). The desired compound Compound 20 was obtained as white solid (0.24 g, 0.57 mmol, 46%).

rf: 0.24 (TLC: Silica Gel 60 RP-8 $F_{254}S$; eluent: $H_2O$/MeCN 50:50). $^1$H-NMR ($CD_3OD$, 400 MHz) δ 0.61 (3H, s, 18-$CH_3$), 0.77-0.88 (9H, m, 19-$CH_3$+$CH_2CH_3$+21-$CH_3$), 2.13-2.16 (1H, m, 22-$CH_2$), 3.18-3.20 (1H, m, 3-CH), 3.53 (1H, s, 7-CH). $^{13}$C-NMR ($CD_3OD$, 400 MHz) δ 10.59, 10.81, 17.9, 20.5, 22.0, 22.3, 23.0, 27.8, 29.9, 32.9, 33.0, 33.6, 35.1, 35.2, 39.5 (×2), 40.0, 41.6, 42.1, 45.2, 50.2, 56.3, 69.5, 71.6, 170.9.

Example 21: Synthesis of Compound 21

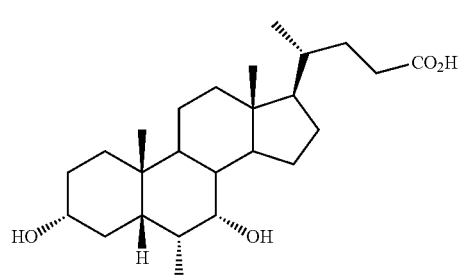

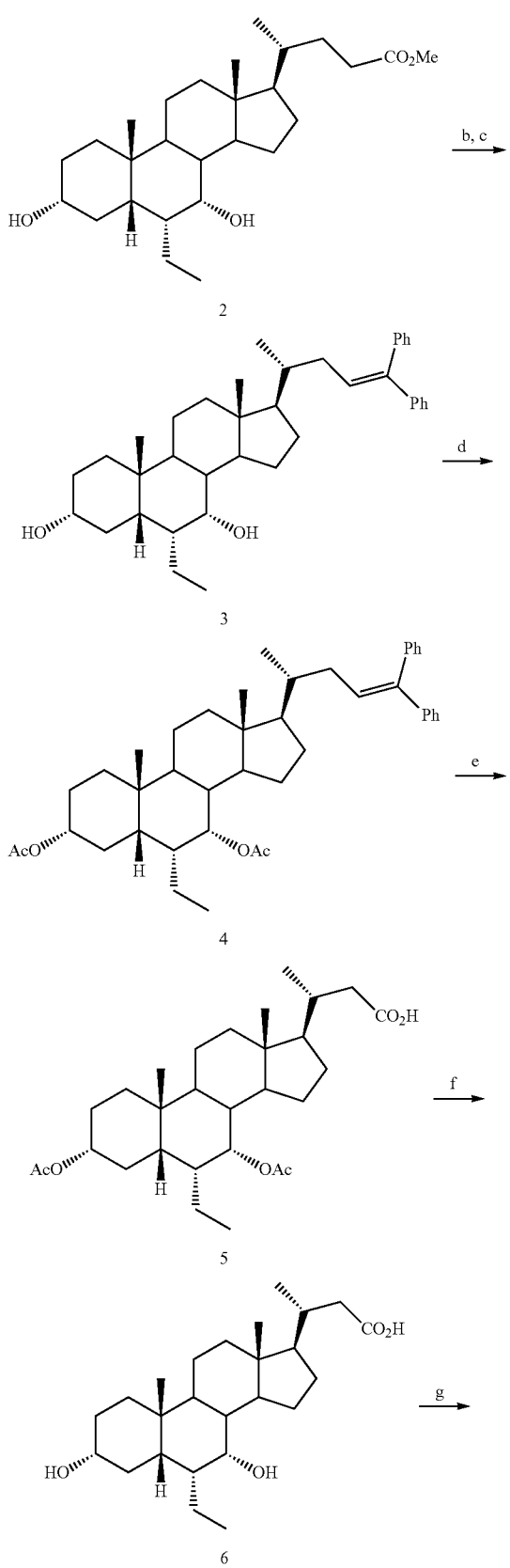

-continued

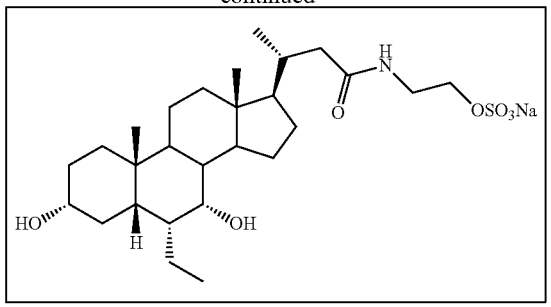

Reagents and conditions: a) pTSA, MeOH, us; b) PhMgBr, THF, reflux; c) EtOH, HCl, 80° C.; d) Ac₂O, Bi(OTF)₃, CH₂Cl₂; e) NaIO₄, H₂SO₄, RuCl₃·H₂O, H₂O, AcOEt, MeCN; f) KOH, MeOH, H₂O, 125° C., μW; g) g) EEDQ, Et₃N, sodium 2-aminoethylsulfate; EtOH, reflux.

Methyl 3α,7α-dihydroxy-6α-ethyl-5β-cholanoate (2)

To a solution of OCA (1) (5.0 g, 11.9 mmol) in MeOH (100 mL) p-toluensulfonic acid monohydrate (0.23 g, 1.19 mmol) was added and the mixture was sonicated at room temperature for 90'. The solvent was removed under reduced pressure, the residue was dissolved in CHCl₃ (100 mL), washed with a saturated solution of NaHCO₃ (100 mL), H₂O (100 mL), brine (100 mL), dried over anhydrous Na₂SO₄ and evaporated under reduced pressure. The white solid thus obtained (5.17 g, 11.89 mmol) was used for the next step without further purification.

3α,7α-Dihydroxy-6α-ethyl-24,24-biphenyl-5β-cholan-23-ene (3)

To a solution of methyl 6α-ethyl-3α,7α-dihydroxy-5β-cholanoate (2) (5.17 g, 11.89 mmol) in dry THF (125 mL), phenylmagnesium bromide 3 M in Et₂O (39.6 mL, 118.9 mmol) was added dropwise. The mixture was refluxed for 12 hrs. After cooling at room temperature, the mixture was treated with H₂O (100 mL) and HCl 3 M (100 mL). The mixture was extracted with EtOAc (3×80 mL), the combined organic layers were washed with brine, dried over anhydrous Na₂SO₄ and evaporated under reduced pressure. The crude was dissolved in MeOH (100 mL) and refluxed in the presence of HCl 37% (10 mL) for 1 hr. MeOH was evaporated, the obtained residue was dissolved in EtOAc (120 mL), washed with H₂O (2×100 mL), a saturated solution of NaHCO₃ (100 mL), brine (100 mL), dried over anhydrous Na₂SO₄ and evaporated under reduced pressure. The biphenyl derivative 3 was used for the next step without purification.

3α,7α-Diacetoxy-6α-ethyl-24,24-biphenyl-5β-cholan-23-ene (4)

To a solution of 3 (6.42 g, 11.89 mmol) in CH₂Cl₂ (70 mL), acetic anhydride (6.06 g, 59.45 mmol) and bismuth trifluoromethanesulfonate (0.39 g, 0.59 mmol) were added. The resulting mixture was stirred at room temperature for 1 hr. A saturated aqueous solution of NaHCO₃ (50 mL) was then carefully added and the phases were separated. The aqueous layer was extracted with CH₂Cl₂ (2×50 mL). The combined organic layers were washed with H₂O (100 mL), brine (100 mL), dried over anhydrous Na₂SO₄ and concentrated under reduced pressure. The crude was purified by silica gel flash chromatography using an eluent constituted by petroleum ether/EtOAc (95:5→7:3, v/v) obtaining 5.56 g (8.91 mmol, 75%) of desired intermediate 4.

3α,7α-Diacetoxy-6α-ethyl-24-nor-5β-cholan-23-oic acid (5)

To a suspension of sodium periodate (21.13 g, 98.73 mmol) in H₂O (20 mL), H₂SO₄ 2 N in H₂O (3.22 mL) was added and the mixture was stirred at room temperature for 1 hr. The mixture was cooled to 0° C. and treated with ruthenium trichloride hydrate (0.11 g, 0.55 mmol) which was added in one portion. After 1 hr, acetonitrile (31 mL) was added to the solution and after additional 5', a solution of biphenyl derivative 4 (6.85 g, 10.97 mmol) in EtOAc (43 mL) was added. The mixture was stirred at room temperature for 1 hr. The white solid thus formed was filtered off, then the liquor was poured into H₂O (100 mL) and extracted with EtOAc (3×50 mL). The combined organic layers were filtered through a Celite pad, washed with a saturated solution of Na₂S₂O₃ in H₂O (100 mL), brine (100 mL), dried over anhydrous Na₂SO₄ and concentrated under reduced pressure. The residue was purified by silica gel flash chromatography eluting with EtOAc in petroleum ether from 10 to 50%. The desired acid 5 was obtained as white solid (5.27 g, 10.75 mmol, 98%).

3α,7α-dihydroxy-6α-ethyl-24-nor 5β-cholan-23-oic acid (6)

To a solution of 3α,7α-diacetoxy-6α-ethyl-24-nor-5β-cholanoic acid (5) (5.27 g, 10.75 mmol) in MeOH (70 mL), an aqueous solution of KOH (6.02 g, 107.5 mmol in 10 mL of H₂O) was added. The reaction was divided in 6 batches of about 15 mL. Each lot was submitted to microwave irradiation (T=120° C., $P_{max}$=270 psi, $Power_{max}$=200 W) for 2 hrs. The diverse lots were collected, the solvent was removed under reduced pressure, the crude was dissolved in H₂O (100 mL) and extracted with Et₂O (2×50 mL). The aqueous phase was acidified with HCl 3 N and extracted with CH₂Cl₂ (3×80 mL). The combined organic layers were washed with H₂O (100 mL), brine (100 mL), dried over anydrous Na₂SO₄ and evaporated under reduced pressure. The crude was purified by flash chromatography eluting with MeOH in CHCl₃ (from 0 to 10%) in the presence of 0.1% of AcOH to furnish the desired acid 6 as white solid (3.85 g, 9.46 mmol, 88%).

Sodium 2-(3α,7α-dihydroxy-6α-ethyl-24-nor 5β-cholan-23-amido)-ethyl sulfate (Compound 21)

To a solution of 6α-ethyl-3α,7α-dihydroxy-23-nor-5β-cholanoate (6) (0.90 g, 2.21 mmol) in ethanol (25 mL), triethylamine (2.24 g, 22.13 mmol) and 2-ethoxy-1-ethoxycarbonyl-1,2-dihydroquinoline (1.37 g, 5.53 mmol) were added and the resulting mixture was stirred at room temperature for 30' at 50° C. for 1 hr. Sodium ethanolamine sulphate (prepared by reaction of ethanolamine and pyridine sulfurtrioxide complex in acetonitrile in 87% yield) (0.72 g, 4.43 mmol) was added to the mixture which was reacted at 90° C. for 6 hrs. The mixture was concentrated under reduced pressure, the residue was dissolved in aqueous NaOH (5% in H₂O, 30 mL) and stirred for 30'. The aqueous phase was extracted with EtOAc (3×50 mL) and concentrated under reduced pressure. The crude was purified by reverse phase flash chromatography eluting with acetonitrile in water (from 5 to 30%) affording 0.78 g (1.41 mmol, 64%) of Compound 21.
rf: 0.44 (TLC: Silica Gel 60 RP-8 $F_{254}S$; eluent: $H_2O$/MeCN 65:35). $^1$H-NMR ($CD_3OD$, 400 MHz) δ 0.65 (3H, s, 18-$CH_3$), 0.80-0.84 (6H, m, 19-$CH_3$+$CH_2CH_3$), 0.89 (3H, d, J=6.1 Hz, 21-$CH_3$), 3.28 (1H, dd, $J_1$=2.4 Hz, $J_{2=12.4}$ Hz, 22-$CH_2$), 3.20-3.25 (1H, m, 3-CH), 3.37 (2H, t, J=5.2 Hz, $CH_2CH_2O$), 3.57 (1H, s, 7-CH), 3.96 (2H, t, J=5.2 Hz, $CH_2CH_2O$). $^{13}$C-NMR ($CD_3OD$, 400 MHz) δ 10.5, 10.8, 18.3, 20.4, 22.0, 22.2, 23.0, 27.8, 29.7, 33.0, 33.9, 35.1, 35.2, 38.6, 39.5, 40.0, 41.6, 42.3, 43.0, 45.4, 50.2, 56.4, 65.5, 69.9, 71.7, 174.7.
Example 22: Synthesis of Compound 22
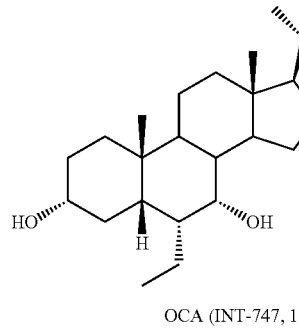
OCA (INT-747, 1)
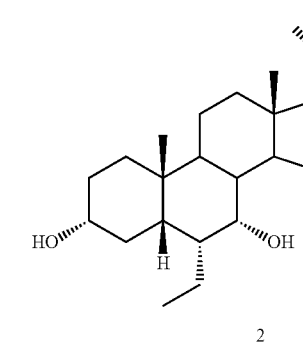
2
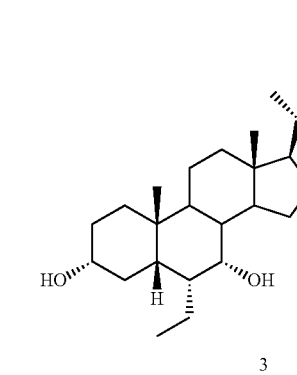
3
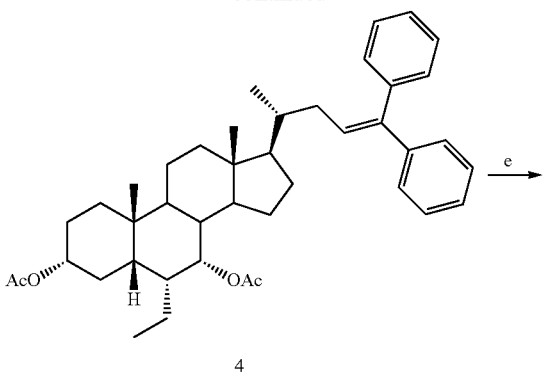
4
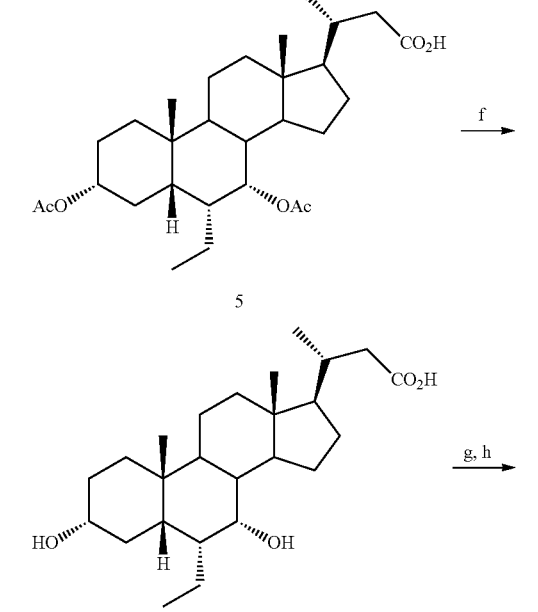
5
6
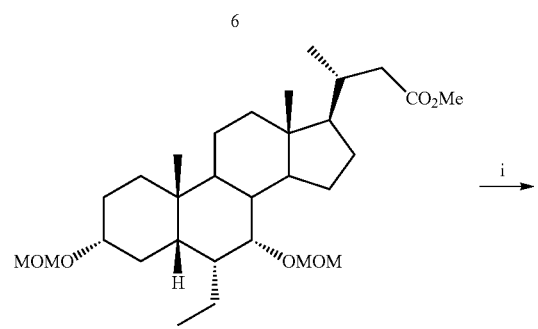
7
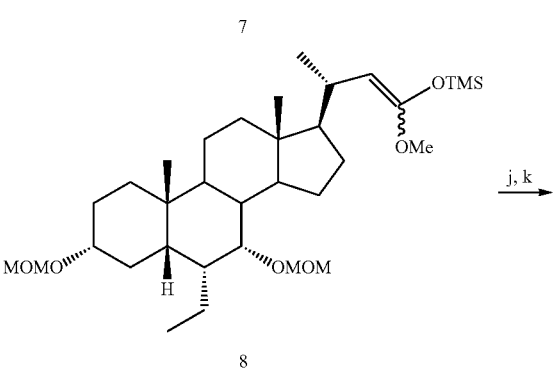
8

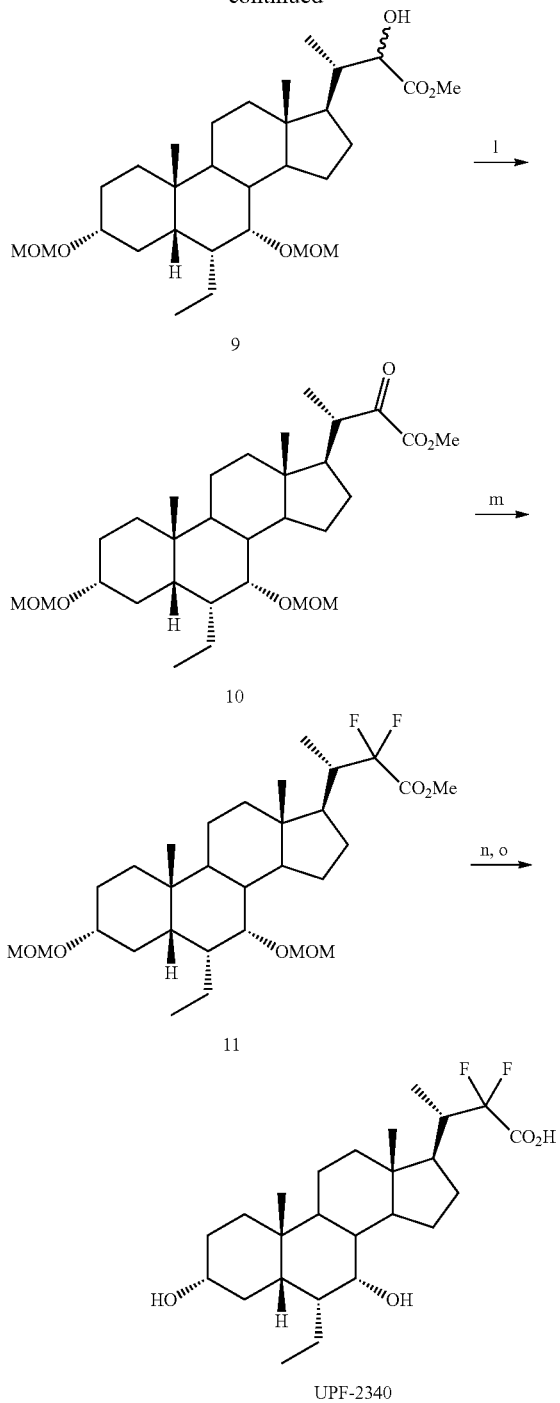

UPF-2340

Reagents and conditions: a) MeOH, pTSA, ultrasounds; b) PhMgBr, THF, reflux;
c) HCl, EtOH, 60° C.; d) Ac$_2$O, Bi(OTf)$_3$, CH$_2$Cl$_2$, r.t.; e) NaIO$_4$, RuCl$_3$•H$_2$O, H$_2$SO$_4$,
MeCN, H$_2$O, EtOAc, r.t. to 0° C.; f) KOH, MeOH, H$_2$O μwaves, 120° C.;
g) MeOH, pTSA, ultrasounds; h) MOMCl, DIPEA, DMAP, CH$_2$Cl$_2$,
reflux; i) LDA TMSCl, THF, -78° C.; j) Pb(OAc)$_4$, CH$_2$Cl$_2$, r.t.; k) K$_2$CO$_3$, MeOH, r.t.;
l) (COCl)$_2$ DMSO, Et$_3$N, CH$_2$Cl$_2$, -60° C.; m) Deoxo-fluor®, THF, reflux;
n) HCl 37%, MeOH, 45° C.; o) NaOH, MeOH, 45° C.

Methyl 3α,7α-dihydroxy-6α-ethyl-5β-cholanoate (2)

To a solution of OCA (1) (5.0 g, 11.9 mmol) in MeOH (100 mL) p-toluensulfonic acid monohydrate (0.23 g, 1.19 mmol) was added and the mixture was sonicated at room temperature for 90'. The solvent was removed under reduced pressure, the residue was dissolved in CHCl$_3$ (100 mL), washed with a saturated solution of NaHCO$_3$ (100 mL), H$_2$O (100 mL), brine (100 mL), dried over anhydrous Na$_2$SO$_4$ and evaporated under reduced pressure. The white solid thus obtained (5.17 g, 11.89 mmol) was used for the next step without further purification.

3α,7α-Dihydroxy-6α-ethyl-24,24-biphenyl-5β-cholan-23-ene (3)

To a solution of methyl 6α-ethyl-3α,7α-dihydroxy-5β-cholanoate (2) (5.17 g, 11.89 mmol) in dry THF (125 mL), phenylmagnesium bromide 3 M in Et$_2$O (39.6 mL, 118.9 mmol) was added dropwise. The mixture was refluxed for 12 hrs. After cooling at room temperature, the mixture was treated with H$_2$O (100 mL) and HCl 3 M (100 mL). The mixture was extracted with EtOAc (3×80 mL). The combined organic layers were washed with brine, dried over anhydrous Na$_2$SO$_4$ and evaporated under reduced pressure. The crude was dissolved in MeOH (100 mL) and refluxed in the presence of HCl 37% (10 mL) for 1 hr. MeOH was evaporated, the residue obtained was dissolved in EtOAc (120 mL), washed with H$_2$O (2×100 mL), saturated NaHCO$_3$ (100 mL), brine (100 mL), dried over anhydrous Na$_2$SO$_4$ and evaporated under reduced pressure. The biphenyl derivative 3 was used for the next step without purification.

3α,7α-Diacetoxy-6α-ethyl-24,24-biphenyl-5β-cholan-23-ene (4)

To a solution of 3 (6.42 g, 11.89 mmol) in CH$_2$Cl$_2$ (70 mL), acetic anhydride (6.06 g, 59.45 mmol) and bismuth trifluoromethanesulfonate (0.39 g, 0.59 mmol) were added. The resulting mixture was stirred at room temperature for 1 hr. A saturated aqueous solution of NaHCO$_3$ (50 mL) was then carefully added and the phases were separated. The aqueous layer was extracted with CH$_2$Cl$_2$ (2×50 mL). The combined organic layers were washed with H$_2$O (100 mL), brine (100 mL), dried over anhydrous Na$_2$SO$_4$ and concentrated under reduced pressure. The crude was purified by silica gel flash chromatography using an eluent constituted by petroleoum ether/EtOAc (95:5→7:3, v/v) obtaining 5.56 g (8.91 mmol, 75%) of desired intermediate 4.

3α,7α-Diacetoxy-6α-ethyl-24-nor-5β-cholan-23-oic acid (5)

To a suspension of sodium periodate (21.13 g, 98.73 mmol) in H$_2$O (20 mL), H$_2$SO$_4$ 2N in H$_2$O (3.22 mL) was added and the mixture was stirred at room temperature for 1 hr. The mixture was cooled to 0° C. and treated with ruthenium trichloride hydrate (0.11 g, 0.55 mmol) which was added in one portion. After 1 hr, acetonitrile (31 mL) was added to the solution and after additional 5', a solution of biphenyl derivative 4 (6.85 g, 10.97 mmol) in EtOAc (43 mL) was added. The mixture was stirred at room temperature for 1 hr. The white solid thus formed was filtered off, then the liquor was poured into H$_2$O (100 mL) and extracted with EtOAc (3×50 mL). The combined organic layers were filtered through a Celite pad, washed with a saturated solution of Na$_2$S$_2$O$_3$ in H$_2$O (100 mL), brine (100 mL), dried over anhydrous Na$_2$SO$_4$ and concentrated under reduced pressure. The residue was purified by silica gel flash chromatography eluting with EtOAc in petroleum ether from 10 to 50%. The desired acid 5 was obtained as white solid (5.27 g, 10.75 mmol, 98%).

3α,7α-Dihydroxy-6α-ethyl-24-nor 5β-cholan-23-oic acid (6)

To a solution of 3α,7α-diacetoxy-6α-ethyl-24-nor-5β-cholanoic acid (5) (5.27 g, 10.75 mmol) in MeOH (70 mL), an aqueous solution of KOH (6.02 g, 107.5 mmol in 10 mL of $H_2O$) was added. The reaction was divided in 6 batches of about 15 mL Each lot was submitted to microwave irradiation (TS=120° C., $PO_{max}$=270 psi, $Power_{max}$=200 W) for 2 hrs. The diverse lots were collected, the solvent was removed under reduced pressure, and the crude was dissolved in $H_2O$ (100 mL) and extracted with $Et_2O$ (2×50 mL). The aqueous phase was acidified with HCl 3 N and extracted with $CH_2Cl_2$ (3×80 mL). The combined organic layers were washed with $H_2O$ (100 mL), brine (100 mL), dried over anhydrous $Na_2SO_4$ and evaporated under reduced pressure. The crude was purified by flash chromatography eluting with MeOH in $CHCl_3$ (from 0 to 10%) in the presence of 0.1% of AcOH to furnish the desired acid 6 as white solid (3.85 g, 9.46 mmol, 88%).

Methyl 3α,7α-dimethoxymethyloxy-6α-ethyl-24-nor-5β-cholan-23-oate (7)

To a solution of 3α,7α-dihydroxy-6α-ethyl-24-nor-5β-cholanoic acid (6) (3.0 g, 7.39 mmol) in MeOH (50 mL), p-toluensulfonic acid monohydrate (0.14 g, 0.74 mmol) was added, and the resulting mixture was sonicated at room temperature for 4 hours. The solvent was removed under reduced pressure, the residue was dissolved in $CHCl_3$ (80 mL) and washed with a saturated solution of $NaHCO_3$ (50 mL), $H_2O$ (50 mL) and brine (50 mL). The organic layer was dried over $Na_2SO_4$ and concentrated under reduced pressure. The ester thus obtained was dissolved in $CH_2Cl_2$ (30 mL) and diisopropylethylamine (10.17 mL, 59.11 mmol), 4-(N,N-dimethylamino)-pyridine (0.09 g, 0.74 mmol) and methoxymethylchloride (3.35 mL, 44.33 mmol) were sequentially added to the resulting solution. The mixture was stirred and refluxed for 24 hours. The reaction then allowed to cool to room temperature and washed with a saturated solution of $NH_4Cl$ (30 mL), $H_2O$ (30 mL) and brine (30 mL). The organic layer was dried over $Na_2SO_4$ and concentrated under reduced pressure, to afford 3.57 g of 7 as pale yellow oil that was used for the following step without further purification (3.57 g, 7.02 mmol, 95%).

Methyl 3α,7α-dimethoxymethyloxy-6α-ethyl-22(R+S)-hydroxy-24-nor-5β-cholan-23-oate (9)

To a stirred solution of diisopropylamine (7.92 mL, 55.91 mmol) in distilled THF (30 mL) under $N_2$ atmosphere and cooled at −40° C., nBuLi (2.5 M in hexane, 21.52 mL, 53.81 mmol) was added dropwise. After 15 minutes, the solution was cooled at −78° C. and chlorotrimethylsilane (7.28 mL, 57.30 mmol) was added dropwise. After additional 15 minutes, a solution of protected ester 7 (3.55 g, 6.99 mmol) in distilled THF (10 mL) was added dropwise in about 20 minutes, maintaining the internal temperature not over −70° C. Once the addition was finished, the reaction mixture was stirred at −78° C. for 1 additional hour and then was warmed at room temperature. Volatiles were removed under reduced pressure, and the residue was suspended in petroleum ether (80 mL) and filtered under vacuum. The liquor was concentrated under reduced pressure to furnish the desiderate compound 9. The intermediate thus obtained was directly dissolved in distilled $CH_2Cl_2$ (20 mL) and added dropwise to a 0° C. cooled suspension of freshly crystallized and acetic acid free lead(IV)tetraacetate (6.64 g, 10.484 mmol) in distilled $CH_2Cl_2$ (30 mL) under $N_2$ atmosphere. The mixture was stirred at 0° C. for 30 minutes then was filtered under vacuum through a Celite pad. The filtrate was concentrated under reduced pressure, and the residue was quickly filtered through a silica gel pad (h: 8 cm, φ: 4 cm), collecting the crude with petroleum ether/AcOEt (8:2, v/v). After evaporation of the solvents, the residue was dissolved in MeOH (30 mL) and to the resulting solution solid potassium carbonate (1.93 g, 13.98 mmol) was added. The resulting suspension was vigorously stirred at room temperature for 15 minutes. The mixture was then diluted with $CH_2Cl_2$ (40 mL) and filtered under vacuum. The filtrate was further diluted with additional $CH_2Cl_2$ (50 mL) and washed with brine (50 mL). The phases were separated, the aqueous phase was extracted with $CH_2Cl_2$ (3×40 mL), and all the collected organic layers were combined, dried over $Na_2SO_4$ and concentrated under reduced pressure. The residue was purified by flash chromatography by using petroleum ether/AcOEt from 80:20 (v/v) to 50:50 (v/v) to afford 9 as mixture of two C22-epimers (1.17 g, 2.24 mmol, 32%).

Methyl 3α,7α-dimethoxymethyloxy-6α-ethyl-22-oxo-24-nor-5β-cholan-23-oate (10)

To a solution of oxalyl chloride (0.47 mL, 5.50 mmol) in distilled $CH_2Cl_2$ (15 mL) under $N_2$ atmosphere and cooled ad −60° C., dimethylsulfoxide (0.78 mL, 10.99 mmol) diluted in $CH_2Cl_2$ (3 mL) was added dropwise. After 15 minutes, a solution of 22-hydroxy derivative 9 (1.15 g, 2.20 mmol) in $CH_2Cl_2$ (15 mL) was added dropwise, and the resulting mixture was stirred at −60° C. for 1 hours. Then triethylamine (3.08 mL, 21.99 mmol) was added dropwise, and the mixture was slowly warmed at room temperature. The reaction mixture was treated with KOH 1M (20 mL) for 5 minutes, the two phases were separated and the aqueous one was extracted with $CH_2Cl_2$ (2×20 mL). The collected organic layers were washed with brine (50 mL), dried over $Na_2SO_4$ and concentrated under reduced pressure. The residue was purified by flash chromatography, collecting the desired 22-oxo derivative 10 (0.88 g, 1.69 mmol, 77%) by using petroleum ether/AcOEt from 90:10 (v/v) to 80:20 (v/v).

Methyl 3α,7α-dimethoxymethyloxy-6α-ethyl-22,22-difluoro-24-nor-5β-cholan-23-oate (11)

To a solution of 22-keto derivative 10 (0.50 g, 0.96 mmol) in distilled THF (9 mL) under $N_2$ atmosphere, bis(2-methoxyethyl)aminosulfur trifluoride (Deoxo-Fluor® 50% in THF 3.29 mL, 7.67 mmol) was added and the reaction was stirred at 50° C. for 16 hours. Supplementary Deoxo-Fluor® (2.27 mL, 5.27 mmol) was added and the mixture was refluxed for further 72 hours. The reaction was then allowed to cool to room temperature and the mixture was cautiously poured in a saturated solution of $NaHCO_3$ (40 mL) placed in a water-ice bath and under magnetic stirring. Once the $CO_2$ release was finished, the mixture was extracted with AcOEt (2×40 mL), the combined organic layers were washed with $H_2O$ (60 mL), brine (60 mL), dried over $Na_2SO_4$ and concentrated under reduced pressure. The residue was filtered through a silica pad eluting with petroleum ether/AcOEt 80:20 (v/v) and the crude compound 11 was used for the following step without further purification.

3α,7α-Dihydroxy-6α-ethyl-22,22-difluoro-24-nor-5β-cholan-23-oic acid (Compound 22)

To a solution of derivative 11 (0.96 mmol) in MeOH (12 mL), HCl 37% (0.80 mL, 9.60 mmol) was added, and the mixture was stirred at 45° C. for 12 hours. Then sodium hydroxide (0.57 g, 14.39 mmol) was added, and the mixture was stirred at 45° C. for additional 4 hours. The solvent was removed under reduced pressure, the residue was dissolved in H$_2$O (25 mL) and washed with Et$_2$O (2×20 mL). The aqueous phase was acidified up to pH=5 by adding HCl 3N and extracted with AcOEt (3×30 mL). The solvent was removed under reduced pressure and the residue was purified by RP-18 medium pressure liquid chromatography, by using H$_2$O/MeCN from 95:5 (v/v) to 40:60 (v/v) obtaining 0.06 g of Compound 22 as white solid (0.06 g, 0.13 mmol, 14%)

Rf=0.55 (RP-C8 SiO$_2$, F-254s, H$_2$O/MeCN 60:40). M.p.=254-256° C. $^1$H-NMR (DMSO-d$_6$, 400 MHz) δ: 0.60 (3H, s, 18-CH$_3$), 0.78-0.80 (6H, m, 19-CH$_3$+CH$_2$CH$_3$), 0.92 (3H, d, J=6.6 Hz, 21-CH$_3$), 2.09-2.14 (1H, m, 20-CH), 3.08-3.12 (1H, m, 3-CH), 3.47 (1H, s, 7-CH). $^{13}$C-NMR (DMSO-d$_6$, 100.6 MHz) δ 11.8, 12.1, 20.9, 22.6, 23.5, 23.9, 27.8, 30.8, 31.1, 33.0, 33.9, 35.6, 35.9, 41.6, 43.2, 45.7, 49.8, 50.8, 68.8, 71.0, 121.0 (J$_{C-F}$=277.6 Hz), 167.2 (J$_{C-F}$=28.2 Hz).

Example 23: Synthesis of Compound 23

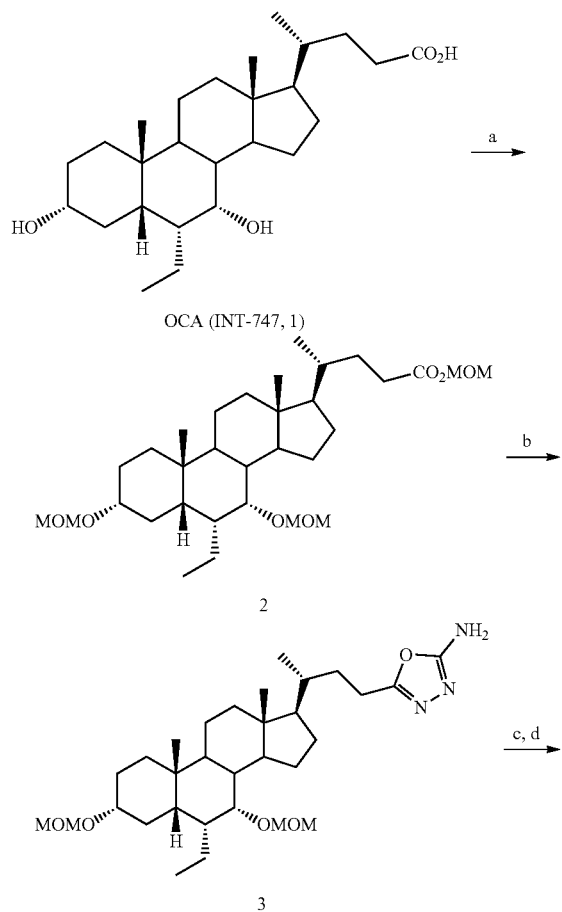

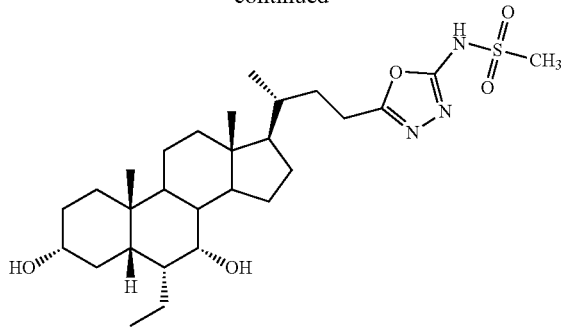

UPF-2332

Reagents and conditions: a) MOMCl, DIPEA, DMAP, reflux.; b) NH$_2$NH$_2$, BrCN, EtOH, reflux then r.t.; c) CH$_3$SO$_2$Cl, Et$_3$N, CH$_2$Cl$_2$, reflux; d) HCl 3N, MeOH, 45° C.

Methoxymethyl 3α,7α-dimethoxymethyloxy-6α-ethyl-5β-cholan-24-oate (2)

To a solution of OCA (1) (1.0 g, 2.38 mmol) in CH$_2$Cl$_2$ (40 mL), diisopropylethylamine (4.94 mL, 28.54 mmol), methoxymethylchloride (1.45 mL, 19.03 mmol), and 4-(N,N-dimethylamino)-pyridine (0.06 g, 0.47 mmol) were sequentially added. The resulting mixture was stirred and refluxed for 18 hours. The reaction was then washed with a saturated solution of NH$_4$Cl (40 mL), H$_2$O (40 mL) and brine (40 mL). The organic layer was dried over Na$_2$SO$_4$ and concentrated under reduced pressure to afford 1.18 g of 2 as pale yellow oil that was used for the following step without further purification (1.18 g, 2.14 mmol).

2-(3α,7α-Dimethoxymethyloxy-6α-ethyl-5β-cholan-24-nor-23-cholanyl)-5-amino-1,3,4-oxadiazole (3)

To a solution of ester 2 (0.50 g, 0.90 mmol) in EtOH (6 mL), hydrazine monohydrate (65% in water, 0.13 mL, 1.81 mmol) was added and the mixture was refluxed for 3 hours. The reaction was cooled at room temperature and cyanogen bromide (0.29 g, 2.71 mmol) was added portionwise. The suspension thus obtained was stirred at room temperature for additional 5 hours then was quenched by addition of a saturated solution of NaHCO$_3$ (40 mL). The mixture was extracted with AcOEt (3×50 mL), the combined organic layers were washed with H$_2$O (100 mL), brine (100 mL), dried over Na$_2$SO$_4$ and evaporated under reduced pressure. The crude was purified by flash chromatography to afford the desired oxadiazolamine derivative 3 as colorless oil (0.19 g, 0.34 mmol, 38%).

2-(3α,7α-Dihydroxy-6α-ethyl-5(1-cholan-24-nor-23-cholanyl)-5-methylsulfonamido-1,3,4-oxadiazole (Compound 23)

To a solution of oxadiazolamine derivative 3 (0.10 g, 0.18 mmol) in CH$_2$Cl$_2$ (10 mL), triethylamine (0.16 mL, 1.10 mmol) and methanesulfonyl chloride (0.04 mL, 0.55 mmol) were added and the resulting mixture was refluxed for 4 hours. The reaction was then quenched with a saturated solution of NH$_4$Cl (20 mL) and extracted with CH$_2$Cl$_2$ (3×10 mL). The combined organic layers were washed with a saturated solution of NaHCO$_3$ (30 mL), H$_2$O (30 mL), brine (30 mL), dried over Na$_2$SO$_4$ and concentrated under reduced pressure. The residue was then dissolved into MeOH (3 mL) and treated with HCl 3 N (1 mL). The solvent was removed under reduced pressure, the residue was dissolved in H$_2$O (15 mL) and extracted with Et$_2$O (3×15 mL). The combined organic layers were washed with H$_2$O (30 mL), brine (30 mL), dried over Na$_2$SO$_4$ and evaporated under reduced pressure. The crude was purified by flash chromatography eluting to give Compound 23 as white solid (26 mg, 0.05 mmol, 27%).

Rf=0.31 (SiO$_2$, F-254, CH$_2$Cl$_2$/MeOH 95:5). $^1$H-NMR (DMSO-d$_6$, 400 MHz) δ: 0.57 (3H, s, 18-CH$_3$), 0.79-0.85 (6H, m, 19-CH$_3$+CH$_2$CH$_3$), 0.90 (3H, d, J=5.9 Hz, 21-CH$_3$), 2.49-2.68 (2H, m, 23-CH$_2$), 2.93 (3H, s, SCH$_3$), 3.09-3.13 (1H, m, 3-CH), 3.47 (1H, s, 7-CH). $^{13}$C-NMR (DMSO-d$_6$, 100.6 MHz) δ 12.5 (2×), 18.8, 21.2, 22.5, 22.9, 23.9 (2×), 28.6, 31.1, 31.9, 33.5, 34.2, 35.5, 35.9, 36.3, 39.3, 42.1 (2×), 42.9, 46.1, 50.9, 56.69.30, 71.5, 157.6, 160.6.

Example 24: Synthesis of Compound 24

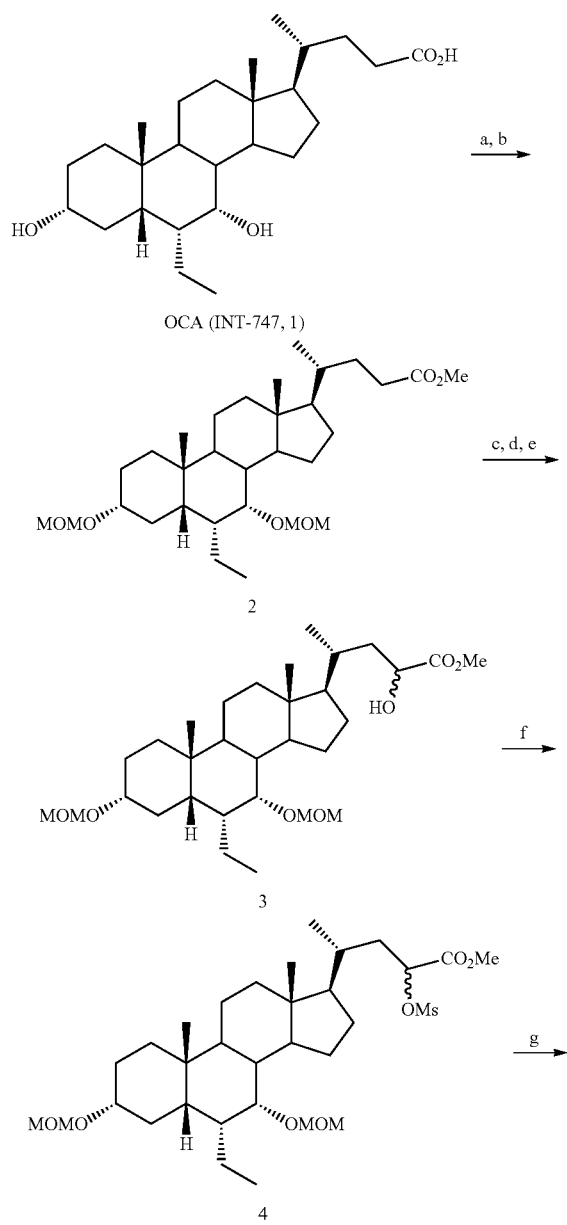

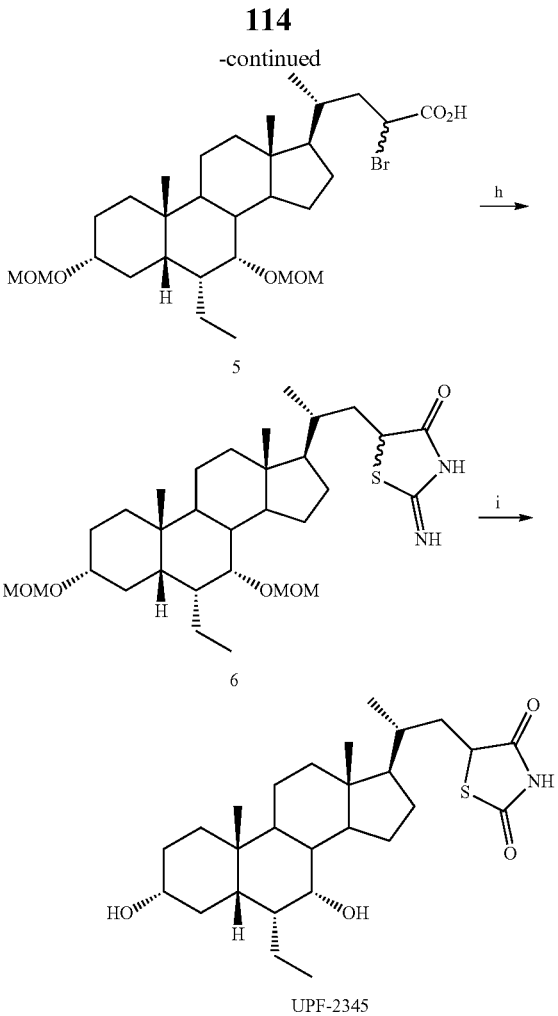

Reagents and conditions: a) MeOH, pTSA, ultrasounds; b) MOMCl, DIPEA, DMAP, CH$_2$Cl$_2$, reflux; c) iPr$_2$NH, nBuLi 2.5 N in hexane, TMSCl, THF, -78° C.; d) Pb(OAc)$_4$, CH$_2$Cl$_2$, r.t.; e) K$_2$CO$_3$, MeOH, r.t.; f) MsCl, pyr, r.t.; g) LiBr, DMF, 40° C.; h) (NH$_2$)$_2$CS, NaOAc, EtOH, reflux; i) Aq. HCl 37%, EtOH, reflux.

Methyl 3α,7α-di methoxymethyloxy-6α-ethyl-5β-cholan-24-oate (2)

To a solution of OCA (1) (250 mg, 0.59 mmol) in MeOH (10 mL), p-toluensulfonic acid monohydrate (10 mg, 0.06 mmol) was added, and the resulting mixture was sonicated for 2 hours. The solvent was removed under reduced pressure, the residue was dissolved in AcOEt (15 mL) and sequentially washed with a saturated solution of NaHCO$_3$ (15 mL), H$_2$O (10 mL) and brine (10 mL). The organic layer was dried over Na$_2$SO$_4$ and concentrated under reduced pressure. The residue was then dissolved in CH$_2$Cl$_2$ (15 mL), and to the resulting solution diisopropylethylamine (0.32 mL, 4.23 mmol), 4-(N,N-dimethylamino)-pyridine (7 mg, 0.06 mmol) and methoxymethylchloride (0.27 mL, 3.55 mmol) were sequentially added. The mixture was then refluxed until completeness. The reaction was cooled at room temperature and washed with HCl 3 N (10 mL), H$_2$O (10 mL), a saturated solution of NaHCO$_3$ (20 mL) and brine (15 mL). The organic layer was dried over Na$_2$SO$_4$ and concentrated under reduced pressure, to afford 302 mg of 2 as pale yellow oil that was used for the following step without further purification (0.3 g, 0.58 mmol).

Methyl 3α,7α-dimethoxymethyloxy-6α-ethyl-23(R+S)-hydroxy-5β-cholan-24-oate (3)

To a stirred solution of diisopropylamine (0.65 mL, 4.60 mmol) in distilled THF (5 mL) under $N_2$ atmosphere and cooled at −40° C., nBuLi (2.5 M in hexane, 1.77 mL, 4.43 mmol) was added dropwise. After 15 minutes, the solution was cooled to −78° C. and chlorotrimethylsilane (0.59 mL, 4.72 mmol) was added dropwise. A solution of 2 (0.30 g, 0.58 mmol) in THF (5 mL) was added portionwise at −70° C. Once the addition was finished, the reaction mixture was stirred at −78° C. for 1 hour and then allowed to react at room temperature. Volatiles were removed under reduced pressure. The residue was directly dissolved in distilled $CH_2Cl_2$ (5 mL). The resulting solution was added dropwise to a suspension of freshly crystallized and acetic acid free lead(IV)tetraacetate (0.38 g, 0.56 mmol) in distilled $CH_2Cl_2$ (7 mL) under $N_2$ atmosphere. After 30 minutes the reaction mixture was filtered under vacuum through a Celite pad. The filtrate was concentrated under reduced pressure and the residue was filtered through a silica gel pad. The residue was dissolved in MeOH (6 mL) and treated with potassium carbonate (0.16 g, 1.15 mmol). The resulting suspension was vigorously stirred at room temperature for 15 minutes. The mixture was then diluted with $CH_2Cl_2$ (15 mL) and filtered under vacuum. The filtrate was further diluted with additional $CH_2Cl_2$ (15 mL) and washed with brine (20 mL). The aqueous phase was extracted with $CH_2Cl_2$ (3×10 mL), and all the collected organic layers were dried over $Na_2SO_4$ and concentrated under reduced pressure. The residue was purified by flash chromatography to afford 0.13 g of 3 as mixture of two C23-epimers (0.13 g, 0.24 mmol, 41%).

Methyl 3α,7α-dimethoxymethyloxy-6α-ethyl-23(R+S)-(methanesulfonyloxy)-5β-cholan-24-oate (4)

To a stirred solution of 3 (0.13 g, 0.24 mmol) in pyridine (5 mL), methanesulfonyl chloride (0.09 mL, 1.18 mmol) was added, and the resulting mixture was stirred at room temperature for 12 hours. The mixture was then poured into $H_2O$ (10 mL) and extracted with $CH_2Cl_2$ (3×10 mL). The collected organic layers were washed with HCl 0.5 M (3×5 mL), with a saturated solution of $NaHCO_3$ (10 mL), brine (10 mL), dried over $Na_2SO_4$ and concentrated under reduced pressure, to give 4 (as mixture of two C23-epimers) which was used such as for the next step.

Methyl 3α,7α-dimethoxymethyloxy-6α-ethyl-23(R+S)-bromo-5β-cholan-24-oate (5)

To a solution of 4 (0.24 mmol) in DMF (5 mL), lithium bromide (0.06 g, 0.71 mmol) was added, and the resulting mixture was stirred at 40° C. for 6 hours. AcOEt (10 mL) was then added, and the mixture was washed with $H_2O$ (3×10 mL), brine (10 mL), dried over $Na_2SO_4$ and concentrated under reduced pressure. The residue was purified to afford 90 mg of desired bromo derivative 5 as mixture of two C23-epimers (0.09 g, 0.15 mmol, 63% from 3).

3α,7α-Dimethoxymethyloxy-6α-ethyl-23,24-bisnor-22-(2-imino-4-oxo-thiazolidin-5-yl)-5β-cholane (6)

To a solution of bromo derivative 5 (90 mg, 0.15 mmol) in EtOH (10 mL), thiourea (91 mg, 1.19 mmol) and sodium acetate (98 mg, 1.19 mmol) were added, and the resulting mixture was stirred and refluxed for 24 hours. The reaction was cooled at room temperature and volatiles were removed under reduced pressure. The residue was dissolved in AcOEt (10 mL), washed with $H_2O$ (2×10 mL), brine (10 mL), dried over $Na_2SO_4$ and concentrated under reduced pressure to afford 6 as mixture of epimers. The crude was used for the next step without further purification.

3α,7α-Dihydroxy-6α-ethyl-23,24-bisnor-22-(2,4-dioxo-thiazolidin-5-yl)-5β-cholane (Compound 24)

To a solution of iminothiazolidine derivative 6 (0.15 mmol) in EtOH (4 mL), HCl 37% (0.7 mL) was added and the resulting mixture was stirred and refluxed. The mixture was then treated with $H_2O$ (8 mL) and organic volatiles were removed under reduced pressure. $H_2O$ (3 mL) was added and the mixture was extracted with $CH_2Cl_2$ (3×7 mL), dried over $Na_2SO_4$ and concentrated under reduced pressure. After chromatographic purification, 5 mg of desired Compound 24 were obtained (5 mg, 0.01 mmol, 7% from 5).

Rf=0.28 ($SiO_2$, F-254, $CH_2Cl_2$/MeOH 90:10). M.p.=136-138° C. $^1$H-NMR ($CD_3OD$, 400 MHz) δ: 0.71 (3H, s, 18-$CH_3$), 0.87-0.98 (6H, m, 19-$CH_3$+$CH_2CH_3$), 1.01 (3H, d, J=6.6 Hz, 21-$CH_3$), 3.29-3.33 (1H, m, 3-CH), 3.63 (1H, s, 7-CH), 4.14 (1H, dd, $J_1$=3.9 Hz, $J_2$=11.7 Hz, 23-CH), 4.59 (1H, bs, NH). $^{13}$C-NMR ($CD_3OD$, 100.6 MHz) δ 12.0, 12.2, 18.2, 21.9, 23.5, 23.8, 24.5, 29.4, 30.8, 31.2, 34.4, 34.5, 36.6, 36.7, 36.8, 40.9, 41.4, 41.5, 43.1, 43.9, 46.9, 51.7, 57.6, 71.1, 73.2, 174.4, 179.6.

Example 25: Physico-Chemical Properties

Critical Micellar Concentration

The detergency was evaluated by calculating the critical micellar concentration (CMC) with two different methods: surface tension (ST) and dye solubilization (Roda et al. 1983). In the first method, the surface tension was performed by maximum bubble-pressure method using a Sensadyne 6000 tensiometer (Chem-Dyne Research Corp., Milwaukee, Wis.). The surface tension of aqueous solutions at various concentrations (range 0.1-100 mM) of the BA sodium salts in 0.1 M NaCl was measured at 25° C. The surface tension values were plotted against the logarithm of the bile salt concentration; the regression lines corresponding to the two parts of the curve (monomeric and micellar phases) were calculated using the method of least squares. The critical micellar concentration (CMC) value (mM) was obtained by the intersection of the two lines.

The second method is based on the fact that some dyes, specifically Orange OT (purchased from Intercept Pharmaceuticals S.p.a., San Diego, Calif.), are almost insoluble in water but dissolve in solutions with micellar aggregates that incorporate them; thus, the intensity of color of the solution increases with bile salt concentration (after CMC achievement). The amount of dye solubilized in relation to bile salt concentration was determined spectrophotometrically.

For each bile acid, various solution at different concentrations, between 50 mM and 0.1 mM with appropriate dilutions, were incubated under stirring at room temperature for 3 days with an excess of Orange OT. Then all the solutions were centrifuged and filtered through a 0.22 μm Millipore fluter (Millipore Corp., Bedford, Mass.).

Absorbance of each solution was measured at 483 nm (typical wavelength of Orange OT absorption) with Spectrofotometer (Wellwarm, Labsystems, Cambridge, UK)
Water Solubility BA were suspended in 100 ml of 0.1 M HCl, pH 1.00, and the saturated solutions were transferred to a thermostat-equipped water bath maintained at 25° C. After incubation for 1 week, the solutions were filtered on a Millipore filter (0.22 mm), and the concentration of BA was measured by HPLC-ESMS/MS as reported below.

Lipophilicity

1-Octanol/water partition coefficient was evaluated using a conventional shake-flask procedure as previously described (Roda et al., 1990). The experiments were carried out on 1 mM initial bile salt solution buffered at pH 8.00 with 0.1 M potassium phosphate buffer to ensure complete ionization of the BA. BA concentration in the water phase before and after partition in 1-octanol was measured by HPLC-ESMS/MS as reported below.

Albumin Binding

Albumin binding was evaluated by equilibrium dialysis at a fixed BA-albumin ratio (Roda et al., 1982). BA was dissolved at a concentration of 100 mM in 5% bovine serum albumin saline solution and left to stand for 24 hours at 25° C. Two milliliters of this solution was dialyzed in cellulose sacs with a molecular weight cut-off of 12-14 kDa (Spectra/Por; Spectrum Medical Industries Inc., Rancho Dominguez, Calif.) against 25 ml of saline solution. The system was equilibrated by mechanical shaking for 72 hours at 25° C. BA concentrations in the starting solution and in the dialyzed solution were determined by HPLC-ES-MS/MS as reported below.

TABLE 2

| BA | Ws (μM) | CMC (mM) | CMpH | $ST_{CMC}$ Dyne/cm | $LogP_A^-$ | Albumin binding (%) | pKa |
|---|---|---|---|---|---|---|---|
| CDCA | 32 | 3.2 | 7 | 45.5 | 2.2 | 96 | 5 |
| GCDCA | 7 | 2 | 6.4 | 45.2 | 0.4 | 85 | 3.9 |
| TCDCA | hs | 3 | — | 47.1 | 0.9 | 70 | <1 |
| UDCA | 7 | 10 | 8.2 | 50.5 | 2.2 | 94 | 5 |
| CA | 273 | 9 | 6.5 | 49 | 1.1 | 88 | 5 |
| TCA | hs | 4 | — | 51 | −0.5 | 42 | <1 |
| GCA | 32 | 8 | 6.3 | 48.8 | −0.4 | 65 | 3.9 |
| Ref. Cmpd. C | hs | 1.3 | — | 47.9 | 2.0 | 85 | <1 |
| Ref. Cmpd. B | 9 | 2.9 | 7.2 | 48.8 | 2.5 | 96 | 5 |
| Ref. Cmpd. A | 99 | 2 | 6.1 | 50.1 | 1.4 | 62 | 5 |
| T-Ref. Cmpd. A | hs | 1.4 | — | 47.8 | −0.2 | 81 | <1 |
| G-Ref. Cmpd. A | 1700 | 1.3 | 3.9 | 43.8 | 0.3 | 71 | 3.9 |
| Nor-CDCA | 23 | 20 | 7.9 | — | 0.5 | 95 | 5 |
| Compound 3 | 225 | 10 | 2.7 | — | 1.0 | 99 | 1.10* |
| Compound 4 | 3201 | 5 | 4.5 | — | −0.2 | 55 | 4.36* |
| Compound 8 | 971 | 6 | 3.6 | — | 0.01 | 84 | 2.82* |
| Compound 9 | 469 | 6 | 3.9 | — | 0.2 | 89 | 2.82* |
| Compound 10 | 16 | 8.5 | 3.7 | — | 1.4 | 66 | 1.10* |
| Compound 11 | 392 | 5 | 7.0 | — | 1.6 | 84 | 5.94* |
| Compound 12 | 517 | 5 | 6.6 | — | 1.5 | 83 | 5.59* |
| Compound 14 | 2025 | 10 | 5.0 | — | 1.9 | 99 | 5 |
| Compound 15 | 132 | n.d. | n.c. | — | 1.2 | 76 | 5.59* |
| Compound 17 | 5 | 11 | 9.0 | — | 2.0 | 90 | 5.71* |
| Compound 19 | 2151** | 5 | 1.3 | — | 1.0 | 51 | 14.3* |
| Compound 21 | 1814 | 4 | 14.6 | — | 0.9 | 86 | <1 * |

CDCA: chenodeoxycholic acid

GCDCA: glycine conjugate of CDCA

TCDCA: famine conjugate of CDCA nor-CDCA: 24-nor-CDCA

UDCA: ursodeoxycholic acid

CA: cholic acid

GCA: glycine conjugate of CA

TCA: taurine conjugate of CA

T-Ref. Cmpd A: taurine conjugate of Ref. Cmpd A

G-Ref. Cmpd A: glycine conjugate of Ref. Cmpd A

Ref. Cmpd. A

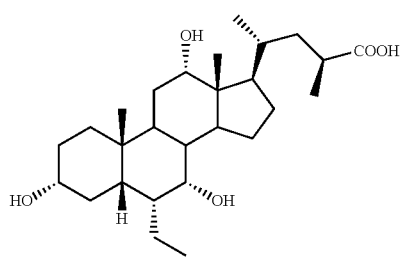 [SMILES: CC[C@H]1[C@@H](O)C2C3CC[C@H]([C@H](C)C[C@H](C)C(=O)O)[C@@]3(C)[C@@H](O)CC2[C@@]2(C)CC[C@@H](O)C[C@@H]12]

TABLE 2-continued

| BA | Ws (μM) | CMC (mM) | CMpH | ST$_{CMC}$ Dyne/cm | LogP$_A^-$ | Albumin binding (%) | pKa |
|---|---|---|---|---|---|---|---|

Ref. Cmpd. C

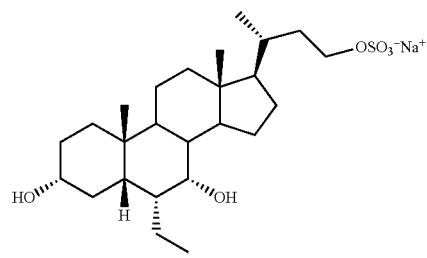

Ref. Cmpd. B

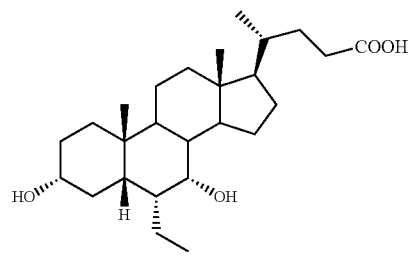 [SMILES: CC[C@H]1[C@@H](O)C2C3CC[C@H]([C@H](C)CCC(=O)O)[C@@]3(C)CCC2[C@@]2(C)CC[C@@H](O)C[C@@H]12]

Example 26: In Vitro TGR5/FXR Activity

Screening Assay

FXR activity: AlphaScreen coactivator recruitment assay. Activation of the FAR receptor was determined using a recruitment coactivator assay, namely Alpha Screen technology. The assays were performed using human glutathione transferase-tagged FXR-LBD (Life Technologies, USA) and mouse glutathione transferase-tagged FXR-LBD (generated in-house). Briefly, assays were conducted in white, low-volume, 384-well OptiPlate using a final volume of 25 μL containing 10 nM glutathione transferase-tagged FXR-LBD protein and 30 nM biotinylated Src-1 peptide. The stimulation was carried out with different BA concentrations for 30 minutes at 25° C. Luminescence was read in an EnVision 2103 microplate analyzer (Perkin Elmer, USA) after incubation with the detection mix (acceptor and donor beads) for 4 hrs at 25° C. in the dark. Dose-response curves were performed in triplicate and Z' factor was used to validate the robustness of the assay.

TGR5 activity: Intracellular cAMP levels detection. Activation of TGR5 was assessed by measuring the level of cAMP using an HTR-FRET assay. Thus, NCI-H716 cells were cultured on 96-well plates coated with Matrigel (Corning, USA) (0.75 mg/ml) in DMEM supplemented with 10% FCS, 100 units/ml penicillin, and 100 μg/ml streptomycin sulphate. After 24 hrs, cells were stimulated with increasing concentrations of test BA for 60' at 37° C. in OptiMEM (Life Technologies, CA, USA) containing 1 mM 3-isobutyl-1-methylxanthine. The level of intracellular cAMP was determined with Lance kit. Z' factor was used to validate assays.

hTGR5 CHO-k1 and mTGR5 CHO-Pi10 clone 4 were maintaining in culture medium: DMEM F12 with 10% FBS, 10 μg/mL puromycine (Sigma Aldrich) and F12 Kaighn's medium with 10% FBS, 600 μg/mL geneticine (Invitrogen), 10 μg/mL puromycine (Sigma Aldrich), respectively.

At the day of the experiment, cells were stimulated with different concentrations of test compounds dispensed by HP D300 Digital Dispenser for 30' at 37° C. according to previous protocol.

Cytotoxicity Assays

Cell viability was evaluated by measuring ATP levels using CellTiter-Glo (Promega), according to the manufacturer's instructions. LCA was used as bile acid comparator for cell cytotoxicity, whereas tamoxifen (Sigma) was used as a control of the assay. Cell necrosis was evaluated by measuring the release of lactate dehydrogenase (LDH) from the necrotic cells using CytoTox-ONE, a homogeneous membrane integrity assay (Promega), according to manufacturer's instructions. For analyses of cell viability (ATP levels), apoptosis and necrosis (LDH release), $2\times10^4$ HepG2 cells were stimulated in MEM (EuroClone) medium with 2 mM L-Glutamine (EuroClone), 1% penicillin/streptomycin (EuroClone) and 10% FBS (EuroClone) with test compounds at concentrations ranging from 100 nM to 350 μM in a white 96-well microplate for 4 hrs at 37° C.

GLP1 Secretion

Human NCI-H716 cells were seeded into 24-well culture plates precoated with Matrigel (BD Bioscences) in DMEM high glucose (EuroClone), 2 mM L-Glutamine (EuroClone), 1% penicillin/streptomycin (EuroClone), 10% FBS (EuroClone). Twenty-four hours later, the supernatants were replaced by PBS containing 1 mM CaCl and dipeptidyl peptidase IV inhibitor diprotin-A (Sigma) and stimulated with tested compound for 1 h at 37° C. GLP-1 was measured by Bio-Plex (Bio-Rad Laboratories) and normalized to protein content.

Biological activities of representative compounds of the application are presented in Table 3.

TABLE 3

| Cmpd | TGR5 (NCI-H716) $EC_{50}$ (μM) | TGR5 (NCI-H716) Efficacy (%) | hTGR5 CHO (mTGR5 CHO) $EC_{50}$ (μM) | hTGR5 CHO (mTGR5 CHO) Efficacy (%) | hFXR (mFXR) $EC_{50}$ (μM) | hFXR (mFXR) Efficacy (%) | GLP-1 Secretion Fold relative to NT (%) |
|---|---|---|---|---|---|---|---|
| Ref. LCA | 3.2 – 8 | 100% at 10 μM | 0.8 ± 0.3 | 100% at 10 μM | — | — | — |
| Ref. CDCA | — | — | — | — | 10 – 20 | 100% at 50 μM | — |
| Ref. tamoxifen | — | — | — | — | — | — | — |
| 1 | 19 | 40 | 3.5 ± 1.5 (0.7 ± 0.3) | 103 ± 1 (115 ± 2) | 32 ± 8 (146 ± 15) | 52 (9 ± 3) | — |
| 2 | 12 | 55 | 17 ± 2 (1.5 ± 0.2) | 47.5 ± 2.5 (93.5 ± 3) | 20 ± 9 (84 ± 6) | 200 (61 ± 1) | — |
| 3 | 9 | 65 | 1.5 ± 0.5 (0.18 ± 0.03) | 110 ± 7.3 (110 ± 11) | 4.3 ± 1.7 (28.5 ± 0.5) | 115 ± 40 (69 ± 1) | 140 |
| 4 | 7.5 ± 5 | 77 ± 10 | 4.65 ± 0.5 (1.3 ± 0.3) | 99 ± 1.4 (102.5 ± 0.01) | 80 ± 30 (>150) | 20 ± 2 | 230 ± 0.5 |
| 5 | — | — | 21 (3.4) | 43.6 (84.6) | 20 | 37 | — |
| 6 | — | — | 29.5 (3.8) | 28 (81) | >100 | — | — |
| 7 | — | — | 7.9 (2) | 27 (119) | 13 | 83 | — |
| 8 | 7 ± 3 | 97 ± 1.7 | 0.5 ± 0.1 (0.78 ± 0.1) | 103 ± 2 (100 ± 2) | 5.6 ± 1 (59.5 ± 2) | 113 ± 3 (47 ± 7) | 340 ± 0.8 |
| 9 | 22 ± 3 | 75 ± 6 | 1.4 ± 0.3 (1.8 ± 0.2) | 98 ± 2 (90 ± 10) | 2.9 ± 0.9 (55 ± 2) | 147 ± 20 (127 ± 5) | 270 ± 0.7 |
| 10 | 1.6 ± 0.2 | 125 ± 1 | 0.34 ± 0.04 (0.6 ± 0.1) | 103 ± 1 (102 ± 6) | 0.2 ± 0.04 (7.1 ± 2) | 128 ± 4 (143 ± 3) | 260 |
| 11 | 2 | 105 | 2.7 ± 1.8 (1.4 ± 0.75) | 96 ± 19 (108 ± 7.8) | 1 (7.7 ± 1) | 140 (100 ± 16) | 900 ± 2 |
| 12 | 4 | 104 | 0.71 ± 0.08 (0.84 ± 0.14) | 101 ± 1.4 (105 ± 0.7) | 1.7 ± 0.6 (12.7 ± 4) | 125 ± 15 (93 ± 1) | 420 ± 1 |
| 13 | 6.4 ± 1.1 | 84 ± 14 | 1 ± 0.1 (2.3 ± 0.5) | 102 ± 3 (90 ± 4) | 0.43 (1.4 ± 0.1) | 138 (208 ± 2) | — |
| 14 | 1.6 ± 0.3 | 110 ± 2 | 0.48 ± 0.3 (0.9 ± 0.2) | 107 ± 1 (111 ± 2) | 0.075 ± 0.01 (0.46 ± 0.04) | 165 ± 15 (264 ± 31) | 290 ± 0.8 |
| 15 | 5 ± 1 | 97 ± 7.6 | 0.72 ± 0.05 (0.44 ± 0.1) | 99 ± 3 (102 ± 5) | 0.15 ± 0.05 (6 ± 2) | 173 ± 22 (222 ± 23) | — |
| 16 | 3 ± 0.3 | 116 ± 9 | 1.2 ± 0.1 (0.44 ± 0.1) | 99 ± 4 (99 ± 9) | 0.15 ± 0.05 (6.6 ± 1) | 165 ± 19 (204 ± 25) | — |
| 17 | 1.2 ± 0.1 | 119 ± 2 | 0.1 ± 0.04 (0.8 ± 0.2) | 103 ± 2 (101 ± 5) | 0.45 ± 0.05 (2.3 ± 0.3) | 138 ± 9 (171 ± 1) | — |
| 18 | 1.8 ± 0.2 | 115 ± 4 | 0.11 ± 0.03 (0.37 ± 0.1) | 104 ± 1 (101 ± 6) | 0.55 ± 0.03 (2.3 ± 0.3) | 132 ± 8 (150 ± 4) | — |
| 23 | 12.5 ± 1.5 | 75 ± 1 | 1.3 ± 0.1 (1.4 ± 0.4) | 111 ± 2 (110 ± 10) | 0.1 ± 0.02 (0.33 ± 0.01) | 175 ± 22 (342 ± 35) | — |
| 19 | 0.16 ± 0.01 | 128 ± 1 | 0.02 ± 0.008 (0.08 ± 0.01) | 105 ± 2 (106 ± 4) | 3 ± 1 (10 ± 1) | 137 ± 2 (122 ± 2) | 500 ± 1 |
| 20 | 0.7 ± 0.1 | 148 ± 1 | 0.3 ± 0.14 (0.5 ± 0.15) | 109 ± 5 (101 ± 4) | 8.7 ± 0.04 (16 ± 4) | 122 ± 3 (85 ± 4) | 190 ± 0.3 |
| 21 | 0.19 ± 0.05 | 127 ± 1 | 0.02 ± 0.01 (0.07 ± 0.03) | 105 ± 2 (107 ± 3) | 1.5 ± 0.5 (5.4 ± 0.02) | 136 ± 7 (136 ± 5) | 450 ± 0.5 |

Example 27: Pharmacokinetic Properties after Oral Administration at 30 mg/kg to Ob/Ob Mouse Pharmacokinetics studies were performed in male ob/ob mice (9-10 wk-old, Janvier/Charles River Laboratories). Mice were orally dosed with compounds (30 mg/kg suspension in 0.5% hydroxyethylcellulose). Blood was sampled 10, 30 min and 1, 2, 4, 6 and 24 hours after administration into Lithium-Heparin tubes. Plasma was collected upon centrifugation and frozen for further measurements. The plasma concentration of the compound was determined using a HPLC-ESI-MS/MS method following an on-line extreaction (Turboflow). The MS system (Sciex API4000) was set with an electrospray ionization source (Turbospray) in the negative mode with optimized parameters. Chromatograms were acquired using the mass spectrometer in multiple reaction monitoring mode.

Example 28: OGTT in 3-Day Treated Ob/Ob Mice

Male ob/ob mice (10 wk-old, Janvier, n=9 per group) were orally treated twice a day (BID) for 3 days with vehicle (0.5% HEC) or the BA under study (100 mg/kg). Immediately after the last administration, mice were fasted for 4 hours. Then an oral glucose tolerance test was performed (glucose 1.5 g/kg). Blood samples were collected at T0 (before glucose administration), 10, 25, 60 and 120 minutes for blood glucose levels determination using a glucometer and at T0 (before glucose administration), 10, 25 and 60 minutes for plasma insulin level measurement (ALPCO ELISA kit). At the end of the experiments, bile volume within the gallbladder was determined in anesthetized mice.

Example 29: In Vivo GLP-1 Secretion in Normal Mice

Male $C_{57}Bl/6$ mice (9 wk-old, Janvier) were overnight fasted and then orally treated with the BA under study (100 mg/kg), followed by sitagliptin (1 mg/kg). The time between administration of the BA under study and sitagliptin varies between 0 and 3 hours, depending on the PK profile of the BA under study. One hour after sitagliptin treatment, mice were orally challenged with glucose (1.5 g/kg). Before and 5 minutes after glucose challenge, blood was collected for blood glucose determination using a glucometer (AccuChek) and for plasma recovery using K3-EDTA tubes containing DPP-IV inhibitor. Plasma levels of active GLP1 were measured by ELISA according to manufacturer's instructions (Linco-Millipore). At the end of the experiments, bile volume within the gallbladder was determined in anesthetized mice.

Example 30: Pharmacokinetic Study in "Bile Fistula Rat" Model

Bile fistula rat model was reported in Roda et al., 2014, J. Pharmacol Exp Ther, Supplemental Data IV. Briefly, after animals were anesthetized, the bile duct was cannulated, and the BAs were delivered either intravenously or intraduodenally per gavage. Each bile acid was infused at a dose of 1 mmol/min/kg body weight over 1 hour at 2.5 ml/hour. Bile was collected at 15-minute time intervals throughout the infusion and over 2 hours after the infusion was over. Plasma was collected at 30-minute time intervals throughout the intraduodenal infusion and over 2 hours after the infusion was over while for the intravenous infusion plasma samples were collected at beginning and at the end of experiment. Liver and intestinal content were collected at the end of each experiment.

HPLC-ES-MS/MS Method

As previously reported (Roda et al., 2014, J Pharmacol Exp Ther), BAs were separated in elution gradient mode using 15 mM ammonium acetate buffer (pH 8.00) as mobile phase A and acetonitrile/methanol (75:25 v/v) as mobile phase B. The MS system was set with an electrospray ionization source (ES) in the negative mode with optimized parameters. Chromatograms were acquired using the mass spectrometer in multiple reaction monitoring mode.

Bile Sample Preparation

Rat bile samples were brought to 25° C. and diluted 1:100 or 1:10 (v/v) with ammonium acetate buffer 15 mM, pH 8.00, and acetonitrile/methanol (3:1 v/v) in ratio 65:35 (v/v). The final solution was transferred to an autosampler vial, and 5 ml was injected onto the column. The bile secretion flow results are expressed as µmol/kg/min while the bile flow results are expressed as 4/kg/min.

Plasma Sample Preparation.

As previously reported (Roda et al., 2014, J Pharmacol Exp Ther), plasma samples (100 ml) were diluted 1:6 (v/v) with 0.1 N NaOH and heated to 64° C. for 30 minutes. The solid phase extraction (SSPE) C18 cartridge was conditioned with 5 ml of methanol and 5 ml of water prior to sample loading. Plasma samples were loaded into the conditioned cartridge and then washed with 10 ml of water. The cartridge was then eluted with 5 ml of methanol, the eluate was dried under vacuum and then reconstituted with 200 ml of the mobile phase, and 5 µl was injected into the HPLC-ES-MS/MS instrument. The results are expressed as µM.

Liver Sample Preparation.

As previously reported (Roda et al., 2014, J Pharmacol Exp Ther), aliquots weighing approximately 1 g each were taken from different points of the liver sample. Each aliquot was weighed, and 2 ml of phosphate buffer (0.005 M, pH 7.2) was added. The mixture was homogenized using a potter, which was then washed with methanol (3×1 ml). The mixture was sonicated for 5 minutes, vortexed for 2 minutes, heated to 37° C. for 20 minutes, and centrifuged (2100 g for 15 minutes). One milliliter of the supernatant was spiked with 10 ml of the internal standard working solution and dried under vacuum. The residue then was resuspended with 2 ml of NaOH (0.1 N). The solution was sonicated for 10 minutes, heated to 64° C. for 30 minutes, and SPE was carried out on C18 extreaction cartridges (as shown above). The eluate was dried under vacuum and reconstituted with 200 ml of the mobile phase and injected into the HPLC-ES-MS system. The results are expressed as µmol/g where g is total liver weight.

Intestinal Content Sample Preparation

As previously reported (Roda et al., 2014, J Pharmacol Exp Ther), intestinal content sample sample was collected and homogenized using a mixer. Aliquots weighing approximately 1 g were taken from the homogenate. Each aliquot was weighed, and 3 ml of isopropyl alcohol was added. The mixture was vortexed for 2 minutes and centrifuged (2100 g for 10 minutes). The supernatant was then diluted 1:100 v/v with mobile phase, and 190 ml of these final solutions were spiked with 10 ml of internal standard. The results are expressed as µmol/g where g is total intestinal content weight.

Calibration Curve

Calibration curve of bile, stool and liver sampled was performed in mobile phase, linearity range 0.1-20 nM. For plasma sample, the calibration curve was obtained using BA free rat plasma in linearity range 0.1-20 nm.

Recovery %

The recovery % was evaluated comparing the amount of BA under study and its metabolites in each matrix with the total amount of BA administered.

Other Embodiments

While the application has been described in conjunction with the detailed description thereof, the foregoing description is intended to illustrate and not limit the scope of the application, which is defined by the scope of the appended claims. Other aspects, advantages, and modifications are within the scope of the following claims. It will be understood by those skilled in the art that various changes in form and details may be made therein without departing from the scope of the application encompassed by the appended claims.

The invention claimed is:

1. A compound selected from the group consisting of:

| Cmpd No. | Chemical Structure |
|---|---|
| 1 | (structure) |
| 2 | (structure) |
| 3 | (structure) |
| 4 | (structure) |
| 5 | (structure) |
| 6 | (structure) |
| 7 | (structure) |
| 8 | (structure) |
| 9 | (structure) |
| 10 | (structure) |

| Cmpd No. | Chemical Structure |
|---|---|
| 11 | [Steroid structure with 3α-OH, 7α-OH, 12α-OH, 6-ethyl, and side chain terminating in 1,2,4-oxadiazol-5(4H)-one] |
| 12 | [Steroid structure with 3α-OH, 7α-OH, 12α-OH, 6-ethyl, and side chain terminating in tetrazole] |
| 17 | [Steroid structure with 3α-OH, 7α-OH, 16-OH, 6-ethyl, and side chain terminating in tetrazole] |
| 18 | [Steroid structure with 3α-OH, 7α-OH, 16-OH, 6-ethyl, and side chain terminating in 1,2,4-oxadiazol-5(4H)-one] |
| 19 | [Steroid structure with 3α-OH, 7α-OH, 6-ethyl, and side chain terminating in C(O)NH-CH$_2$CH$_2$-OH] |
| 20 | [Steroid structure with 3α-OH, 7α-OH, 6-ethyl, and side chain terminating in C(O)NH-OH] |
| 21 | [Steroid structure with 3α-OH, 7α-OH, 6-ethyl, and side chain terminating in C(O)NH-CH$_2$CH$_2$-OSO$_3$Na] |
| 22 | [Steroid structure with 3α-OH, 7α-OH, 6-ethyl, and side chain terminating in CF$_2$-COOH] |
| 23 | [Steroid structure with 3α-OH, 7α-OH, 6-ethyl, and side chain terminating in 1,3,4-oxadiazol-2-yl-NHS(O)$_2$CH$_3$] |
| 25 | [Steroid structure with 3α-OH, 7α-OH, 6-ethyl, and side chain terminating in 1,2,4-oxadiazol-5(4H)-one] |

| Cmpd No. | Chemical Structure |
|---|---|
| 26 | 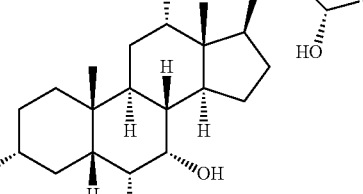 |
| | and |
| 27 | 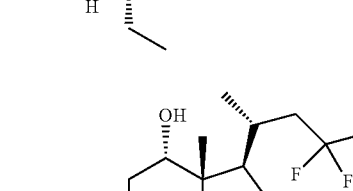 |
or a pharmaceutically acceptable salt, ester, tautomer, or amino acid conjugate thereof.
2. The compound of claim 1, wherein the compound is selected from the group consisting of:
| Cmpd No. | Chemical Structure |
|---|---|
| 1 | 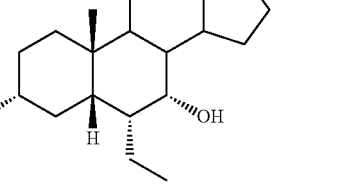 |
| 2 | 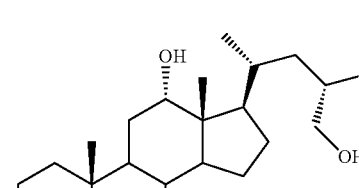 |
| 3 | 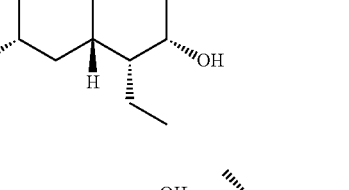 |
| 4 | 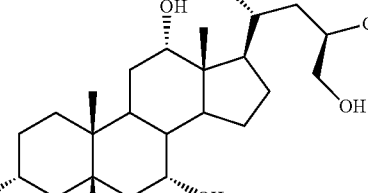 |
| 5 | 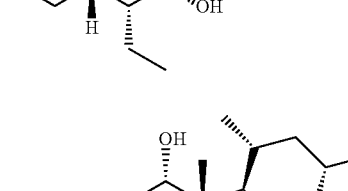 |
| 6 | 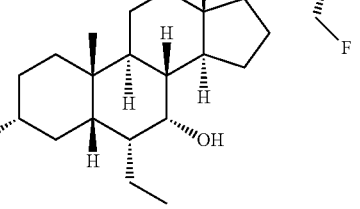 |

-continued

| Cmpd No. | Chemical Structure |
|---|---|
| 7 | [steroid structure with OH, COOH, F substituents] |
| 8 | [steroid structure with OH, COOH, F substituents] |
| 9 | [steroid structure with OH, COOH, F substituents] |
| 10 | [steroid structure with OH, COOH, F, F substituents] |
|  | and |
| 22 | [steroid structure with F, F, COOH substituents] | or a pharmaceutically acceptable salt, ester, tautomer, or amino acid conjugate thereof.

3. The compound of claim 1, wherein the compound is selected from the group consisting of:

| Cmpd No. | Chemical Structure |
|---|---|
| 11 | [steroid structure with oxadiazolone] |
| 12 | [steroid structure with tetrazole] |
| 17 | [steroid structure with tetrazole and OH] |
|  | and |
| 18 | [steroid structure with oxadiazolone and OH] | or a pharmaceutically acceptable salt, ester, tautomer, or amino acid conjugate thereof.

4. The compound of claim 1, wherein the compound is selected from the group consisting of:

| Cmpd No. | Chemical Structure |
|---|---|
| 19 | 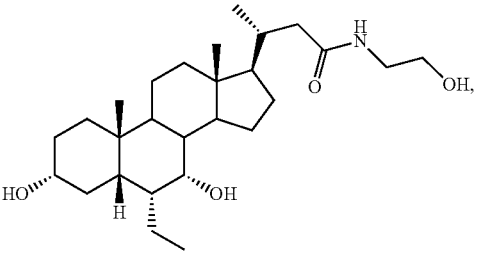 [SMILES: CC[C@H]1[C@@H](O)C2C3CC[C@H]([C@H](C)CC(=O)NCCO)[C@@]3(C)CCC2[C@@]2(C)CC[C@@H](O)C[C@@H]12] |
| 20 | 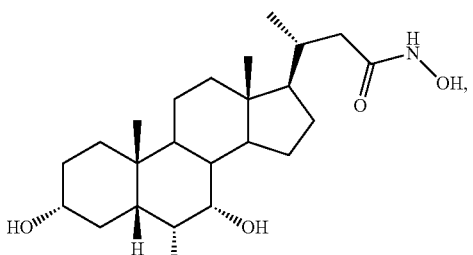 and |
| 21 | 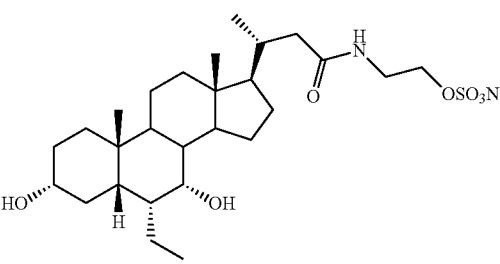 | or a pharmaceutically acceptable salt, ester, tautomer, or amino acid conjugate thereof.

5. The compound of claim 1, wherein the compound is selected from the group consisting of:

| Cmpd No. | Chemical Structure |
|---|---|
| 23 | 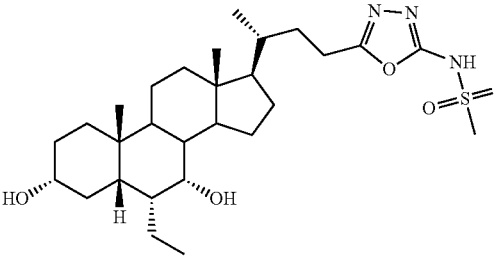 |

-continued

| Cmpd No. | Chemical Structure |
|---|---|
| 25 | 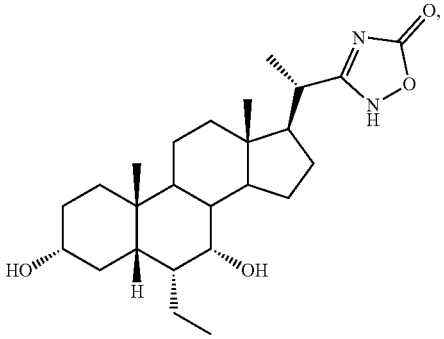 [SMILES: CC[C@H]1[C@@H](O)C2C3CC[C@H]([C@H](C)c4nc(=O)o[nH]4)[C@@]3(C)CCC2[C@@]2(C)CC[C@@H](O)C[C@@H]12] |
| 26 | 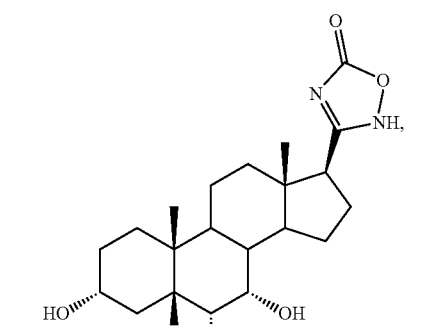 and |
| 27 | 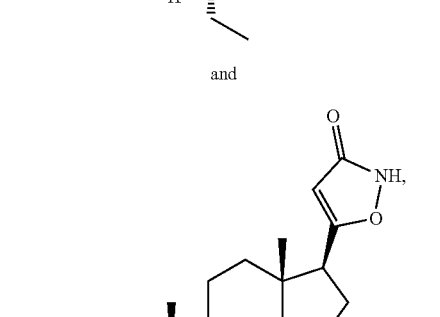 | or a pharmaceutically acceptable salt, ester, tautomer, or amino acid conjugate thereof.

6. A pharmaceutical composition comprising the compound of claim 1 or a pharmaceutically acceptable salt, ester, tautomer, or amino acid conjugate thereof, and at least one pharmaceutically acceptable excipient.

\* \* \* \* \*